(12) United States Patent
Sobel et al.

(10) Patent No.: US 9,959,392 B2
(45) Date of Patent: May 1, 2018

(54) OLFACTORY SIGNATURE AND ODORANT MIXTURE HAVING THE SAME

(75) Inventors: Noam Sobel, Jaffa (IL); Tali Weiss, Rehovot (IL); Kobi Snitz, Rehovot (IL); Adi Yablonka-Barak, Rehovot (IL); Elad Schneidman, Rehovot (IL); Rehan Mahmood Khan, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days. days.

(21) Appl. No.: 14/343,064

(22) PCT Filed: Sep. 6, 2012

(86) PCT No.: PCT/IB2012/054621
§ 371 (c)(1),
(2), (4) Date: Mar. 6, 2014

(87) PCT Pub. No.: WO2013/035070
PCT Pub. Date: Mar. 14, 2013

(65) Prior Publication Data
US 2014/0221269 A1 Aug. 7, 2014

Related U.S. Application Data

(60) Provisional application No. 61/531,689, filed on Sep. 7, 2011.

(51) Int. Cl.
*C11B 9/00* (2006.01)
*G06F 19/00* (2018.01)
(Continued)

(52) U.S. Cl.
CPC .......... *G06F 19/709* (2013.01); *C11B 9/0015* (2013.01); *C11B 9/02* (2013.01);
(Continued)

(58) Field of Classification Search
CPC ................................. C11B 9/00; G06F 19/709
See application file for complete search history.

(56) References Cited

U.S. PATENT DOCUMENTS 7,413,731 B2 8/2008 Heltovics et al.
8,880,448 B2 11/2014 Haddad et al.
(Continued)

FOREIGN PATENT DOCUMENTS

| EP | 1336844 | 8/2003 |
|---|---|---|
| WO | WO 2013/035070 | 3/2013 |
| WO | WO 2015/037003 | 3/2015 |

OTHER PUBLICATIONS

Saito et al. ("Odor Coding by a Mammalian Receptor Repertoire", 2009, Science Signaling, vol. 2, No. 60, pp. 1-14).*
(Continued)

*Primary Examiner* — Arrie L Reuther

(57) ABSTRACT

An odorant mixture is disclosed. The odorant mixture comprises N odorant components wherein N equals at least 20. Each odorant component is characterized by a multidimensional vector of attributes. A z score of an average of characteristic distances between vectors corresponding to odorant components in the mixture and vectors corresponding to odorant components in a group of M odorant components but not in the mixture is less than 2.

14 Claims, 13 Drawing Sheets

(51) Int. Cl.
    G01N 33/00    (2006.01)
    C11B 9/02     (2006.01)
    G06F 17/30    (2006.01)
(52) U.S. Cl.
    CPC ..... *G01N 33/0001* (2013.01); *G01N 33/0004* (2013.01); *G06F 19/704* (2013.01); *G06F 17/30424* (2013.01); *G06F 19/705* (2013.01)

(56) References Cited

U.S. PATENT DOCUMENTS

| | | |
|---|---|---|
| 2003/0022082 A1 | 1/2003 | Ohmura et al. |
| 2003/0172717 A1 | 9/2003 | Kita et al. |
| 2006/0191319 A1 | 8/2006 | Kurup |
| 2007/0191257 A1 | 8/2007 | Andretta et al. |
| 2008/0188172 A1 | 8/2008 | Hollemans et al. |
| 2010/0024533 A1 | 2/2010 | Kimura et al. |
| 2012/0143804 A1 | 6/2012 | Haddad et al. |
| 2015/0051842 A1 | 2/2015 | Haddad et al. |
| 2016/0216244 A1 | 7/2016 | Sobel et al. |

OTHER PUBLICATIONS

Baldi, et al. ("When is Chemical Similarity Significant? The Statistical Distribution of Chemical Similarity Scores and Its Extreme Values", 2010, J. Chem. Inf. Model., vol. 50, No. 7, pp. 1205-1222).*
International Search Report and the Written Opinion Dated Dec. 15, 2014 From the International Searching Authority Re. Application No. PCT/IL2014/050812.
Aron "White Noise for Your Nose Cancels Pungent Aromas", New Scientist, Issue 2993, Oct. 30, 2014.
Howard "'White Noise' for Your Nose Cancels Out Nasty Odor", The Huffington Post, Nov. 2, 2014.
Varshney et al. "Olfactory Signals and Systems", arXiv Reprint, 4110.4864(1): 1-13, Oct. 17, 2014.
International Search Report and the Written Opinion Dated Jan. 16, 2013 From the International Searching Authority Re. Application No. PCT/IB2012/054621.
Baldi et al. "When Is Chemical Similarity Significant? The Statistical Distribution of Chemical Similarity and Its Extreme Values", Journal of Chemical Information and Modeling, 50(7): 1205-1222, Jul. 26, 2010.
Haddad et al. "A Metric for Odorant Comparison", Nature Methods, 5(5): 425-429, May 2008.
Haddad et al. "Global Features of Neural Activity in the Olfactory System Form A Parallel Code That Predicts Olfactory Behavior and Perception", The Journal of Neuroscience, 30(27): 9017-9026, Jul. 7, 2010.
Haddad et al. "Measuring Smells", Current Opinion in Neurobiology, 18(4): 438-444, Aug. 31, 2008.
Harel et al. "Towards an Odor Communication System", Computational Biology and Chemistry, 27(2): 121-133, May 2003.
Khan et al. "Predicting Odor Pleasantness From Odorant Structure: Pleasnatness as A Reflection of the Physical World", The Journal of Neuroscience, 27(37): 10015-10023, Sep. 12, 2007.
Mamlouk et al. "On the Dimensions of the Olfactory Perception Space", Neurocomputing, 58-60: 1019-1025, Jun. 30, 2004.
Saito et al. "Odor Coding by a Mammalian Receptor Repertoire", Science Signaling, 2(60): 1-28, Mar. 3, 2009.
International Preliminary Report on Patentability Dated Mar. 20, 2014 From the International Bureau of WIPO Re. Application No. PCT/IB2012/054621.
Communication Pursuant to Rule 164(1) EPC: Supplementary Partial European Search Report Dated May 11, 2015 From the European Patent Office Re. Application No. 12830464.9.
International Search Report and the Written Opinion Dated Nov. 30, 2010 From the International Searching Authority Re. Application No. PCTIL2010/000587.
Official Action Dated Nov. 18, 2013 From the US Patent and Trademark Office Re. U.S. Appl. No. 13/386,445.
Burl et al. "Assessing the Ability to Predict Human Percepts of Odor Quality From the Detector Responses of a Conducting Polymer Composite-Based Electronic Nose", Sensor & Actuators: B Chemical, 72(2): 149-159, 2001.
Dutta et al. "Tea Quality Prediction Using A Tin Oxide-Based Electronic Nose: An Artificial Intelligence Approach", Sensors and Actuators B, XP004443608, 94(2): 228-237, Sep. 1, 2003. p. 230, § 1.4, Fig.1, p. 235, § 4.1, p. 237, 1-h Col., Lines 19-27.
Pardo et al. "Electronic Nose for Coffee Quality Control", Proceedings of the 18th IEEE Instrumentation and Measurement Technology Conference, Budapest, Hungary, May 21-23, 2001, IMTC 2001, XP010546673, 1: 123-127, May 21, 2001.
Tudu et al. "Smell Peak Prediction During Black Tea Fermentation Process Using Time-Delay Neural Network on Electronic Nose Data", Proceedings of the International Conference on Computing: Theory and Applications, ICCTA'07, XP031058246, p. 257-260, Mar. 1, 2007.
Supplementary European Search Report and the European Search Opinion Dated Sep. 16, 2015 From the European Patent Office Re. Application No. 12830464.9.
Official Action Dated Dec. 31, 2014 From the US Patent and Trademark Office Re. U.S. Appl. No. 14/530,903.
Official Action Dated Nov. 8, 2017 From the US Patent and Trademark Office Re. U.S. Appl. No. 14/917,290. (23 pages).
Nave "Scalar Products of Vectors", Georgia State University, Hyperphysics.phy-astr.gsu.edu, date unknown, Webpage Retrieved 2017, 3 pages.
University of Colorado "Linear Algebra: Vectors", University of Colorado, Colorado.edu, P.A-1-A-14, date unknown, Webpage Retrieved 2017, 14 pages.
International Preliminary Report on Patentability dated Mar. 24, 2016 From the International Bureau of WIPO Re. Application No. PCT/IL2014/050812.

* cited by examiner

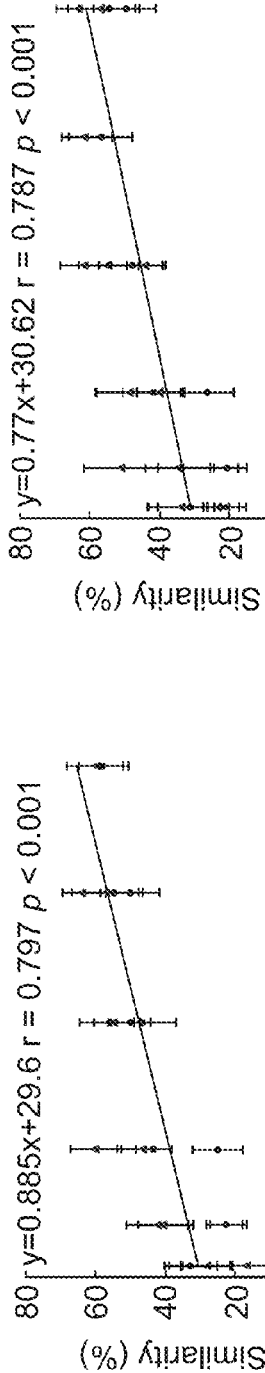
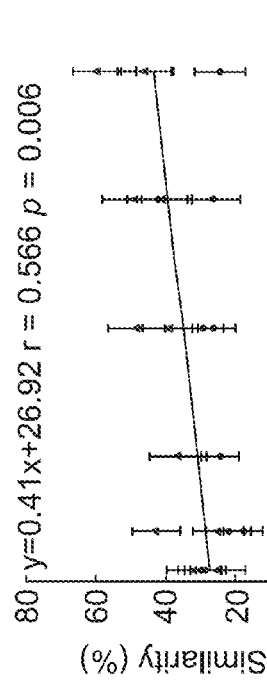
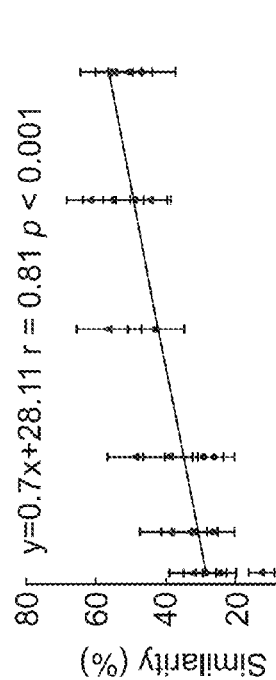
FIG. 7A
FIG. 7B
FIG. 7C
FIG. 7D

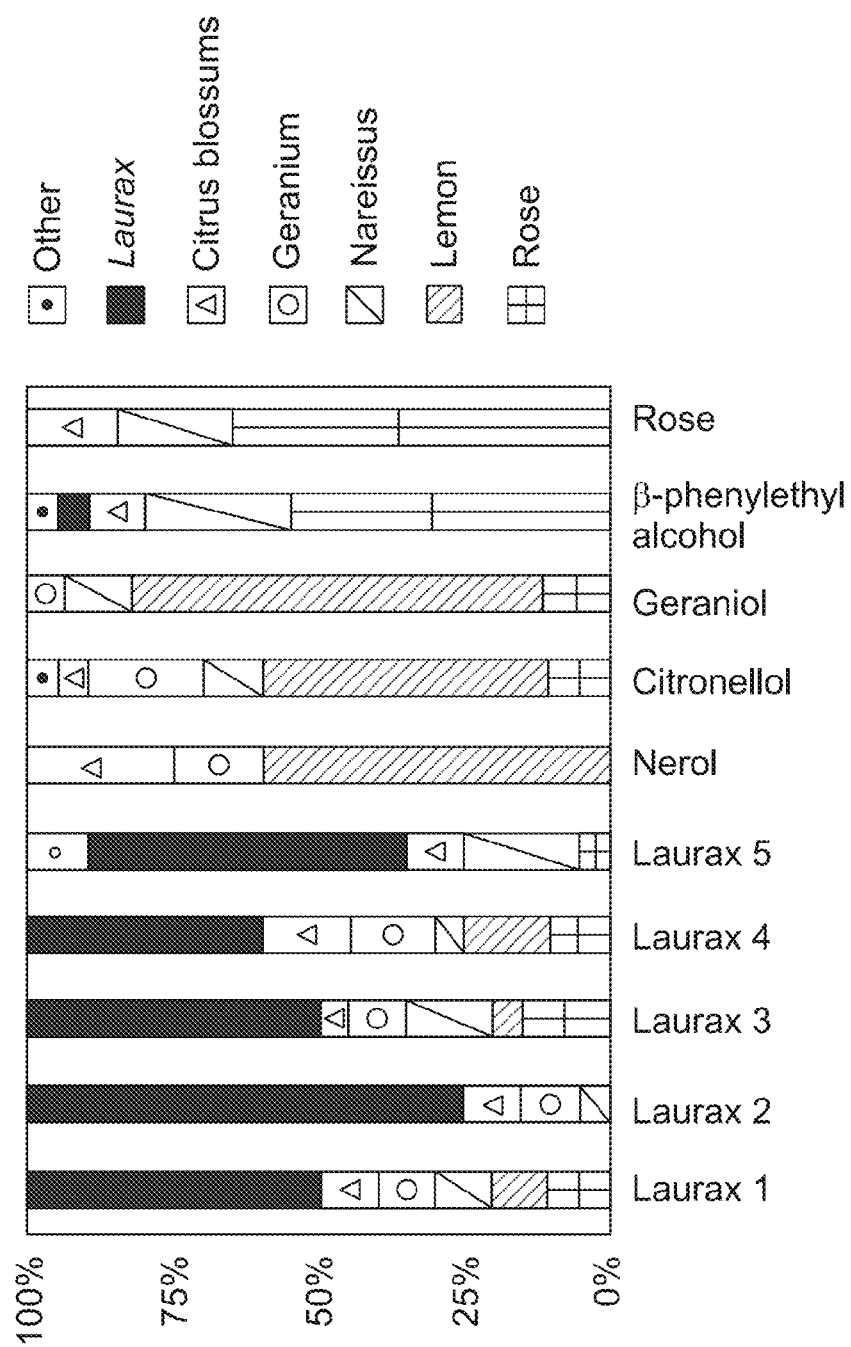

OLFACTORY SIGNATURE AND ODORANT MIXTURE HAVING THE SAME

RELATED APPLICATIONS

This application is a National Phase of PCT Patent Application No. PCT/IB2012/054621 having International filing date of Sep. 6, 2012, which claims the benefit of priority under 35 USC § 119(e) of U.S. Provisional Patent Application No. 61/531,689 filed Sep. 7, 2011. The contents of the above applications are all incorporated by reference as if fully set forth herein in their entirety.

FIELD AND BACKGROUND OF THE INVENTION

The present invention, in some embodiments thereof, relates to an odorant mixture and, more particularly, but not exclusively, to an odorant mixture having an olfactory signature, and method of characterizing an odorant mixture using its olfactory signature.

Several studies have linked human perception of monomolecular odorants to the odorant's physical structure and its specific receptors [Khan et al. (2007) Predicting odor pleasantness from odorant structure: pleasantness as a reflection of the physical world, The Journal of Neuroscience 27(37):10015; Kermen et al. (2011) Molecular complexity determines the number of olfactory notes and the pleasantness of smells, Sci Rep 1:206; Keller et al., (2007) Genetic variation in a human odorant receptor alters odour perception, Nature 449(7161):468-472; and Menashe et al. (2007) Genetic elucidation of human hyperosmia to isovaleric acid. PLoS Biol 5(11):e284].

Odors are complex mixtures of chemical species, and so contain many constituent molecules. The biological olfactory system is a remarkable sensor having many olfactory cells or odorant receptors, but not very many different types of olfactory cells. The characterization of a scent or odor is typically through the combined response of many of the receptors.

Haddad et al. [A metric for odorant comparison, Nature Methods—5, 425-429 (2008)] describes a multidimensional physicochemical metric that took into account many molecular descriptors. Molecular descriptors are mathematical values that describe the structure or shape of a molecule. In Haddad et al., each odorant molecule is represented as a vector containing its descriptor values, and the Euclidean distance between any two odorants is used as a multidimensional metric.

Additional background art includes Saito et al., "Odor Coding by a Mammalian Receptor Repertoire", Sci. Signal. 2, ra9 (2009).

SUMMARY OF THE INVENTION

According to an aspect of some embodiments of the present invention there is provided an odorant mixture, comprising N odorant components wherein N equals at least 20, each odorant component being characterized by a multidimensional vector of attributes, such that the mixture is characterized by N respective multidimensional vectors, wherein a z score of an average of characteristic distances between vectors corresponding to odorant components in the mixture and vectors corresponding to odorant components in a group of M odorant components but not in the mixture is less than 2.

According to some embodiments of the invention at least a portion of the N odorant components is selected from the group of M odorant components.

According to some embodiments of the invention the N odorant components have similar odor intensity.

According to some embodiments of the invention each characteristic distance is defined as a minimum distance between a vector corresponding to odorant components in the mixture and a vector corresponding to an odorant component in the group of M odorant components but not in the mixture.

According to some embodiments of the invention each of the N odorant components is in a gaseous state.

According to some embodiments of the invention the z-score is with respect to a synthetic database which comprises a plurality of entries, each corresponding to a database odorant mixture defined as being producible from a plurality of odorant components selected from the group of M odorant components.

According to an aspect of some embodiments of the present invention there is provided a method of at least partially masking a target odor in an environment. The method comprises spreading an odorant mixture as described herein in the environment, thereby providing a combined mixture having the odorant mixture and odorant components of the target odor.

According to some embodiments of the invention a z score of an average of characteristic distances between vectors corresponding to odorant components in the combined mixture and vectors corresponding to odorant components in the group of M odorant components but not in the combined mixture is less than 1.

According to an aspect of some embodiments of the present invention there is provided a method of determining an olfactory signature of an odorant mixture having N odorant components, the method being executable by a data processor. The method comprises: accessing a database having a group of M odorant components; for each odorant component, obtaining a multidimensional vector of attributes, thereby providing a plurality of multidimensional vectors; calculating a z score of an average of characteristic distances between vectors corresponding to odorant components in the mixture and vectors corresponding to odorant components in the group of M odorant components but not in the mixture; and generating an output comprising the z score, the z score defining the olfactory signature of the odorant mixture.

According to some embodiments of the invention each characteristic distance is defined as a minimum distance between a vector corresponding to odorant components in the mixture and a vector corresponding to an odorant component in the group of M odorant components but not in the mixture.

According to some embodiments of the invention the z-score is calculated with respect to a synthetic database which comprises a plurality of entries, each corresponding to a database odorant mixture defined as being producible from a plurality of odorant components selected from the group of M odorant components.

According to some embodiments of the invention the method comprises generating the synthetic database.

According to some embodiments of the invention M is at least equal to N.

According to some embodiments of the invention each of the multidimensional vectors has at least 50 dimensions or at least 100 dimensions or at least 1000 dimensions.

According to some embodiments of the invention N equals at least 30 or at least 40 or at least 50.

According to some embodiments of the invention M equals at least 100 or at least 1000.

According to some embodiments of the invention the group of M odorant components is selected from the odorant components listed in Table A.1 or Table A.2 of Annex 1.

According to some embodiments of the invention the group of M odorant components is the group listed in Table A.1 of Annex 1.

According to some embodiments of the invention the group of M odorant components is the group listed in Table A.2 of Annex 1.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings.

With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 1A, 1B:
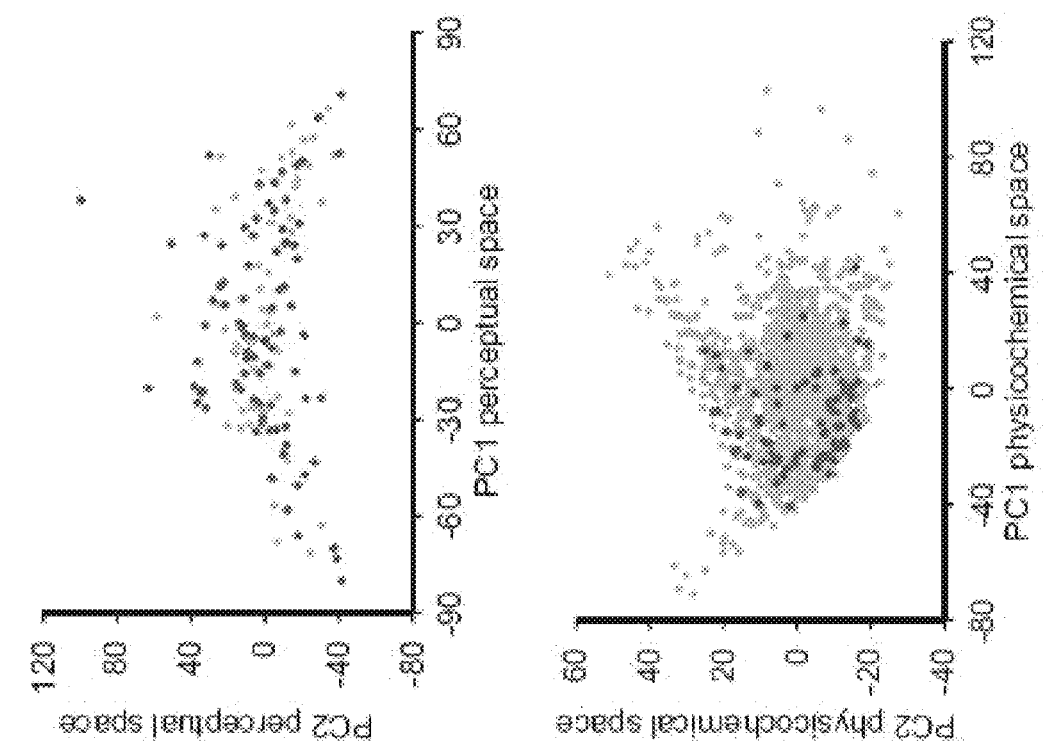

FIGS. 1A-B are graphs illustrating odorants plotted in stimulus space. A. Perceptual space: 144 odorants commonly used in olfaction-research projected onto a two-dimensional space made of PC1 (30.8% of the variance) and PC2 (12% of the variance) of perception; B. Physicochemical space: 1492 odorants commonly modeled in olfaction-research projected onto a two-dimensional space made of PC1 (33.4% of the variance) and PC2 (10% of the variance) of structure. The 86 odorants used are plotted in red. Considerations of human safety prevented the inclusion of odorants that were at the extremes of physicochemical space, as these are often toxic.

Figure 2A:
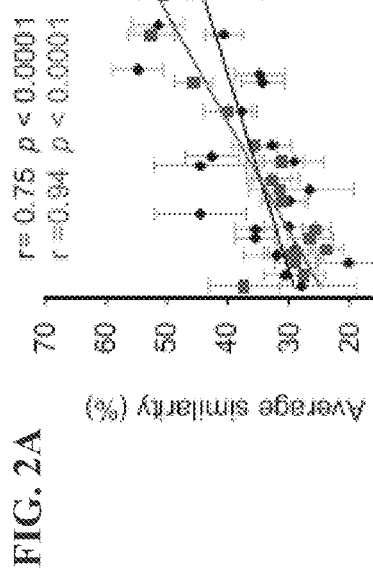
Figure 2B:
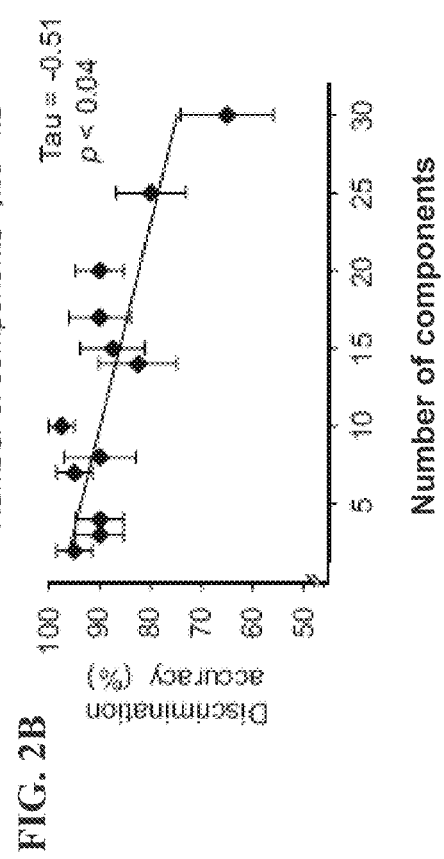
Figure 2C:
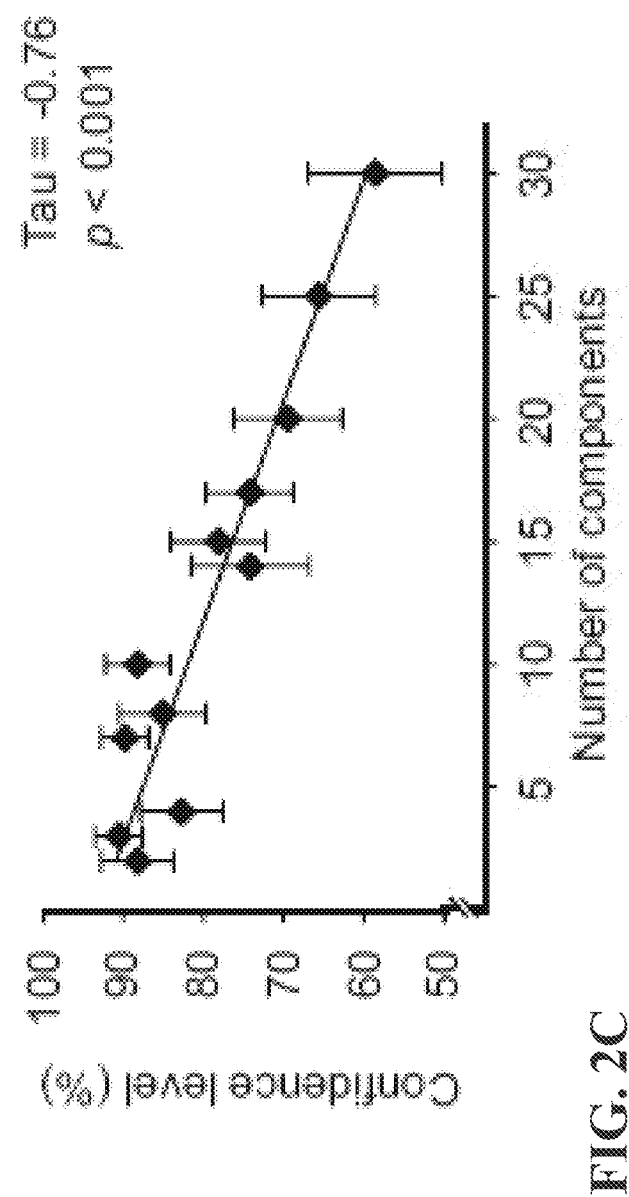

FIGS. 2A-C are graphs illustrating that increasing the number of non-overlapping spanned components in two mixtures renders them more similar and less discernible. A. The average rated similarity for mixture pairs differing in number of components, where mixtures were selected from perceptual space (square) or physicochemical space (diamond). Component number is expressed as the square root of the product of the two mixture sizes B. Discrimination accuracy between a 35-component mixture and nonoverlapping mixtures of various sizes. C. Confidence level ratings. Error bars are standard error.

Figure 3A:
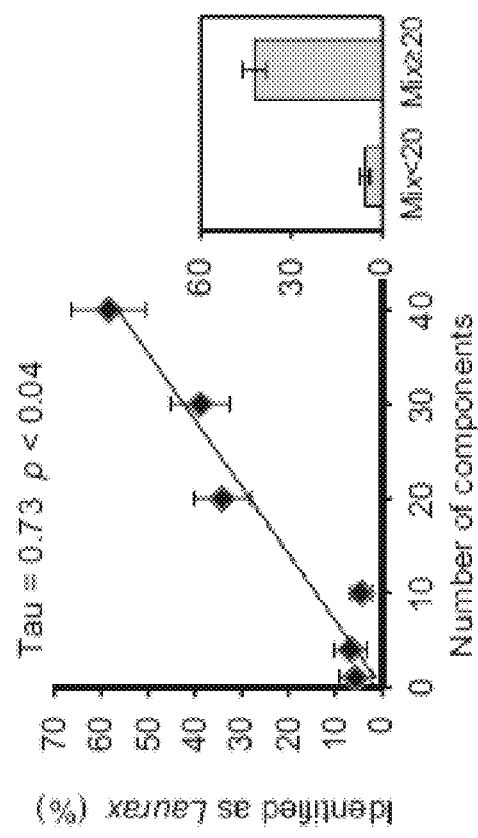
Figure 3B:
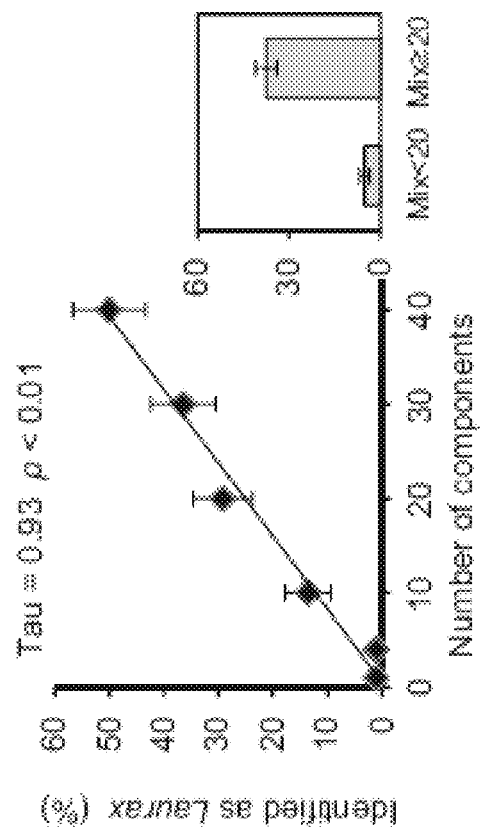

FIGS. 3A-B are graphs illustrating that mixtures made of many equal-intensity spanned components are identified as olfactory white. The average probability of identifying a novel odorant mixture as white ("Laurax") as a function of the number of components in the mixture either in a 4-alternative forced choice identification test (A), or a 5-alternative forced-choice identification test (B). Each dot represents the average rating for four versions of a given number of components. Error bars are standard error. Inset: the average probability of identifying a novel odorant mixture as white (Laurax), for mixtures of less of 20 components, or mixtures of equal or more than 20 components.

Figure 4A:
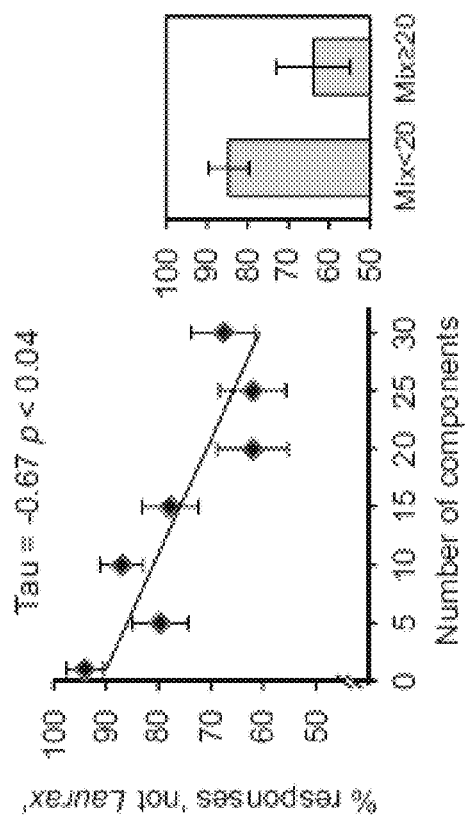
Figure 4B:
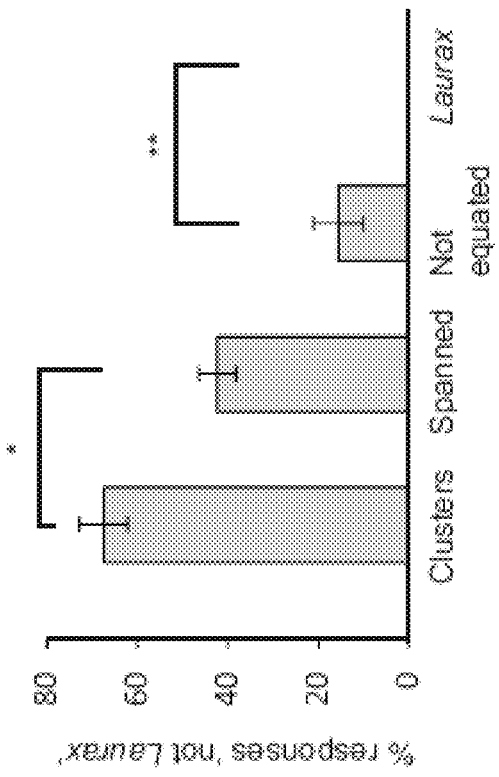

FIGS. 4A-B are graphs illustrating that mixtures made of many equal-intensity spanned components match the perceptual memory of olfactory white. A. Delayed match-to-sample between a learned Laurax and novel non-overlapping mixtures of various sizes. Each dot represents the average rating for three versions of a given number of components. Error bars are standard error. Inset: the average probability of discrimination for mixtures of less than 20 components or mixtures of 20 or more components. B. Delayed match-to-sample between a learned Laurax and novel non-overlapping 25-component mixtures that were either spanned in space, clustered in space, not equated for intensity, or the very same Laurax they learned (100% accuracy). Error bars are standard error between all subjects and versions.

Figure 5:
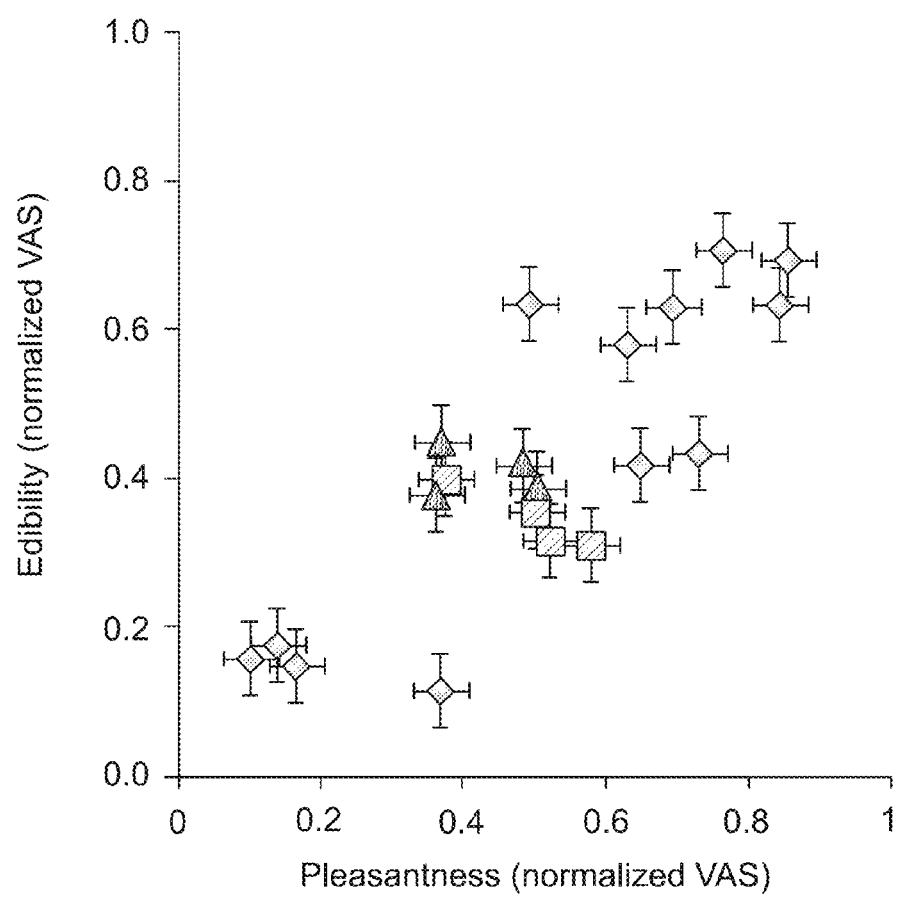
Figure 6A:
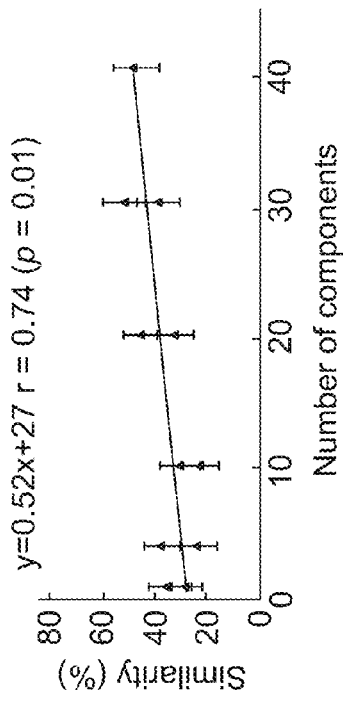
Figure 6B:
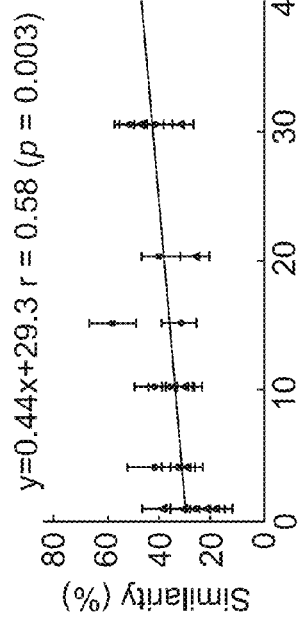
Figure 6C:
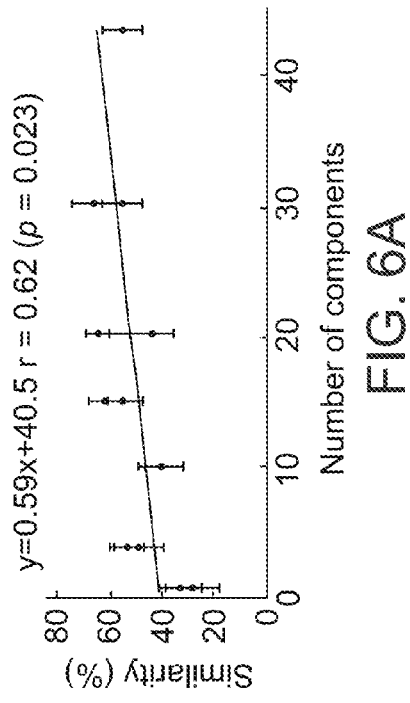
Figure 6D:
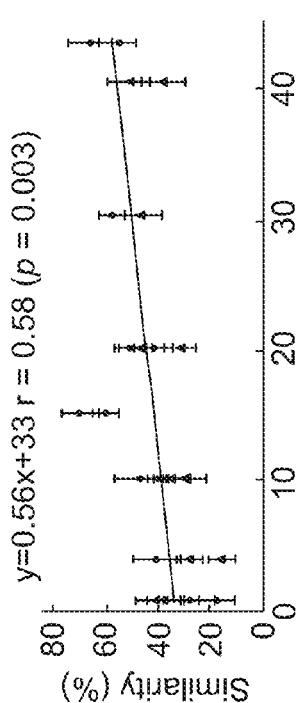
Figure 6F:
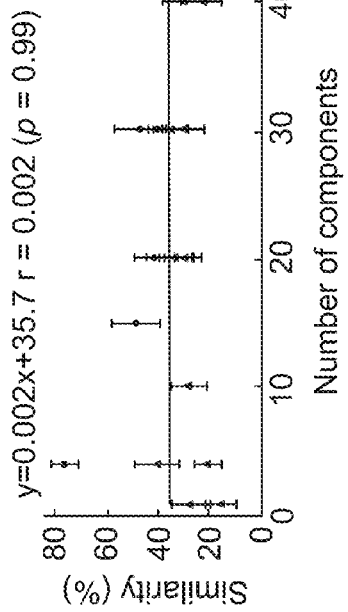
Figure 6H:
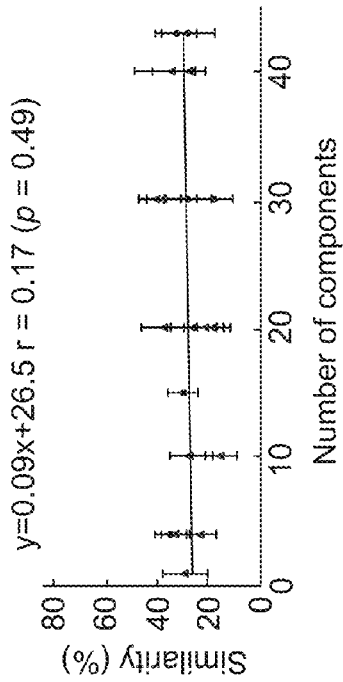
Figure 6E:
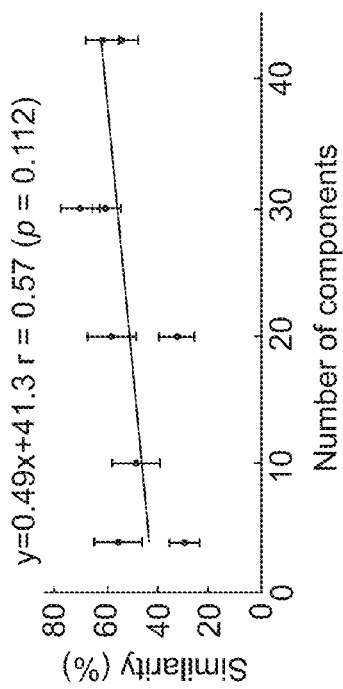
Figure 6G:
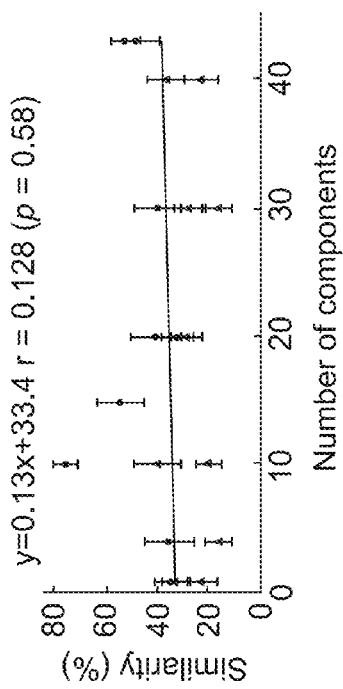
Figure 7E:
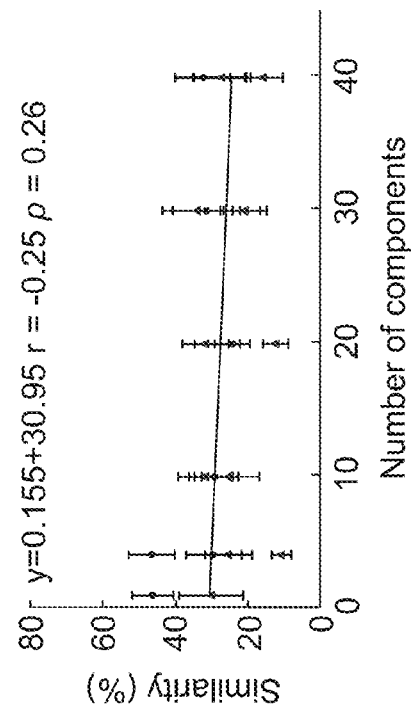
Figure 7F:
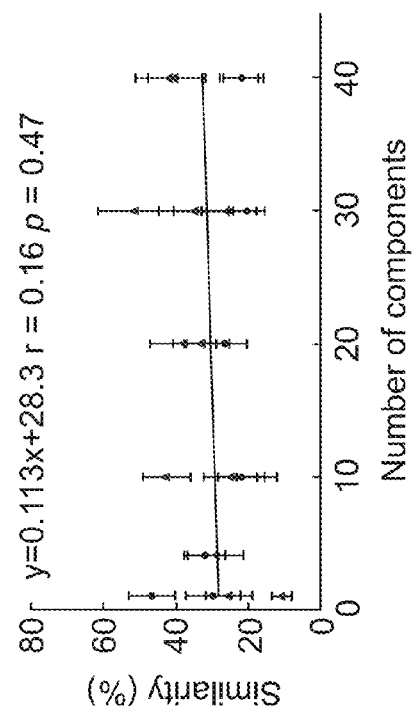

FIG. 5 is a graphical characterization of the smell of olfactory white. Ratings given to 12 monomolecular odorants (diamond), four 10-component mixtures that optimally spanned space (square), and four 40-component mixtures that optimally spanned space (triangle), along the two key axes of human olfactory perception, (A) one from very unpleasant to very pleasant, and (B) one from highly poisonous to highly edible. Error bars are standard error between subjects.

FIGS. 6A-H are graphs illustrating the rated similarity as a function of number of components in a mixture (mixture components spread in physicochemical space). A-H. The correlation of the normalized average rated similarities between 1, 4, 10, 15, 20, and 40/43-component mixtures with a non-overlapping 'target mixture' consisting of A, 43 components, B, 40 components, C, 30 components, D, 20 components, E, 15 components, F, 10 components, G, 4 components, and H, 1 component. Each point represents the average rated similarity of one pairwise comparison. These data reflect the comparisons from odorant 3 (triangle) and 4 (solid circle) of Table 1 in which the mixtures were selected according to their components' physicochemical spread. Error bars are standard error across subject ratings.

FIGS. 7A-F are graphs illustrating the rated similarity as a function of number of components in a mixture (mixture components spread in perceptual space). A-F, The correlation of the normalized average rated similarities between 1, 4, 10, 20, 30 and 40-component mixtures with a non-overlapping 'target mixture' consisting of A, 40 components, B, 30 components, C, 20 components, D, 10 components, E, 4 components, F, 1 component. Each point represents the average rated similarity of one pairwise comparison. These data reflect the comparisons from odorant sets 1 (triangle) and 2 (solid circle) of Table 1, in which the mixtures were selected according to their components' perceptual spread. Error bars are standard error across subject ratings.

Figure 8B:
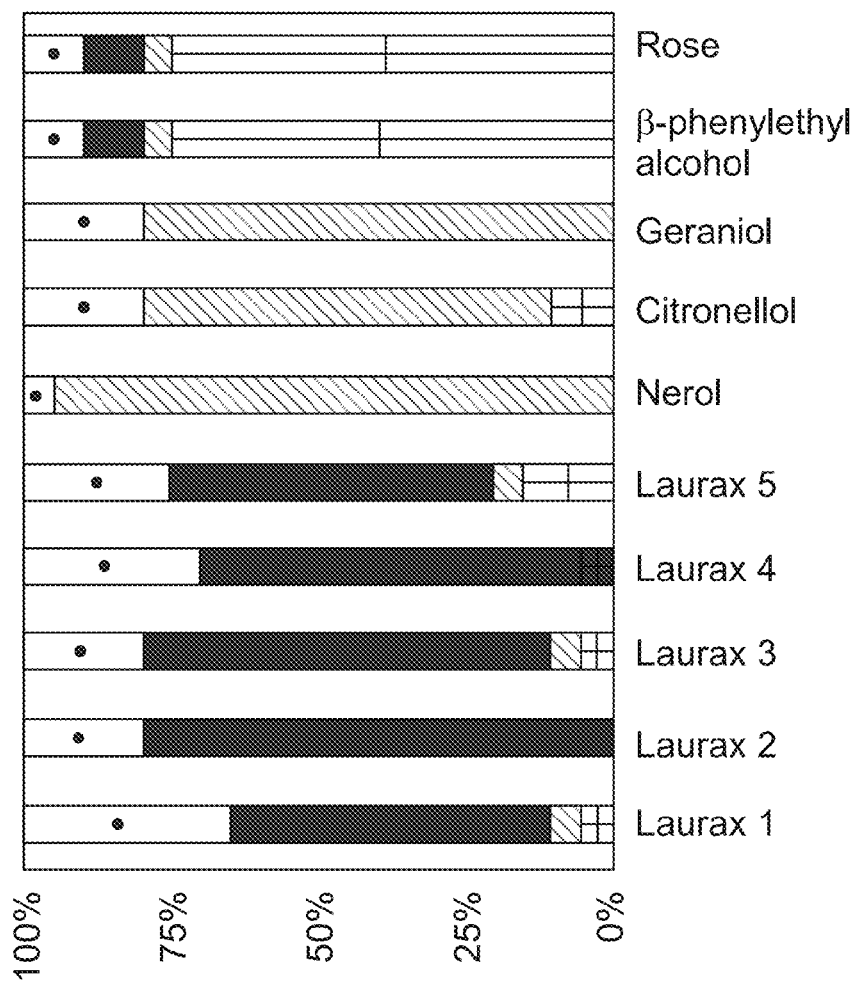

FIGS. 8A-B are graphs representing the identification of laurax after 6 months. The labels applied to (1) Five versions of Laurax, (2) β-phenylethyl alcohol, (3) Geraniol, (4) Citronellol, (5) Nerol, and (6) the rose mixture. The averaged response (in percentage) of 10 subjects in a 7-alternative (A) and 4-alternative (B) forced choice identification task.

Figure 9:
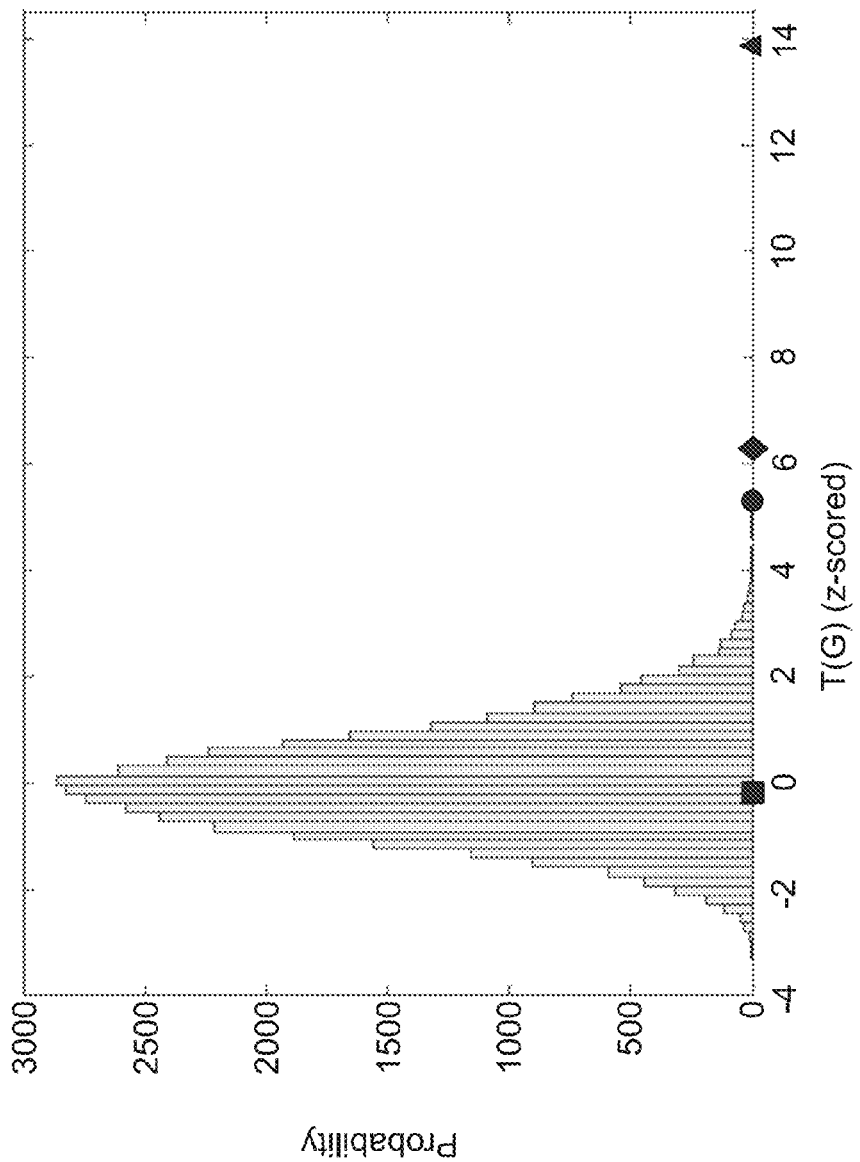

FIG. 9 is a graph illustrating natural odors form clusters in olfactory space. T(G) of Laurax (average of 40 and 60 component mixtures) (square), 63 components of rose (solid circle), 35 of coffee (diamond) (5), 37 components of an apple) (6). The present inventors ran 10,000 iterations to generate random mixtures of the appropriate component size mixtures (i.e. 60, 40, 63, 36). The histogram represents all 40,000 T(G) values (z-scored). Smaller value of T(G) represents a better spanning of the physicochemical space. As shown, whereas natural odors form an extreme cluster in this physicochemical space, Laurax reflects an average spread in this space.

DESCRIPTION OF SPECIFIC EMBODIMENTS OF THE INVENTION

The present invention, in some embodiments thereof, relates to an odorant mixture and, more particularly, but not exclusively, to an odorant mixture having an olfactory signature, and method of characterizing an odorant mixture using its olfactory signature.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The rules underlying perception of complex olfactory mixtures, remain largely unknown. On one hand, humans are very poor at identifying the components of a mixture, even when they are able to identify the components alone. In turn, humans remain exquisitely capable of discriminating one mixture from another, and mixtures containing hundreds of different volatile molecules are associated with unique olfactory percepts such as wine, roasted coffee, or rose.

While conceiving the present invention it has been hypothesized and while reducing the present invention to practice it has been realized that an odorant mixture having a plurality of odorant components which are distributed sufficiently uniformed over an olfactory space, has a generally common olfactory percept.

Thus, according to some embodiments of the present invention there is provided an odorant mixture. Optionally and preferably the odorant mixture is in gaseous state. Odorant mixture in liquid or solid states is not excluded from the scope of the present invention. In various exemplary embodiments of the invention the odorant mixture comprises N odorant components where N equals at least 10 or at least 20 or at least 30 or at least 40 or at least 50 or at least 60.

As used herein, an "odorant component" is a monomolecular substance which can be sensed by the olfactory receptors and is perceived as having a smell in humans.

Each of the odorant components is optionally and preferably characterized by a multidimensional vector of attributes. The number of attributes in the vector (namely, the dimensionality of the vector) is preferably large, e.g., at least 50 or at least 60 or at least 70 or at least 80 or at least 90 or at least 100 or at least 110 or at least 120 or at least 130 or at least 140 or at least 1000 or at least 1100 or at least 1200 or at least 1300 or at least 1400 or at least 2000 or at least 3000 or at least 4000.

While the vectors typically have large dimensionality, the dimensionality of one or more of the vectors, e.g., all the vectors, can, optionally, be reduced using a dimensionality reduction procedure. A representative example of a dimensionality reduction procedure includes, without limitation, a principal component analysis (PCA).

PCA is a known data analysis procedure. In PCA, a correlation matrix is constructed from the vectors and a set of eigenvalues of the correlation matrix can be calculated. A subset of the set of eigenvalues can then be selected. The subset is optionally and preferably of the largest eigenvalues of the correlation matrix, which typically corresponds to the most "important" dimensions of the vectors. The correlation matrix is constructed based on correlations which are calculated between different components of each data entry, and are averaged over all the data entries. The correlation matrix can be of any type, including, without limitation, an autocorrelation matrix and a covariance matrix. The correlation matrix provides a natural basis to span the space, which basis is specified by the eigenvectors of the matrix which are known as the principal components of the dataset.

The attributes of a particular odorant component can include perceptual descriptors and/or physicochemical descriptors. Perceptual descriptors can be obtained from the literature, see, for example, Dravnieks, A. Odor quality: semantically generated multi-dimensional profiles are stable. Science 218, 799-801 (1982); and Dravnieks, A. Atlas of odor character profiles (ASTM Press, PA, 1985), the contents of which are hereby incorporated by reference. A representative list of 146 perceptual descriptors descriptor names is provided in the middle column of Table 4 in the Examples section that follows.

Physicochemical descriptors can include, for example, molecular descriptors which can be obtained using a data processor supplemented with a dedicated algorithm. Alternatively, dedicated circuitry can be used. Software suitable for obtaining a vector of physicochemical descriptors according to some embodiments of the present invention includes, without limitation, the Dragon software marketed by Talete, Milan, Italy. For example, version 6 of this software can provide 4885 molecular descriptors. In experiments performed by the present inventors, the Dragon software was used to extract 1438 physicochemical descriptors for each odorant component.

Thus, the odorant mixture of the present embodiments is characterized by a collection G of N respective multidimensional vectors g (one multidimensional vector for each odorant component) and can therefore be described in terms of a multidimensional space containing this collection. This multidimensional space is referred to herein as an "olfactory space". It will be appreciated that the present embodiments contemplate more than one olfactory space. For example, when the individual odorant components are described using the 146 perceptual descriptors listed in Table 4, the olfactory space has 146 dimensions, and when the individual odorant components are described using the 1438 physicochemical descriptors, the olfactory space has 1438 dimensions.

The respective vectors of the odorant mixture are optionally and preferably distributed substantially uniformly over the olfactory space. The uniformity of the vectors can be quantified using a metric defined over the olfactory space.

Hence, in some embodiments of the present invention a database having a group K of M odorant components is accessed, and a multidimensional vector of attributes is obtained for each of the M odorant components as further detailed hereinabove. Thus, group K is characterized using a collection of M vectors, referred to herein as collection X.

Optionally and preferably, M is at least equal to N. For the purpose of the quantification, it is advantageous to employ a group K with large number of odorant components spanning over large portion of the olfactory space. Thus, in some embodiments of the present invention M equals at least 100 or at least 1000. Representative examples of groups of odorant components are provided in Tables A.1 and A.2 of Annex 1, below. The group K of the present embodiments can include at least a portion, more preferably, all the odorant components is the group listed in Table A.1 or Table A.2 of Annex 1.

For each vector x which is in the collection X but not in collection G (formally, x∈X, x∉G), a distance between x and G is calculated. Since G includes many vectors, the distance between x and G can be defined in more than one way. Typically, but not necessarily, the distance between x and G can is defined as the minimum distance that can be obtained between x and any of the vectors in G. Formally, this distance can be written as $D(x,G) = \min_{g \in G} d(x,g)$, where g is a vector in G and d(x,g) is the distance between x and g.

The distance d can be according to any metric. For example, an Euclidian distance can be calculated. Also contemplated are other metrics, including, without limitation, Minkowski metric, in which case d is a Minkowski distance.

The distance is preferably can be calculated using all the components of the vectors. In some embodiments, the distance is calculated based on a reduced dimensionality. For example, a principal component analysis can be performed, and the distance can be calculated using the one or more of the components extracted by the PCA. Typically, but not necessarily, the first p components are used, where p is an integer satisfying $p \leq 10$ or $p \leq 9$ or $p \leq 8$ or $p \leq 7$ or $p \leq 6$ or $p \leq 5$ or $p \leq 4$ or $p \leq 3$ or $p \leq 2$.

The distance D(x,G) is optionally and preferably calculated for at least some more preferably all the vectors x. The uniformity of the vectors in the collection G over the olfactory space can then be related to the average of D(x,G) over x. More specifically, denoting this average by T(G), smaller values of T(G) correspond to a more uniform distribution of the vectors in the collection G over the olfactory space, wherein higher values of T(G) correspond to large regions in odorspace where vectors in the collection G are not present.

In some embodiments of the present invention the z score of T(G) is less than 2 or less than 1.5 or less than 1 or less than 0.5 or less than 0 or less than −0.5.

A z-score of T(G) can be calculated, for example, in relation to a database of other odorant mixtures, each being characterized by an average distance T calculated over the collection X (corresponding to group K) as described above. Specifically, let $\mu_T$ and $\sigma_T$ be, respectively, the mean and standard deviation of T as calculated for the entire database. The z-score of T(G), $Z_{T(G)}$, can be calculated based on $\mu_T$ and $\sigma_T$, as known in the art, e.g., using the relation $Z_{T(G)} = (T(G) - \mu_T)/\sigma_T$.

The database is optionally and preferably a synthetic database stored on a computer readable medium. A synthetic database can include, for example, a plurality of entries, each corresponding to one database odorant mixture defined as being producible from a plurality of odorant components selected, optionally and preferably in a random manner, from the group K. Thus, each entry in the database is also characterized by a collection of vectors, one vector for each odorant component of the respective database odorant mixture. The number of vectors characterizing each database entry is referred to herein as the size of the respective entry.

Preferably, but not necessarily, the size of each entry in the database is approximately the same as the number of odorant components in the collection G. Use of database having entries with a variety of sizes is not excluded from the scope of the present invention. Typically, the number of entries in the database is at least 100 or at least 200 or at least 400 or at least 800 or at least 1600 or at least 3200 or at least 6400, e.g., about 10,000 entries or more.

The present embodiments thus provide an efficient technique for calculating, within a multidimensional space, an average distance T using the multidimensional vectors corresponding to the odorant components constituted in the odorant mixture and the multidimensional vectors corresponding to odorant components in group K but not in the odorant mixture. This average distance is characteristic to the olfactory percept and can therefore be used as, or related to, the olfactory signature of the mixture. Thus, in some embodiments of the present embodiments T(G) is defined as the olfactory signature of the mixture characterized by the collection G, and in some embodiments of the present embodiments the z-score of T(G) is defined as the olfactory signature of the mixture characterized by the collection G. Other quantities based on T(G), such as, but not limited to, the logarithm of T(G) or some normalized representation of T(G), are not excluded from the scope of the present invention for the purpose of defining the olfactory signature.

The odorant mixture of the present embodiments is thus characterized by large span and high uniformity over the olfactory space. In experiments performed by the present inventors it was found that such odorant mixture has a generally common olfactory percept. Borrowing the terminologies from color vision wherein many different wavelengths eventually generate color percept of white, and tonal audition wherein many different frequencies eventually generate white noise, the present inventors coined the term "olfactory white" for an odorant mixture having sufficiently large span and sufficiently high uniformity over the olfactory space.

The T distribution property of the present embodiments can be identified in a mixture by comparing it to a plurality of database mixtures, as shown, for example, in FIG. 9 of the Examples section that follows. An olfactory white mixture can be defined as having a T value which is from about 0.5 to about 5 standard deviations off the center of the distribution of T values for randomly selected mixtures.

Representative examples of odorant mixtures with sufficiently large span and sufficiently high uniformity over the olfactory space are provided in Tables 7A-C of the Examples section that follows.

In various exemplary embodiments of the invention the odorant components in the odorant mixture have similar odor intensity. The odor intensity can be determined by conducting olfaction tests for a group of subjects and analyzing the odor strength as perceived by the subjects. A representative example of a procedure for determining the perceived odor intensity is described in the Example section that follows.

While it is advantageous to equate the odor intensity in the odorant mixture in order to provide a generally common olfactory percept, it is to be understood that this need not necessarily be the case, since it was found by the present inventors that odorant mixture with sufficiently large span and sufficiently high uniformity over the olfactory space can have a common olfactory percept, even when not all the odorant components are present at the same odor intensity.

An odorant mixture according to some embodiments of the present invention can be used for at least partially masking a target odor in an environment. This can be done by spreading a sufficient amount of odorant mixture in the environment, to provide a combined mixture having the odorant mixture and the odorant components of the target odor. The present inventors found that when the odorant mixture has sufficiently large span and sufficiently high uniformity over the olfactory space it can provide a common olfactory percept even when combined with the odorant components of the target odor.

In some embodiments of the present invention the odorant mixture is selected such that the combined mixture has a sufficiently large span and a sufficiently high uniformity over the olfactory space. For example, the odorant mixture can be selected such that the z score of T(G*), where G* denotes the collection of vectors corresponding to the odorant components in the odorant mixture and the vectors corresponding to the odorant components in the target odor, is less than 1 or less than 0.5 or less than 0 or less than −0.5. Thus, T(G*) can be used for defining the olfactory signature of the combined odorant mixture, as further detailed hereinabove, mutatis mutandis with respect to T(G).

According to some embodiments of the present invention there is provided a method of determining an olfactory signature of an odorant mixture. Selected operations of the method described below can be executed by a data processor, such as a general purpose computer or a dedicated circuitry.

The method of the present embodiments can be embodied in many forms. For example, it can be embodied in on a tangible medium such as a computer for performing the method steps. It can be embodied on a computer readable medium, comprising computer readable instructions for carrying out the method steps. In can also be embodied in electronic device having digital computer capabilities arranged to run the computer program on the tangible medium or execute the instruction on a computer readable medium.

Computer programs implementing the method of this invention can commonly be distributed to users on a distribution medium such as, but not limited to, a floppy disk, a CD-ROM, a flash memory device. From the distribution medium, the computer programs can be copied to a hard disk or a similar intermediate storage medium. Alternatively, the computer programs can be downloaded to the hard disk or intermediate storage medium) from a server, e.g., via the internet. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The method of the present embodiments is typically useful for determining an olfactory signature of an odorant mixture having N odorant components. In some embodiments, the method receives the odorant components as input and in some embodiments of the present invention the method extracts the odorant components from the mixture itself. The extraction can be performed using any chemical analysis procedure known in the art. A representative and non-limiting example of a process suitable for extracting the odorant components from the mixture according to some embodiments of the present invention, include, without limitation, Gas Chromatography-Mass Spectrometry, which is described in many textbooks (see, for example, "GC/MS: A Practical User's Guide, 2nd Edition", 2011, by Marvin McMaster, ISBN: 978-1-1182-1005-5; "Handbook of GC/MS: Fundamentals and Applications, 2nd, Completely Revised and Updated Edition," 2008, by Hans-Joachim Hubschmann, ISBN: 978-3-527-31427-0; and also the online Wikipedia article wwwdotendotwikipediadotorg/wiki/Gas_chromatography-mass_spectrometry).

In various exemplary embodiments of the invention the method accesses a database having a group K of M odorant components. For each odorant component of the mixture and each odorant component of K, a multidimensional vector of attributes is obtained, to provide a plurality of multidimensional vectors. The multidimensional vectors corresponding to the odorant components of K can be received by the method as input. For example, the accessed database can include the multidimensional vector corresponding to each odorant component entry in the database. The multidimensional vectors corresponding to the odorant components of the odorant mixture can be calculated as further detailed hereinabove or they can be received as input from a suitable input system, such as a data processor configured to provide a multidimensional vector for a given odorant component.

The obtained multidimensional vectors are then used for calculating an average of characteristic distances between vectors corresponding to the odorant components in the mixture and vectors corresponding to the odorant components in the group K, as further detailed hereinabove. An output comprising the average is then generated. The output can include the average itself, or some related quantity such as, but not limited to, the z-score of the average, a logarithm of the average, a normalized representation of the average, etc.

When a z-score of the average is calculated, the z-score is optionally and preferably in relation to a database of other odorant mixtures. The database is optionally and preferably a synthetic database as further detailed hereinabove. The database can be stored on a computer readable medium. Alternatively, the method according to some embodiments of the present invention can generate the database. This can be done, for example, by randomly selecting sub-groups of odorant components from the group K, and defining each selected sub-group as a database odorant mixture corresponding to one database entry. The number of components in each sub-group can be the same as the number of odorant components in the collection of vectors describing the odorant mixture under analysis. Alternatively, two or more sub-groups may have different numbers of odorant components thereamongst, thereby generating a database having entries with a variety of sizes.

As stated, the average or related quantity can be used for defining the olfactory signature of the odorant mixture. Thus, the generated output according to some embodiments of the present invention includes the olfactory signature of the odorant mixture. The output can be generated by displaying the average or related quantity on a display device, printing the average or related quantity using a printer, transmitting the average or related quantity to a computer readable medium (e.g., a memory medium or a storage medium), and the like.

As used herein the term "about" or "approximately" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods 208 subjects (ages ranging from 21 to 40, no history of olfactory dysfunction, mean age 26.7±2.9, 110 women) participated in the intensity-rating (n=24), similarity scoring (n=59), discrimination (n=20), identification (n=25), delayed match-to-sample (n=60), pleasantness and edibility rating (n=20) experiments. All experiments were conducted in stainless-steel-coated odorant nonadherent rooms. All interactions with subjects during the experiments were via computer interface only. All experiments employed ~40-second inter-trial intervals, and trial order was counter-balanced across subjects. Odorant mixtures were reprepared every two days. Table 1A-D provides the recipes for the mixtures of the similarity tests.

Tables 1A-D

TABLE 1A

| Set-1 | |
|---|---|
| 7 ^ | 2 # ^ |
| 9 ^ | 3 |
| 10 # | 5 # ^ * |
| 18 * | 12 # |
| 20 # ^ * & | 13 |
| 23 # ^ | 16 # |
| 30 # | 21 # ^ * |
| 34 # ^ * | 27 # ^ |
| 37 # | 29 # ^ |
| 44 # ^ | 31 # ^ |
| 49 # ^ * | 36 # * |
| 51 | 38 # ^ * |
| 52 # ^ | 39 # * & |
| 53 ^ | 40 # ^ * |
| 54 # | 47 # ^ |
| 56 # ^ | 58 # |
| 59 # ^ * | 60 # ^ & |
| 61 | 68 # ^ |
| 63 ^ | 72 # |
| 64 # * | 81 |
| 70 # ^ * & | 82 # ^ * & |
| 71 | 93 # |
| 73 # * | 94 |
| 74 # | 95 ^ |
| 75 # | 96 # ^ |
| 76 # | 107 # ^ |
| 77 # | 109 # |
| 83 # * | 110 |
| 89 # ^ & | 111 # |
| 97 # ^ | 112 # * |
| 100 # ^ | 118 # |
| 103 | 121 # |
| 104 # | 126 # ^ |
| 113 # ^ | 132 ^ * |
| 114 # | 133 |
| 115 * | 134 # |
| 117 # ^ & | 135 # |
| 119 # ^ | 139 ^ |
| 138 # | 142 ^ |
| 141 # ^ | 143 # ^ * & |

TABLE 1B

| Set-2 | |
|---|---|
| 3 # | 2 |
| 7 | 5 # ^ |
| 9 # | 13 # |
| 10 ^ | 18 |
| 12 # | 20 |
| 16 # ^ | 21 # ^ |
| 23 # | 27 # |
| 30 # | 29 ^ |
| 31 # | 37 ^ |
| 34 # ^ * | 38 # ^ |
| 36 | 40 # |
| 39 & | 44 # |
| 47 # | 49 # |
| 58 ^ | 51 # |
| 59 # ^ * | 52 # ^ |
| 61 # ^ | 53 # ^ * |
| 64 # | 54 # |
| 68 # * | 56 # |
| 74 # ^ & | 60 * & |
| 75 # | 63 # ^ |
| 82 # ^ * & | 70 ^ * |
| 89 # ^ | 71 # |
| 94 # ^ * | 72 # ^ |
| 96 # ^ * | 73 # |
| 100 # * & | 76 # |
| 103 | 77 ^ |
| 104 # ^ | 81 ^ |
| 107 ^ | 83 # ^ |
| 109 # ^ | 93 # ^ * |
| 110 # ^ | 95 # ^ * |
| 111 * | 97 # ^ |
| 119 # | 112 ^ * & |
| 121 ^ | 113 # * |
| 126 # * | 114 # ^ * |
| 132 # ^ * | 115 # ^ * & |
| 133 # ^ | 117 # * & |
| 134 # | 118 # |
| 139 # ^ | 135 # ^ |
| 141 # ^ | 138 # |
| 142 | 143 # ^ |

TABLE 1C

| Set-3 | |
|---|---|
| 2 # ^ * | 3 # ^ |
| 10 # ^ * & | 5 |
| 16 * | 7 # ^ |
| 20 # ^ | 9 # ^ |
| 23 # | 12 # ^ * |
| 29 ^ | 13 # * & |
| 34 | 18 # |
| 36 ^ & | 21 # |
| 37 # ^ | 27 # ^ |
| 38 # ^ * | 30 # ^ |
| 39 # | 31 # * |
| 40 | 47 # ^ * |
| 44 # & | 49 |
| 51 # ^ * | 52 # ^ |
| 54 | 53 # |
| 58 # | 56 # |
| 61 # * | 59 ^ |
| 70 | 60 # |
| 72 * | 63 # |
| 75 ^ | 64 # ^ |
| 77 # ^ & | 68 & |
| 82 # ^ | 71 |
| 83 # | 73 # ^ |
| 93 # | 74 # |
| 94 # ^ * | 76 |
| 95 # | 81 |
| 97 # | 89 # ^ * & |
| 110 # ^ | 96 * |
| 111 # ^ | 100 # |
| 114 | 103 |
| 115 # ^ | 104 # ^ |
| 118 # ^ | 107 # ^ * |
| 119 # ^ * | 109 # ^ |

TABLE 1C-continued

Set-3

| | |
|---|---|
| 121 # | 112 # ^ & |
| 132 # ^ | 113 ^ * |
| 135 # | 117 # ^ |
| 138 # | 126 # * |
| 139 # ^ | 133 # ^ |
| 141 # ^ * | 134 # * |
| 143 # | 142 # ^ |

TABLE 1D

Set-4

| | |
|---|---|
| 1 # ^ $ | 2 # ^ $ |
| 5 # ^ * & | 3 ^ * |
| 9 # | 7 # ^ $ |
| 10 # $ | 12 # ^ $ * & |
| 16 # | 13 # ^ $ & |
| 18 # | 27 # ^ |
| 20 # $ | 30 # ^ |
| 21 ^ $ | 31 # $ |
| 23 # | 34 |
| 29 # $ | 49 |
| 36 # ^ | 52 # |
| 37 * | 53 # ^ |
| 38 # | 54 # |
| 39 # ^ | 56 # |
| 40 # ^ * | 60 # ^ $ |
| 44 | 63 |
| 47 # | 64 # ^ $ * |
| 50 | 68 |
| 51 ^ $ | 71 ^ |

TABLE 1D-continued

Set-4

| | |
|---|---|
| 58 # | 73 # |
| 59 ^ $ | 75 ^ |
| 61 * | 81 |
| 70 # ^ $ & | 82 # ^ |
| 72 # ^ $ * | 83 |
| 74 # ^ | 93 # $ |
| 76 # ^ * | 94 # ^ $ * |
| 77 ^ $ | 95 # |
| 89 # ^ $ | 96 |
| 97 | 100 |
| 102 # ^ | 104 # ^ $ * |
| 103 | 110 # * |
| 107 # $ | 111 # * & |
| 109 # $ | 115 # $ |
| 112 # | 118 # ^ $ |
| 113 # ^ $ * & | 119 # ^ * |
| 114 # ^ | 121 # |
| 117 # * & | 132 # $ |
| 126 * | 133 # * & |
| 127 # ^ $ | 135 |
| 131 | 138 # |
| 134 | 139 # ^ $ * |
| 140 # ^ * | 141 # ^ $ |
| 143 # ^ | 142 ^ |

The odorants selected for each mixture in the similarity experiment (odorants listed by their numbers from Dravnieks atlas). Number of components: #30; ^20; $ 15; *10; &4; Bold 1. The odors are identified by numbers according to Tables 2A-B. Set-1 and set-2, were constructed based on the perceptual space, set-3 and set-4, were selected based on the physicochemical space.

TABLE 2A

List of odorants and concentrations

| | Name | CID Number | CAS Number | v/v % or w(g)/v % | | Solvent |
|---|---|---|---|---|---|---|
| 1 | Abhexone | 61199 | 698-10-2 | 0.01 | S | water |
| 2 | Acetophenone | 7410 | 98-86-2 | 0.15 | L | mineral oil |
| 3 | ortho-Acetyl pyridine | 14286 | 1122-62-9 | 0.001 | L | 1,2-propanediol |
| 5 | ethyl 3-methyl-3-phenyl | 6501 | 77-83-8 | 1 | L | 1,2-propanediol |
| 7 | gamma-nonalactone | 7710 | 104-61-0 | 0.5 | L | mineral oil |
| 9 | iso-amyl acetate | 31276 | 123-92-2 | 0.1 | L | mineral oil |
| 10 | amyl butyrate | 10890 | 540-18-1 | 1 | L | 1,2-propanediol |
| 12 | iso-pentyl phenyl acetate | 7600 | 102-19-2 | 1 | L | mineral oil |
| 13 | pentyl valerate | 62433 | 2173-56-0 | 50 | L | 1,2-propanediol |
| 16 | Anisole | 7519 | 100-66-3 | 0.4 | L | mineral oil |
| 18 | Benzaldehyde | 240 | 100-52-7 | 0.25 | L | mineral oil |
| 20 | iso-bornyl acetate | 93009 | 5655-61-8 | 5 | L | 1,2-propanediol |
| 21 | butanoic acid | 264 | 107-92-6 | 1.2 | L | water |
| 23 | butyl sulfide | 11002 | 544-40-1 | 0.15 | L | mineral oil |
| 27 | Caryophyllene | 5281515 | 87-44-5 | 15 | L | mineral oil |
| 29 | Celeriax | 6259976 | 17369-59-4 | 0.2 | L | 1,2-propanediol |
| 30 | Chlorothymol | 6982 | 89-68-9 | saturated | S | 1,2-propanediol |
| 31 | cinnamic aldehyde | 307 | 104-55-2 | 0.01 | L | 1,2-propanediol |
| 34 | Coumarin | 323 | 91-64-5 | saturated | S | mineral oil |
| 36 | p-Cresol | 2879 | 106-44-5 | 1 | S | 1,2-propanediol |
| 37 | p-cresyl acetate | 8797 | 140-39-6 | 0.03 | L | mineral oil |
| 38 | p-cresyl-iso-butyrate | 7685 | 103-93-5 | 10 | L | mineral oil |
| 39 | 4-methyl anisole | 7731 | 104-93-8 | 0.15 | L | mineral oil |
| 40 | cuminic aldehyde | 326 | 122-03-2 | 1 | L | mineral oil |
| 44 | Cyclohexanol | 7966 | 108-93-0 | 0.4 | L | mineral oil |
| 47 | 2,4-trans-trans-decadienal | 5283349 | 25152-84-5 | 0.5 | L | mineral oil |
| 49 | dibutyl amine | 8148 | 111-92-2 | 3 | L | 1,2-propanediol |
| 50 | diethyl sulfide | 9609 | 352-93-2 | 0.01 | L | 1,2-propanediol |
| 51 | dimethyl benzyl carbinyl butyrate | 24915 | 10094-34-5 | 20 | L | 1,2-propanediol |
| 52 | dimethyl phenyl ethyl carbinol | 7632 | 103-05-9 | saturated | S | 1,2-propanediol |
| 53 | 2,3-dimethyl Pyrazine | 22201 | 5910-89-4 | 0.2 | L | 1,2-propanediol |
| 54 | 2,5-dimethyl Pyrazine | 31252 | 123-32-0 | 0.3 | L | mineral oil |
| 56 | dimethyl trisulfide | 19310 | 3658-80-8 | 0.001 | L | 1,2-propanediol |

TABLE 2A-continued

List of odorants and concentrations

| | Name | CID Number | CAS Number | v/v % or w(g)/v % | | Solvent |
|---|---|---|---|---|---|---|
| 58 | diphenyl Oxide | 7583 | 101-84-8 | 1 | S | mineral oil |
| 59 | ethyl butyrate | 7762 | 105-54-4 | 0.01 | L | mineral oil |
| 60 | ethyl propionate | 7749 | 105-37-3 | 0.25 | L | mineral oil |
| 61 | 2-ethyl pyrazine | 26331 | 13925-00-3 | 0.4 | L | mineral oil |
| 63 | Eucalyptol | 2758 | 470-82-6 | 2 | L | mineral oil |
| 64 | Eugenol | 3314 | 97-53-0 | 0.3 | L | mineral oil |
| 68 | furfuryl mercaptan | 7363 | 98-02-2 | 0.001 | L | 1,2-propanediol |
| 70 | Guaiacol | 460 | 90-05-1 | 0.25 | S | mineral oil |
| 71 | Heptanal | 8130 | 111-71-7 | 0.04 | L | mineral oil |
| 72 | 1-heptanol | 8129 | 111-70-6 | 0.4 | L | mineral oil |
| 73 | Hexanal | 6184 | 66-25-1 | 0.1 | L | 1,2-propanediol |
| 74 | hexanoic acid | 8892 | 142-62-1 | 2 | L | 1,2-propanediol |
| 75 | 1-hexanol | 8103 | 111-27-3 | 1 | L | mineral oil |
| 76 | 3-hexanol | 12178 | 623-37-0 | 0.4 | L | mineral oil |
| 77 | trans-1-Hexanal | 5281168 | 6728-26-3 | 0.1 | L | mineral oil |
| 81 | 2-phenyl propionaldehyde dimethyl acetal | 62336 | 90-87-9 | 15 | L | mineral oil |
| 82 | hydroxy Citronellal | 7888 | 107-75-5 | 50 | L | mineral oil |
| 83 | Indole | 798 | 120-72-9 | 0.5 | S | 1,2-propanediol |
| 89 | Linalool | 443158 | 126-91-0 | 2.5 | L | mineral oil |
| 93 | Melonal | 61016 | 106-72-9 | 1 | L | mineral oil |
| 94 | l-menthol | 16666 | 2216-51-5 | 3.5 | S | 1,2-propanediol |
| 95 | 2-methoxy naphthalene | 7119 | 93-04-9 | saturated | S | mineral oil |
| 96 | methyl anthranilate | 8635 | 134-20-3 | 0.35 | L | mineral oil |
| 97 | methyl acetaldehyde dimethyl acetal | 20859 | 462-95-3 | 0.15 | L | 1,2-propanediol |
| 100 | para-methyl quinoline | 7059 | 91-62-3 | 0.25 | L | 1,2-propanediol |
| 102 | methyl salicylate | 4133 | 119-36-8 | 0.25 | L | mineral oil |
| 103 | S-(methyl thio) butyrate | 62444 | 2432-51-1 | 0.03 | L | mineral oil |
| 104 | musk galaxolide | 91497 | 1222-05-5 | 5 | L | 1,2-propanediol |
| 107 | nonyl acetate | 8918 | 143-13-5 | 25 | L | mineral oil |
| 109 | 1-octanol | 957 | 111-87-5 | 0.75 | L | mineral oil |
| 110 | 1-octen 3-ol | 18827 | 3391-86-4 | 0.04 | L | mineral oil |
| 111 | pentanoic acid | 7991 | 109-52-4 | 0.1 | L | mineral oil |
| 112 | 4-Pentenoic acid | 61138 | 591-80-0 | 0.3 | L | mineral oil |
| 113 | Phenyl acetic acid | 999 | 103-82-2 | 10 | S | mineral oil |
| 114 | phenyl acetylene | 10821 | 536-74-3 | 0.3 | L | mineral oil |
| 115 | phenyl Ethanol | 6054 | 60-12-8 | 50 | L | mineral oil |
| 117 | iso-phorone | 6544 | 78-59-1 | 3 | L | mineral oil |
| 118 | alpha-pinene | 6654 | 80-56-8 | 15 | L | mineral oil |
| 119 | propyl butyrate | 7770 | 105-66-8 | 1.3 | L | mineral oil |
| 121 | Propyl sulfide | 8118 | 111-47-7 | 0.1 | L | mineral oil |
| 126 | Skatole | 6736 | 83-34-1 | 0.005 | S | 1,2-propanediol |
| 127 | α-Terpineol | 17100 | 10482-56-1 | 10 | S | 1,2-propanediol |
| 131 | thioglycolic acid | 31277 | 123-93-3 | 10 | S | water |
| 132 | Thiophene | 8030 | 110-02-1 | 2.5 | L | mineral oil |
| 133 | Thymol | 6989 | 89-83-8 | 13 | S | 1,2-propanediol |
| 134 | ortho-tolualdehyde | 10722 | 529-20-4 | 0.1 | L | mineral oil |
| 135 | Toluene | 1140 | 108-88-3 | 3 | L | mineral oil |
| 138 | gamma-undecalactone | 7714 | 104-67-6 | 10 | L | mineral oil |
| 139 | undecylenic acid | 5634 | 112-38-9 | 13 | S | 1,2-propanediol |
| 140 | iso-valeraldehyde | 11552 | 590-86-3 | 0.0003 | L | mineral oil |
| 141 | iso-valeric acid | 10430 | 503-74-2 | 0.01 | L | mineral oil |
| 142 | gamma-valerolactone | 7921 | 108-29-2 | 0.2 | L | 1,2-propanediol |
| 143 | Vanillin | 1183 | 121-33-5 | 5 | S | mineral oil |

On the first column are the ordinal numbers from *Dravnieks' Atlas of Odor Character Profiles*[1, 2]; On the six column odorants' phase: L = liquid, S = solid.

TABLE 2B

List of 58 additional odorants and concentrations

| Name | CID Number | CAS Number | v/v % or w/v % | | Solvent |
|---|---|---|---|---|---|
| acetic acid | 176 | 64-19-7 | 10 | L | water |
| Acetaldehyde | 177 | 75-07-0 | 5 | L | water |
| 3-hydroxybutan-2-one | 179 | 513-86-0 | 1.1 | S | 1,2-propanediol |
| propan-2-one | 180 | 67-64-1 | 25 | L | water |
| Butanal | 261 | 123-72-8 | 0.002 | L | water |
| Octanal | 454 | 124-13-0 | 0.25 | L | mineral oil |
| 2-hydroxypropanoic acid | 612 | 50-21-5 | 100 | L | |
| butane-2,3-dione | 650 | 431-03-8 | 0.5 | L | 1,2-propanediol |

TABLE 2B-continued

List of 58 additional odorants and concentrations

| Name | CID Number | CAS Number | v/v % or w/v % | | Solvent |
|---|---|---|---|---|---|
| propan-1-ol | 1031 | 71-23-8 | 15 | L | water |
| 2-oxopropanoic acid | 1060 | 127-17-3 | 0.8 | L | water |
| methylsulfanylmethane | 1068 | 75-18-3 | 0.004 | L | water |
| decanoic acid | 2969 | 334-48-5 | 100 | S | 1,2-propanediol |
| propan-2-ol | 3776 | 67-63-0 | 100 | L | |
| 2-methylpropanal | 6561 | 78-84-2 | 0.025 | L | 1,2-propanediol |
| butan-2-one | 6569 | 78-93-3 | 1.5 | L | 1,2-propanediol |
| methyl acetate | 6584 | 79-50-9 | 7.5 | L | water |
| 2-methylpropanoic acid | 6590 | 79-31-2 | 1.25 | L | 1,2-propanediol |
| methyl benzoate | 7150 | 93-58-3 | 0.5 | L | 1,2-propanediol |
| ethyl benzoate | 7165 | 93-89-0 | 0.005 | L | 1,2-propanediol |
| ethyl 2-hydroxypropanoate | 7344 | 97-64-3 | 20 | L | 1,2-propanediol |
| 2-methyl-5-propan-2-ylcyclohexa-1,3-diene | 7460 | 99-83-2 | 0.5 | L | mineral oil |
| 1-methyl-4-propan-2-ylbenzene | 7463 | 99-87-6 | 0.5 | L | 1,2-propanediol |
| 2-phenylethyl acetate | 7654 | 103-45-7 | 100 | L | |
| (3S)-3,7-dimethyloct-6-en-1-ol | 7793 | 7540-51-4 | 1 | L | 1,2-propanediol |
| ethyl octanoate | 7799 | 106-32-1 | 1 | L | 1,2-propanediol |
| propane-1-thiol | 7848 | 107-03-9 | 0.0005 | L | 1,2-propanediol |
| ethyl formate | 8025 | 109-94-4 | 8.33 | L | 1,2-propanediol |
| ethyl decanoate | 8048 | 110-38-3 | 100 | L | |
| heptan-2-one | 8051 | 110-43-0 | 0.33 | L | 1,2-propanediol |
| methyl octanoate | 8091 | 111-11-5 | 3.5 | L | 1,2-propanediol |
| Undecanal | 8186 | 112-44-7 | 0.2 | L | 1,2-propanediol |
| ethyl acetate | 8857 | 141-78-6 | 3 | L | 1,2-propanediol |
| 4-methylpent-3-en-2-one | 8858 | 141-79-7 | 1 | L | 1,2-propanediol |
| butane-2-thiol | 10560 | 513-53-1 | 0.0005 | L | 1,2-propanediol |
| ethyl pentanoate | 10882 | 539-82-2 | 0.025 | L | 1,2-propanediol |
| heptan-2-ol | 10976 | 543-49-7 | 5 | L | 1,2-propanediol |
| methyl propanoate | 11124 | 554-12-1 | 2.5 | L | 1,2-propanediol |
| hexan-3-one | 11509 | 589-38-8 | 0.5 | L | 1,2-propanediol |
| pent-1-en-3-ol | 12020 | 616-25-1 | 0.3 | L | 1,2-propanediol |
| methyl butanoate | 12180 | 623-42-7 | 0.15 | L | 1,2-propanediol |
| (methyldisulfanyl)methane | 12232 | 624-92-0 | 0.025 | L | 1,2-propanediol |
| pentyl acetate | 12348 | 628-63-7 | 0.75 | L | 1,2-propanediol |
| nonan-2-ol | 12367 | 628-99-9 | 1 | L | 1,2-propanediol |
| decan-2-one | 12741 | 693-54-9 | 100 | L | |
| bis(methylsulfanyl)methane | 15380 | 1618-26-4 | 0.002 | L | 1,2-propanediol |
| pentan-2-ol | 22386 | 6032-29-7 | 4 | L | 1,2-propanediol |
| hexyl hexanoate | 22873 | 6378-65-0 | 26.66 | L | 1,2-propanediol |
| 4-methoxybenzaldehyde | 31244 | 123-11-5 | 3.3 | L | 1,2-propanediol |
| diethyl butanedioate | 31249 | 123-25-1 | 100 | L | |
| ethyl hexanoate | 31265 | 123-66-0 | 0.5 | L | 1,2-propanediol |
| butyl acetate | 31272 | 123-86-4 | 1 | L | 1,2-propanediol |
| 4-ethyl guaiacol | 62465 | 2785-89-9 | 0.1 | L | 1,2-propanediol |
| (R)-(+)-beta-citronellol | 101977 | 1117-61-9 | 100 | L | |
| Limonene | 440917 | 5989-27-5 | 5 | L | mineral oil |
| laevo-beta-pinene | 440967 | 18172-67-3 | 10 | L | 1,2-propanediol |
| Geraniol | 637566 | 106-24-1 | 50% | L | 1,2-propanediol |
| Thiolane | 1127 | 110-01-1 | 0.0005 | L | 1,2-propanediol |
| trimethyl amine | 1146 | 75-50-3 | 0.025 | L | water |

Equated-Intensity Odorants:

All odorants were purchased from Aldrich Chemicals (St. Louis, Mo.) in the highest available purity. All odorants were diluted with either mineral oil, 1,2-propanediol or deionized distilled water to a point of approximately equally perceived intensity. This perceived-intensity equation was conducted according to previously published methods (Khan et al., 2007, *The Journal of Neuroscience* 27, 10015 (2007)). In brief, the present inventors identified the odorant with lowest perceived intensity, and first diluted all others to equal perceived intensity as estimated by experienced lab members. Next, 24 naïve subjects (10 females) smelled the odorants and rated their intensity. The present inventors then further diluted any odorant that was 2 or more standard deviations away from the mean intensity of the series, and repeated the process until we had no outliers. This process is suboptimal, but considering the natural variability in intensity perception, together with naive subjects' bias to identify "a difference", and the iterative nature of this procedure, any stricter criteria would generate an endless process.

The odorants used and their final dilutions are listed in Tables 2A-B.

Selecting Components for Mixtures in the Similarity Experiments:

The present inventors selected mixtures of odorants out of the initial pool of odorants in a pseudo-random manner, which were applied to two separate databases. The first database consists of 138 odorants, each having 146 perceptual descriptors in the Dravnieks' atlas (Dravnieks, A. *Atlas of odor character profiles* (ASTM Press, PA, 1985); Dravnieks, A. Odor quality: semantically generated multidimensional profiles are stable. *Science* 218, 799-801 (1982)), and this database is referred to as the "odor perceptual space". The second database contains 1492 odorants commonly used in olfaction research (Khan, R. M., et al. Predicting odor pleasantness from odorant structure: pleasantness as a reflection of the physical world. The Journal of Neuroscience 27, 10015 (2007)). For each of the 1492 odorants the present inventors obtained 1438 physicochemical descriptors using Dragon software (Talete, Milan, Italy) (Todeschini, R. & Consonni, V. Molecular descriptors for chemoinformatics (Vch Pub, 2009).

The values of the 1438 physicochemical descriptors are on vastly different scales. Thus, to eliminate this source of variance, the values of each property were z-scored. This data is referred to herein as the "odor physiochemical space". Each odorant was represented by a vector whose coordinates describe its 146 perceptual or 1438 physicochemical properties. The selection process of the different mixture sizes from the present collection of odorants was as follows: the distance between an odorant x and a mixture G was defined as the minimum Euclidean distance between the odorant vector and the vector of one of the mixture's components: $D(x,G) = \min_{g \in G} d(x,g)$ where $d(x,g)$ is the Euclidean distance between the vectors x and g. For example, if the coordinates of the odorants in a mixture $G=\{g:g \in G\}$ of a hypothetical database were ([4,−6,8],[3,−3,10],[−4,0,3]), then the distance of an odorant x with coordinates [−2,1,1] to that mixture would be 3, because that is the distance to the closest point: [−4,0,3]. Next, the present inventors defined a measure T(G) of how well a collection of odorants is spread out over the database of odorants. T(G) is the average distance between the mixture and all of the odorants in the database (138 in the perceptual space and 1492 in the physicochemical space):

$$T(G) = \frac{\sum D(x, G)}{|X|}$$

The present experiment required that two disjoint collections of 40 odorants were found, which are well distributed over the database. From a pool of 80 odorants (picked randomly out of the 86), 10,000 random samples of 40 were selected, and for each sample G, $T(G)+T(G^C)$ was calculated, where $G^C$ represents the complementary set of G. The present inventors selected the collection G which gave the lowest sum of $T(G)+T(G^C)$ and labeled it 40A and its complement $G^C$ as 40B. Next, the present inventors another 10,000 samples of 30 odorants out of 40A and picked the one sample G such that T(G) was minimal and labeled it 30A. In a similar manner 20A, 10A, and 4A were picked. 1A was picked randomly out of the odorants in 40A. The procedure was repeated to create the subsets 30B, 20B, 10B, 4B, and 1B, out of 40B. The mixtures described above constitute one set that was used to conduct an experiment with a group of ~14 subjects. A total of four different sets of mixtures were prepared using this semi random process, each created for a separate experiment. Two of the sets, which will be referred to as set-1 and set-2, were constructed based on the perceptual space (138 vectors with 146 coefficients). The two other sets, set-3 and set-4, were selected based on the physicochemical space (1492 vectors with 1438 coefficients). In set-4, the largest mixture was composed of 43 components rather than 40, out of the full pool of 86 odorants, and the resulting mixture sizes in this set were 43, 30, 20, 15, 10, 4 and 1.

Pairwise Similarity Tests:

In each experiment, each subject was presented with 48 comparisons of mixtures and was asked to rate their similarity on a visual-analogue scale ranging from 1 to 9, with 9 being the most similar. In total, there were 191 pairwise similarity comparisons, 147 of which were between non-overlapping mixtures and the remaining 44 were comparisons of mixtures to themselves. Each subject repeated the experiment on two different days to assess test-retest reliability. The ratings by subjects whose similarity ratings for identical mixtures were poorer by at least 2 standard deviations from the mean were discarded. This amounted to 3 subjects, retaining in the analysis: 12, 13, 13 and 18 subjects for each experiment. The average rated similarities were calculated across subjects.

Three-Alternative Forced-Choice Discrimination Test:

Twenty subjects (10 females) were presented with odorant triplets. Two of the jars in each triplet contained an identical 35-component mixture (4 versions across experiments), and the third jar contained a different non-overlapping mixture of various component sizes which span the perceptual space (2, 3, 4, 5, 7, 8, 10, 14, 15, 17, 20, 25, and 30 components). The subjects were asked to pick out the jar that contained the dissimilar mixture and rate their confidence level on a scale of 1 to 5, with 5 corresponding to most certain. The subjects were enabled to smell each of the three jars twice. Each subject repeated the experiment on two different days to assess test-retest reliability. Correct discrimination scored 1 and incorrect discrimination scored 0. The scores for each mixture component number were averaged across the four versions (FIG. 2B). The confidence level ratings of subjects who answered correctly in less than 70% of the discrimination trials were discarded, retaining 16 subjects for this analysis. The results were normalized to a scale of 0 to 100 (FIG. 2C), with 100 corresponding to most certain.

Identification Experiments:

The mixtures were selected to span the physicochemical space. After a two-day acquaintance with 40-component Laurax, 12 subjects performed a four-alternative forced-choice identification task for 23 different novel target odorant mixtures ranging from 1, 4, 10, 20, 30, to 40 components, all selected to span physicochemical space. Subjects were asked to choose the most appropriate label for each mixture out of four options; one being Laurax, and the other three were labels provided by a perfumer. In the second experiment, 13 different subjects had to choose the appropriate label for the same mixtures out of five options, four the same as the above, and the fifth option was "other". Choosing Laurax scored 1 and choosing any of the other names scored 0. The number of times Laurax was chosen was averaged across four versions of each number of components in a mixture (three versions in the case of 40 component mixture). Two out of the 25 subjects were excluded because they did not identify the very same mixture they smelled in the two previous days as Laurax. Thus, the number of subjects for further analysis was 11 and 12, respectively.

Delayed Match-to-Sample:

After two-day acquaintance with 30-component Laurax, 12 subjects smelled 21 target mixtures of various component numbers (30, 25, 20, 15, 10, 5 and 1), which were selected out of the remaining 56 odorants. In other words, those mixtures shared no components in common with the Laurax mixture. Subjects were asked to decide if the smell of each jar was Laurax, by pressing 'Yes' or 'No'. All subjects correctly identified Laurax as Laurax in all 6 repetitions, with the exception of one subject who correctly identified it in 4 of 6 repetitions.

In the second delayed match-to-sample test, after a two-day acquaintance with the 25-component Laurax mixture, 16 subjects smelled 17 target mixtures from a pool of 144 single molecules: nine mixtures whose components spanned physicochemical space, five mixtures whose components were clustered in this space, and two mixtures that had the same components as the Laurax they learned, however, one single molecule provided 50% of the total mixture solution volume: in the first mixture this molecule was isopropyl alcohol (67-63-0) and in the second mixture, this molecule was ethyl butyrate (105-54-4).

Subjects were asked to answer whether the odor was Laurax using a VAS ranging between "yes" and "no". The present inventors considered answers above 75% as yes, and below 25% as no.

The same paradigm and analysis were used in the two final delayed match-to-sample tasks using mixtures of 15 (18 subjects) and 60 (14 subjects) components (Table 4: 60A). Two subjects were excluded from further analysis, one did not identify the very same mixture smelled in the two previous days as Laurax, and the second subject did not use the VAS scale.

Example 1

Mixtures with Many Equal-Intensity Spanned Components Begin to Smell the Same 86 monomolecular odorants were obtained that were well distributed in both perceptual (1, 11-13) (FIG. 1A) and physicochemical (1, 14, 15) (FIG. 1B) stimulus space. Each of these odorants were diluted separately to a point of about equal perceived intensity as estimated by an independent group of 24 subjects (Table 2A, herein above), and various odorant mixtures containing various numbers of such equal-intensity odorant components were prepared. Importantly, to prevent formation of novel compounds, odorant mixtures were not mixed in the liquid phase, but rather each component was dripped onto a common absorbing pad in a sniff-jar, such that their vapors alone mixed in the jar headspace. To select the components of each mixture, an algorithm was used that automatically identified combinations of molecules spread out in olfactory stimulus space. Several different versions for each mixture size were prepared containing 1, 4, 10, 15, 20, 30, or 40/43 components, such that half of the versions were optimally spread in perceptual space, and half of the versions were optimally spread in physicochemical space.

Pairwise similarity tests (using a 9-point visual analogue scale; VAS) of 191 mixture pairs, in 56 subjects (average of 14 subjects per comparison) were performed. Each target mixture (1, 4, 10, 15, 20, 30, or 40/43 components) was compared to all other mixtures (1, 4, 10, 15, 20, 30, or 40/43 components), and as a control, to itself. Other than comparisons of a mixture to itself, all comparisons were non-overlapping, i.e. each pair of mixtures under comparison shared no components in common.

Consistent with the present hypothesis, there was a significant relation between the number of components in each of two mixtures and their perceived similarity, in both perceptual ($F(1,17)=124.8$, $p<0.0001$) and physicochemical ($F(1,28)=34.1$, $p<0.0001$) space, reflecting increased similarity with increased number of components ($r=0.94$ in perceptual space and $r=0.75$ in physicochemical space (both $p<0.0001$)) (FIG. 2A). Looking at each target mixture size independently revealed that this was consistently true for target mixtures of 20 or more components (correlation between number of components and similarity score, all $r>0.58$, all $p<0.03$, FIGS. 6A-D, FIGS. 7A-C), but not for target mixtures of fewer than 10 components (all $r<0.18$, all $p>0.45$, FIGS. 6F-H, FIGS. 7E-F). In other words, the more components in each of two mixtures, the more similar smelling those two mixtures became, despite sharing no components in common (FIG. 2A). This trend implies that if more and more nonoverlapping components are added to each of two mixtures, these two mixtures should eventually smell the same, despite sharing no components in common. Indeed, given a sufficient number of equal-intensity spanned components, this implies that all mixtures should eventually smell the same. This predicted ultimate point of perceptual convergence is referred to herein as olfactory white.

In order to ascertain whether the ~30-component mixtures tested could be referred to as olfactory white, the present inventors conducted a discrimination experiment. Twenty subjects performed a three-alternative forced-choice discrimination task between a grand mixture made of 35 components and non-overlapping component mixtures of various sizes. Even when selecting the mixtures spread in perceptual space, the mixtures remained discernible. Although as the number of components increased discrimination accuracy decreased (Kendall Correlation (KC), Tau=-0.51, Z=2.13, $p<0.04$. FIG. 2B), as did self-rated confidence in the discrimination (KC, Tau=-0.76, Z=3.4, $p<0.001$. FIG. 2C), discrimination accuracy for even 30-component mixtures remained well above chance.

Example 2

Mixtures with Many Equal-Intensity Spanned Components are Identified as Olfactory White Using vision, humans can easily discriminate between many different "whites", yet they all retain the color-gestalt identity of white. To determine whether odorant mixtures of ~30 spanned components similarly obtain a gestalt identity, an odor identification experiment was conducted. Selecting from physicochemical space, four versions of 40-component mixtures were generated. In order to prevent any cognitive influences of the label white, these mixtures were labeled with the meaningless name Laurax. Each of the four versions of Laurax was assigned to three different subjects from a group of 12. To acquaint themselves with the odor, each subject came to lab on three consecutive days, and every day repeatedly smelled and rated the applicability of 146 verbal descriptors (16) to their version of Laurax only. On the fourth day, test day, subjects performed a four-alternative forced-choice identification task for 23 different novel yet partially overlapping target odorant mixtures, ranging from 1,4,10,20,30, to 40-components, all selected to span physicochemical space. Each target mixture was provided with four alternative labels: Three labels were assigned by an expert perfumer (who was blind to experimental aims and conditions) as optimal identifiers for each mixture (Table 3, hereinbelow), and the fourth label was Laurax.

TABLE 3

Three perfumer-provided names for each of the mixtures

|  | 40 Version I | 40 Version II | 40 Version III | 40 Version IV |
|---|---|---|---|---|
| First experiment | Thyme<br>Vanilla -Cinnamon<br>Coconut | Cherry Candy<br>Vanilla Butter<br>Cinnamon | Vanilla Butter<br>Animalistic<br>Urine | Cherry Candy<br>Vanilla Butter<br>Cinnamon |
| Second experiment | Oregano<br>Cinnamon<br>Cherry Candy | Red fruit<br>Vanilla baking<br>Cinnamon Tea | Vanilla baking<br>Cinnamon Tea<br>Butter | Cinnamon<br>Nutty<br>Butter |

|  | 30 Version I | 30 Version II | 30 Version III | 30 Version IV |
|---|---|---|---|---|
| First experiment | Jasmine<br>Red fruit<br>Vinegar | Beurre noisette<br>Cinnamon stick<br>Vanilla | Bengay<br>Thyme<br>Vanilla Butter | Cherry Candy<br>Feces<br>Urine |
| Second experiment | Air freshener<br>Green Apple<br>Cinnamon | Vanilla baking<br>Coffee<br>Nutty | Oregano<br>Cinnamon<br>Butter | Cherry Candy<br>Nutty<br>Vanilla baking |

|  | 20 Version I | 20 Version II | 20 Version III | 20 Version IV |
|---|---|---|---|---|
| First experiment | Jasmine<br>Lily of the Valleys<br>Water vapor | Patchouli -<br>Vanilla<br>Coconut<br>Butter | Cat feces<br>Jasmine<br>Animalistic | Patchouli -<br>Vanilla<br>Cinnamon<br>Urine/Feces |
| Second experiment | Nutty<br>Vanilla baking<br>Butter | Nutty<br>Seasoned- Sweet<br>Butter | Ink<br>Cat urine<br>Cinnamon | Cinnamon<br>Apple<br>Feces |

|  | 10 Version I | 10 Version II | 10 Version III | 10 Version IV |
|---|---|---|---|---|
| First experiment | Cat urine<br>Feces<br>Oregano | Talc Cream<br>Baby smell<br>Urine | Oregano<br>Vinegar<br>butter | Naphthalene<br>Jasmine<br>Rose water |
| Second experiment | Oregano<br>Urine/Feces<br>Rotten eggs | Fruity<br>Flowery<br>Butter | peppermint<br>Oregano<br>Feces | Naphthalene<br>Feces/Cat urine<br>Vinegar |

|  | 4 Version I | 4 Version II | 4 Version III | 4 Version IV |
|---|---|---|---|---|
| First experiment | Oregano<br>Pizza<br>Cat urine | Feces<br>Cat urine<br>Wild cat/Street cat | Banana<br>Cat urine<br>Feces | Oregano Pizza<br>Butter<br>Vinegar |
| Second experiment | Weedy<br>Seasoned<br>Peppermint | Diluted Tomato paste<br>Fruity<br>Sour | Cider<br>Cherry Candy<br>Banana | Thyme<br>Oregano<br>Pizza Sauce |

|  | 1 Version I | 1 Version II | 1 Version III | 1 Version IV |
|---|---|---|---|---|
| First experiment | Coconut<br>Bitter almond<br>Butter | Naphthalene<br>*Narcissus*<br>Jasmine | Banana<br>Pear Nectar<br>Cherry Candy | Rose water<br>Blancmange<br>Sweet almond |
| Second experiment | Coconut<br>Fruity<br>Creamy | Flowery<br>naphthalene<br>medicinal | Banana<br>Green Apple<br>Cherry candy | Rose water<br>Pine needles<br>Green Root |

It was found that the probability of assigning the name Laurax to a novel mixture increased as the number of components increased (KC, Tau=0.73, Z=2.1 p<0.04) (FIG. 3A). Moreover, novel target mixtures with less than 20 components were significantly less likely to be identified as Laurax than novel targets of 20 components or more (t(10)= 5.54, p<0.001. FIG. 3A inset). Finally, whereas chance application of a label in the four-alternative task is 25%, the label Laurax was applied to novel 40-component mixtures 57.6% of the time (t(10)=3, p<0.02).

The above-used descriptors for Laurax, although provided by a professional perfumer, may nevertheless lack universal applicability. To address the possibility of "dumping" (17), namely assignment of inappropriate labels in the face of limited alternatives, the experiment was repeated with a new group of 13 subjects, and the additional response option of 'other'. Again, the probability of assigning the name Laurax increased as the number of components increased (KC, Tau=0.93, Z=2.6, p<0.01) (FIG. 3B), and novel target mixtures with less than 20 components were significantly less likely to be identified as Laurax than novel targets of 20 components or more (t(11)=5.68, p<0.001. FIG. 3B inset). Finally, whereas chance application of a label in the five-alternative task is 20%, the label Laurax was applied to novel 40-component mixtures 50% of the time (t(11)=3.35, p<0.007).

Because the present inventors were limited by the available components for which they had equated intensity, yet wanted to have meaningful differences across the various target mixtures, in the two above experiments there was inevitable minimal component overlap between the learned Laurax and target mixtures. Moreover, despite the addition of "other" as a viable response, "dumping" remains possible. With these considerations in mind, in the following experiments an even stricter test was applied:

After two-day acquaintance with 30-component Laurax, 12 subjects smelled 21 target mixtures of various component numbers, yet with zero component overlap to the Laurax they learned, and judged whether these mixtures were, or were not Laurax, i.e., no alternative labels were provided in this delayed match-to-sample task.

Consistent with the previous experiments, the probability of discriminating a mixture from the Laurax they learned decreased as the number of components increased (KC Tau=−0.67, Z=2.12, p<0.04. FIG. 4A), and novel target mixtures with less than 20 components were significantly more likely to be discriminated from Laurax than novel targets of 20 components or more (t(11)=3.49, p<0.006. FIG. 4A inset).

Moreover, chance in this task is 50%. Whereas subjects could easily discriminate smaller novel mixtures from the Laurax they learned (1, 5, 10, 15 components mixtures, all t>3.73, all p<0.005), they could not discriminate novel 30-component mixtures from the Laurax they learned (32.3%±33.7, t(11)=1.81, p>0.1). It is important to acknowledge the perceptual memory component in the delayed match-to-sample task. Had subjects been simultaneously provided with the Laurax they previously learned and the novel 30-component mixtures, they would likely discriminate them (as in FIG. 2B). However, given the gestalt percept of the Laurax they learned alone (which was indeed sufficient for 97% identification of the Laurax they learned), novel 30-component mixtures were deemed not significantly different from Laurax.

One may raise the possibility that Laurax became a percept associated with "large mixtures", regardless of the mixtures' olfactory identity. To test this, the present inventors repeated the above strict delayed match-to-sample task in an additional 16 subjects, yet as test targets used only 25-component mixtures, nine versions that spanned physicochemical space, five versions that were clustered in physicochemical space, and two versions that were identical to the Laurax they learned, but components were not equated for perceived intensity. Because 86 molecules that span space were initially selected, now in order to generate 25-component clusters, the present inventors were forced to equate perceived intensity of an additional 58 molecules, such that they obtained a pool of 144 molecules to choose from (Table 2B, herein above). Moreover, to allow a distribution of results, rather than a yes-no selection, the present inventors asked subjects whether the odor was Laurax, and provided participants with a VAS ranging between "yes" and "no". Answers above 75% were considered as yes, and below 25% as no. Novel clustered mixtures were more discernible from Laurax than novel spanned mixtures (clustered=67.5%±32.56 vs. spanned=42.36%±32.77: t(15) =2.89, p<0.02) (FIG. 4B), and the Laurax not equated for intensity was discernible from Laurax itself (because there is only one version of Laurax itself, here the exact binomial test was used, p<0.0002) (FIG. 4B). Thus, the percept of Laurax was more dependent on spanning olfactory space than on equating intensity. Moreover, it should be stressed that the true influence of spanning olfactory space and equating intensity is likely much greater than the significant interaction revealed here. That is because the possibility of selecting independent clusters sized 25 out of the 144 molecules for which intensity was equated remains limited. Thus the "clusters" were nevertheless quite spanned.

Thus, this result, although significant in of itself (p<0.02), likely underestimated the power of the manipulations.

Finally, to again verify the limits of this phenomenon, the present inventors repeated the delayed match-to-sample task in 18 additional subjects, testing mixtures of up to 15 components only, i.e., mixtures that on average should not converge. Here, 15-component clusters and 15-component spreads did not significantly differ from each other (t(17) =0.33, p=0.74), and both differed from the stored representation of the Laurax they learned (both p<0.001). In turn, the delayed match-to: sample task was repeated in 14 additional subjects, testing mixtures of up to 60 components, and similar results were obtained to those with 30 components, whereby participants could not discriminate novel 60-component mixtures from the stored representation of the 60-component Laurax they learned (exact binomial test, p>0.43). Taken together, the above experiments are consistent with the notion of a gestalt percept following combinations of ~30 equal-intensity components or more that are well distributed in physicochemical space. This percept is referred to herein as olfactory white.

Example 3

Olfactory White Smells Intermediately Pleasant and Edible

The present dilution procedure, whereby all components were equated in magnitude with the least-intense component, rendered mixtures of overall low intensity. In other words, olfactory white was in no way overwhelming. But how did it smell? Perhaps tellingly, the descriptors of white provided by the professional perfumer were quite variable.

This can be taken to imply that white doesn't smell like any common object in particular. To provide a better notion of what olfactory white does smells like, the present inventors summarized the applicability of 146 verbal descriptors provided by the 85 subjects who smelled white repeatedly throughout all experiments (Table 4, hereinbelow).

TABLE 4

Verbal descriptors of White

| | Descriptors | P.A. |
|---|---|---|
| 1 | Fruity, citrus | 56.2 |
| 2 | Lemon | 45.9 |
| 3 | Grapefruit | 40.4 |
| 4 | Orange | 39.5 |
| 5 | Fruity, other than citrus | 53.7 |
| 6 | Pineapple | 34.3 |
| 7 | Grape juice | 30.7 |
| 8 | Strawberry | 21.1 |
| 9 | Apple | 27.5 |
| 10 | Pear | 28.8 |
| 11 | Melon | 30.7 |
| 12 | Peach | 28.3 |
| 13 | Banana | 19.0 |
| 14 | Floral | 62.1 |
| 15 | Rose | 43.2 |
| 16 | Violets | 24.8 |
| 17 | Lavender | 39.9 |
| 18 | Cologne | 40.1 |
| 19 | Musky | 45.5 |
| 20 | Perfumery | 63.6 |
| 21 | Fragrant | 72.9 |
| 22 | Aromatic | 62.3 |
| 23 | Honey | 26.4 |
| 24 | Cherry | 24.3 |
| 25 | Almond | 19.4 |
| 26 | Nail polish remover | 37.2 |
| 27 | Nutty | 19.3 |
| 28 | Spicy | 15.0 |
| 29 | Clove | 23.6 |
| 30 | Cinnamon | 24.1 |
| 31 | Laurel leaves | 18.6 |

TABLE 4-continued

Verbal descriptors of White

| | Descriptors | P.A. |
|---|---|---|
| 32 | Tea leaves | 23.9 |
| 33 | Seasoning (for meat) | 5.5 |
| 34 | Black pepper | 7.1 |
| 35 | Green pepper | 5.9 |
| 36 | Dill | 11.4 |
| 37 | Caraway | 6.7 |
| 38 | Oak wood, cognac | 32.3 |
| 39 | Woody, resinous | 31.7 |
| 40 | Cedarwood | 16.8 |
| 41 | Mothballs | 28.9 |
| 42 | Minty, peppermint | 30.9 |
| 43 | Camphor | 31.8 |
| 44 | *Eucalyptus* | 39.7 |
| 45 | Chocolate | 7.4 |
| 46 | Vanilla | 30.4 |
| 47 | Sweet | 56.8 |
| 48 | Maple syrup | 22.2 |
| 49 | Caramel | 20.0 |
| 50 | Malty | 16.1 |
| 51 | Raisins | 20.2 |
| 52 | Molasses | 25.6 |
| 53 | Coconut | 19.3 |
| 54 | Anise (licorice) | 27.1 |
| 55 | Alcoholic | 43.5 |
| 56 | Etherish, anesthetic | 40.1 |
| 57 | Cleaning fluid | 49.8 |
| 58 | Gasoline, solvent | 12.5 |
| 59 | Turpentine (pine oil) | 21.7 |
| 60 | *Geranium* leaves | 33.4 |
| 61 | Celery | 8.5 |
| 62 | Fresh green vegetables | 9.0 |
| 63 | Crushed weeds | 15.2 |
| 64 | Crushed grass | 14.9 |
| 65 | Herbal, green, cut grass | 18.1 |
| 66 | Raw cucumber | 10.8 |
| 67 | Hay | 13.0 |
| 68 | Grainy (as grain) | 9.6 |
| 69 | Yeasty | 11.8 |
| 70 | Bakery (fresh bread) | 5.3 |
| 71 | Sour milk | 15.5 |
| 72 | Fermented (rotten) fruit | 23.3 |
| 73 | Beery | 13.0 |
| 74 | Soapy | 60.7 |
| 75 | Leather | 13.3 |
| 76 | Cardboard | 10.4 |
| 77 | Rope | 6.7 |
| 78 | Wet paper | 10.0 |
| 79 | Wet wool, wet dog | 8.9 |
| 80 | Dirty linen | 9.2 |
| 81 | Stale | 24.2 |
| 82 | Musty, earthy, moldy | 8.0 |
| 83 | Raw potato | 7.3 |
| 84 | Mouse-like | 6.0 |
| 85 | Mushroom | 10.1 |
| 86 | Peanut butter | 7.0 |
| 87 | Beany | 3.8 |
| 88 | Eggy (fresh eggs) | 7.2 |
| 89 | Bark, birch bark | 25.3 |
| 90 | Cork | 16.2 |
| 91 | Burnt, smoky | 6.4 |
| 92 | Fresh tobacco smoke | 15.2 |
| 93 | Incense | 44.2 |
| 94 | Coffee | 4.8 |
| 95 | Stale tobacco smoke | 17.4 |
| 96 | Burnt paper | 2.9 |
| 97 | Burnt milk | 5.4 |
| 98 | Burnt rubber | 12.3 |
| 99 | Tar | 5.1 |
| 100 | Creosote | 8.2 |
| 101 | Disinfectant, carbolic | 51.3 |
| 102 | Medicinal | 56.1 |
| 103 | Chemical | 66.1 |
| 104 | Bitter | 29.3 |
| 105 | Sharp, pungent, acid | 40.2 |
| 106 | Sour, vinegar | 35.1 |
| 107 | Sauerkraut | 14.9 |
| 108 | Ammonia | 20.0 |
| 109 | Urine | 10.6 |
| 110 | Cat urine | 6.7 |
| 111 | Fishy | 2.9 |
| 112 | Kippery (smoked fish) | 2.5 |
| 113 | Seminal, sperm-like | 7.7 |
| 114 | New rubber | 28.1 |
| 115 | Sooty | 4.3 |
| 116 | Burnt candle | 8.5 |
| 117 | Kerosene | 9.4 |
| 118 | Oily, fatty | 15.9 |
| 119 | Buttery, fresh butter | 10.5 |
| 120 | Paint | 32.2 |
| 121 | Varnish | 41.6 |
| 122 | Popcorn | 2.8 |
| 123 | Fried chicken | 2.0 |
| 124 | Meaty (cooked, good) | 1.9 |
| 125 | Soupy | 7.7 |
| 126 | Cooked vegetables | 7.4 |
| 127 | Rancid | 20.6 |
| 128 | Sweaty | 11.3 |
| 129 | Cheesy | 9.3 |
| 130 | Household gas | 12.3 |
| 131 | Sulfidic | 10.2 |
| 132 | Garlic, onion | 6.0 |
| 133 | Metallic | 19.5 |
| 134 | Blood, raw meat | 7.3 |
| 135 | Animal | 4.7 |
| 136 | Sewer odor | 4.8 |
| 137 | Putrid, foul, decayed | 17.8 |
| 138 | Fecal (like manure) | 6.2 |
| 139 | Cadaverous (dead animal) | 9.8 |
| 140 | Sickening | 22.1 |
| 141 | Dry, powdery | 22.3 |
| 142 | Chalky | 15.9 |
| 143 | Light | 48.4 |
| 144 | Heavy | 38.6 |
| 145 | Cool, cooling | 48.9 |
| 146 | Warm | 30.6 |

The 146 descriptors were provided by the 85 subjects who smelled white in all of the identification and delayed match-to-sample experiments. P.A. is the percentage of applicability (geometric mean of the percent usage and percentage of the maximum possible score).

Moreover, 20 subjects were asked to rate 20 different odorants along VAS scales representing the two principal axes of human olfactory perception: One axis ranging from very pleasant to very unpleasant, and the other axis ranging from highly edible to highly poisonous (1, 13, 18). Of the 20 odorants they rated, 12 were previously well-characterized monomolecular odorants that span the first principal component of perception, four were previously used versions of 40-component olfactory white, and four were 10-component mixtures which provided maximal span of olfactory space. Whereas the pleasantness and edibility/poisonousness of the 20 odorants ranged from 0.10 to 0.86 and 0.11 to 0.70 respectively (after parsing the VAS to the range 0-1), the average pleasantness and edibility/poisonousness of olfactory white was 0.46±0.08 and 0.37±0.05 respectively (FIGS. 5A,B). In other words, olfactory white was largely intermediate along the key axes of human olfactory perception.

Example 3

Olfactory White is a Gestalt that Persists Over Time

To ask whether the percept of White is maintained over time, 20 participants from the above studies were re-invited to participate in an additional study conducted about six months after their initial and only acquaintance with Laurax.

Moreover, in this experiment the present inventors also asked whether Laurax can mask other odors. Subjects were presented with 12 odorants, each delivered twice. Four of the odorants were the monomolecules most prominent in rose (10), a fifth odorant was a rose mixture made of these four monomolecules combined (Table 5, hereinbelow), five odorants were 30-component mixtures (white) which each contained these four monomolecules mixed with 26 additional molecules selected to span physicochemical space (Table 6, hereinbelow), and the remaining two odorants were the monomolecules isoamyl acetate and S-(methylthio) butyrate. Subjects were asked to identify the odorants in a 7-alternative (10 subjects) or 4-alternative (10 subjects) forced-choice identification task, where the alternatives always included: Rose, Laurax, Other, and either one (4AFC) or four (7AFC) additional odor names, selected to best fit the monomolecules used.

TABLE 5

The four main components of a rose which yield the rose odor

| Molecule name | CID Number | Cas Number | % of the rose mixture |
|---|---|---|---|
| β-phenylethyl alcohol | 60-12-8 | 6054 | 98% |
| Geraniol | 106-24-1 | 637566 | 1.4% |
| Citronellol | 106-22-9 | 8842 | 0.3% |
| Nerol | 106-25-2 | 643820 | 0.3% |

The most prominent labels which were given by independent group of ten people were: rose, *narcissus, geranium*, lemon and citrus blossoms.

TABLE 6

Five versions of 30-components mixture

| Version I | Version II | Version III | Version IV | Version V |
|---|---|---|---|---|
| 177 | 179 | 179 | 176 | 179 |
| 264 | 261 | 261 | 180 | 1060 |
| 307 | 307 | 307 | 454 | 1127 |
| 460 | 460 | 612 | 6054 | 2879 |
| 1031 | 2969 | 3314 | 6544 | 6054 |
| 6054 | 6054 | 4133 | 6654 | 6561 |
| 4133 | 6569 | 6054 | 7059 | 6736 |
| 5634 | 6584 | 6584 | 7344 | 7059 |
| 6184 | 6989 | 7685 | 7460 | 7460 |
| 6501 | 7654 | 7793 | 7654 | 7583 |
| 7165 | 7685 | 7799 | 7685 | 7685 |
| 7654 | 7793 | 7921 | 7731 | 7714 |
| 7731 | 8048 | 8048 | 7799 | 8048 |
| 8091 | 8130 | 8103 | 7966 | 8118 |
| 8118 | 8148 | 8842 | 7991 | 8139 |
| 8842 | 8842 | 10882 | 8048 | 8186 |
| 8858 | 8892 | 11002 | 8139 | 8842 |
| 12180 | 12348 | 12180 | 8186 | 8858 |
| 17100 | 16666 | 12232 | 8842 | 10882 |
| 22873 | 24915 | 12741 | 16666 | 10890 |
| 24915 | 31249 | 16666 | 20859 | 12180 |
| 31272 | 31272 | 17100 | 24915 | 16666 |
| 62444 | 31276 | 20859 | 26331 | 24915 |
| 62465 | 62433 | 24915 | 31265 | 31244 |
| 93009 | 91497 | 91497 | 31272 | 31276 |
| 440917 | 93009 | 93009 | 31276 | 62444 |
| 443158 | 440917 | 440967 | 62465 | 93009 |
| 637566 | 637566 | 637566 | 637566 | 443158 |
| 643820 | 643820 | 643820 | 643820 | 637566 |
| 5281515 | 5281515 | 5283349 | 5281168 | 643820 |

The four CID numbers of the rose in bold and the complementary 26 molecules CID numbers for ideal spanning of the physicochemical space.

Despite the brief and limited past exposure to Laurax, subjects largely maintained the percept in mind. Whereas chance selection of Laurax was 14.3% in the first experiment, and 25% in the second, it was correctly selected 54% of the time in the first experiment ($t(9)=7.96$, $p<0.001$), and 65% of the time in the second experiment ($t(9)=5.05$, $p<0.001$). Moreover, the percept of Laurax largely overshadowed the percept of rose. Specifically, across both experiments the mixture of rose was correctly identified 70% of the time, yet only twice out of 40 trials (5%) was it labeled Laurax ($t(19)=7.25$, $p<0.001$). In contrast, Laurax (which contained the four molecules of rose) was correctly identified 59.5% percent of the time, yet only 14 times out of 200 trials (7%) was it labeled rose ($t(19)=9.52$, $p<0.001$) (full results of this experiment are in FIG. 8). In other words, subjects remembered the percept of white, and it served to effectively obscure the percept of rose.

Discussion

As illustrated in FIG. 2A: the more components two mixtures have, the more similar they smell, despite sharing no individual components in common. Moreover, odorant-mixtures with ~30 components or more begin to smell alike, having a quality referred to herein as olfactory white. Large mixtures in the real world, such as wine, coffee, and rose, do not all smell similar and 'white' for two reasons: The first is that unlike the olfactory whites generated herein, the components of wine, coffee and rose were not designed to span stimulus space. As seen in FIG. 4B, if mixture components are less spanned, the ensuing odorant is different from white. The second consideration is that unlike the olfactory whites generated herein, wine, coffee and rose do not contain equal intensity components. As seen in FIG. 4B, if mixture components are not equated for intensity, the ensuing odorant also smells less white. Such imbalance is typical in natural mixtures. For example, computing the spread of the 63 key components of rose (10) in physicochemical space reveals that they reflect an extreme cluster, whereas the 60-component whites generated herein (Laurax) reflected an average span (see FIG. 9 for this and additional examples). Moreover, one of the components of rose alone, phenylethyl alcohol, contributes ~70% of rose headspace (19), and indeed this component alone generates a poor-quality but unmistakable smell of rose. In other words, a natural olfactory object such as rose contains components that are clustered in olfactory space, and of unequal intensity, and therefore doesn't smell white.

Olfaction is considered a synthetic rather than analytical sensory system (20-24). For example, humans are very poor at identifying components in a mixture, even when they are familiar with the components alone (5-7). Similarly, cortical patterns of neural activity induced by a mixture are unique, and not a combination of neural activity induced by the mixtures' components (25-29). Moreover, the pattern of neural activity in the olfactory bulb following a natural object typically reflects the pattern associated with the dominant monomolecular odorant (alone) associated with that object (30). In other words, the olfactory system treats odorant-mixtures as unitary synthetic objects, and not as an analytical combination of components (20-24, 28, 29, 31). The current results are consistent with this notion, and the ~30 component phenomenon therefore implies computational boundaries for olfactory receptors, bulb, cortex, and perception.

Example 4

Exemplary Mixtures

Exemplary mixtures according to some embodiments of the present invention are provided in Tables 7A-C below.

Each of Tables 7A and 7B lists preferred odorant components for two odorant mixtures with 60 components, and Table 6C lists preferred odorant components for an odorant mixture with 30 components. The tables include lists of odorant components identified by their CID numbers.

TABLE 7A

| |
|---|
| 177 |
| 179 |
| 180 |
| 261 |
| 326 |
| 460 |
| 612 |
| 999 |
| 1060 |
| 1068 |
| 1127 |
| 1140 |
| 1146 |
| 2879 |
| 3314 |
| 3776 |
| 5634 |
| 6544 |
| 6561 |
| 6654 |
| 6982 |
| 7344 |
| 7463 |
| 7519 |
| 7583 |
| 7632 |
| 7654 |
| 7710 |
| 7714 |
| 7799 |
| 7921 |
| 8030 |
| 8103 |
| 8148 |
| 8186 |
| 8635 |
| 8858 |
| 10560 |
| 10821 |
| 10890 |
| 10976 |
| 12020 |
| 12178 |
| 12180 |
| 12348 |
| 12367 |
| 17100 |
| 18827 |
| 22873 |
| 24915 |
| 26331 |
| 31249 |
| 31265 |
| 61016 |
| 62444 |
| 62465 |
| 93009 |
| 637566 |
| 5281168 |
| 5283349 |

TABLE 7B

| |
|---|
| 176 |
| 240 |
| 264 |
| 307 |
| 798 |
| 1031 |
| 2758 |

TABLE 7B-continued

| |
|---|
| 2969 |
| 4133 |
| 6054 |
| 6184 |
| 6501 |
| 6590 |
| 6736 |
| 6989 |
| 7059 |
| 7150 |
| 7165 |
| 7363 |
| 7410 |
| 7600 |
| 7685 |
| 7731 |
| 7749 |
| 7762 |
| 7793 |
| 7848 |
| 7888 |
| 7966 |
| 7991 |
| 8048 |
| 8051 |
| 8118 |
| 8130 |
| 8892 |
| 10430 |
| 10722 |
| 10882 |
| 11002 |
| 11124 |
| 11509 |
| 11552 |
| 12232 |
| 12741 |
| 14286 |
| 15380 |
| 16666 |
| 19310 |
| 22201 |
| 22386 |
| 31244 |
| 31276 |
| 62336 |
| 62433 |
| 91497 |
| 440917 |
| 440967 |
| 443158 |
| 5281515 |
| 6259976 |

TABLE 7C

| |
|---|
| 264 |
| 307 |
| 454 |
| 1031 |
| 6054 |
| 6736 |
| 7165 |
| 7460 |
| 7600 |
| 7685 |
| 7793 |
| 7848 |
| 7888 |
| 7966 |
| 8025 |
| 8048 |
| 8091 |
| 8118 |
| 8797 |
| 8918 |
| 10722 |

TABLE 7C-continued 12232
16666
22201
31272
31276
61138
91497
440967
6259976

ANNEX 1

TABLE A.1

Database of 1554 odorant components with CAS Numbers

| | |
|---|---|
| Acetal | 105-57-7 |
| Acetaldehdye phenethyl propyl acetal | 7493-57-4 |
| Acetaldehyde | 75-07-0 |
| Acetaldehyde ethyl cis-3-hexenyl acetal | 28069-74-1 |
| Acetaldehyde ethyl hexyl acetal | 54484-73-0 |
| Acetaldehyde ethyl isoeugenyl acetal | 84029-92-5 |
| Acetaldehyde ethyl linalyl acetal | 40910-49-4 |
| Acetaldehyde ethyl phenethyl acetal | 2556-10-7 |
| Acetaldehyde trans-3-hexenyl acetal | 60763-40-8 |
| Acetalpyrazine, 2- | 22047-25-2 |
| Acetanisole | 100-06-1 |
| Acetate C-11 | 112-19-6 |
| Acetate C-12 | 112-66-3 |
| Acetate C-7 | 112-06-1 |
| Acetate C-8 | 112-14-1 |
| Acetate C-9 | 143-13-5 |
| Acethoxy-3-ethoxybenzaldehyde, 4- | 72207-94-4 |
| Acetic Acid | 64-19-7 |
| Acetoin | 513-86-0 |
| Acetone | 67-64-1 |
| Acetophenone | 98-86-2 |
| Acetovanillone | 498-02-2 |
| Acetoxy-1-ethynyl-2-sec-butylcyclohexane, 1- | 37172-05 |
| Acetoxy-3-butanone, 2- | 4906-24-5 |
| Acetoxy-3-ethoxybenzaldehyde, 4- | 72207-94-4 |
| Acetoxy-3-pentyltrahydropyran, 4- | 18871-14-2 |
| Acetoxydihydrotheaspirane, 6- | 57893-27-3 |
| Acetoxyphenyl)-2-butanone, 4-(p- | 3572-06-3 |
| Acetyl carene | 3608-11-5 |
| Acetyl cedrene | 32388-55-9 |
| Acetyl isovaleryl | 13706-86-0 |
| Acetyl propionyl | 600-14-6 |
| ACETYL VALERYL | 96-04-8 |
| Acetyl-1,1,2,3,3,6-hexamethylindan, 5- | 15323-35-0 |
| Acetyl-1-methylpyrrole, 2- | 932-16-1 |
| Acetyl-2,5-dimethylthiophene, 3- | 2530-10-1 |
| Acetyl-2-5dimethylfuran, 3- | 10599-70-9 |
| Acetyl-2-thiazoline, 2- | 29926-41-8 |
| Acetyl-3,5(or 6)-dimethylpyrazine, 2- | 54300-08-2 |
| Acetyl-3-ethylprazine, 2- | 32974-92-8 |
| Acetyl-3-isopropyl-1,1,2,6-tetramethylindane | 68140-48-7 |
| Acetyl-3-methylpyrazine, 2- | 23787-80-6 |
| Acetyl-5-methylfuran, 2- | 1193-79-9 |
| Acetyl-6-t-butyl-1,1-dimethylindan, 4- | 13171-00-1 |
| Acetylbutyryl | 3848-24-6 |
| Acetylpyridine, 2- | 1122-62-9 |
| Acetylpyridine, 3- | 350-03-8 |
| Acetylthiazole, 2- | 24295-03-2 |
| Acetylthiophene | 88-15-3 |
| Adipic acid | 124-04-9 |
| AAET | 88-29-9 |
| Alanine, B- | 107-95-9 |
| Alanine, dl- | 302-72-7 |
| Alanroot oil | 97676-35-2 |
| Alcohol C-6 | 111-27-3 |
| Alcohol C-7 | 111-70-6 |
| Alcohol C-9 | 143-08-8 |
| Alcohol C-11 Undeyclenic | 112-43-6 |
| Alcohol C-11 Undeyclic | 112-42-5 |
| Alcohol C-14 MYRISTIC | 112-72-1 |

TABLE A.1-continued

Database of 1554 odorant components with CAS Numbers

| | |
|---|---|
| Aldehyde C-11, undecylenic | 112-45-8 |
| Aldehyde C-12 MNA | 110-41-8 |
| Aldehyde C-14, myristic | 124-25-4 |
| Aldehyde C-6 | 66-25-1 |
| Aldehyde C-7 dimethyl acetal | 10032-05-0 |
| Allo-ocimenol | 22450-63-4 |
| Ally 2-ethylbutyrate | 7493-69-8 |
| Ally 2-furoate | 4208-49-5 |
| Allyl alpha- ionone | 79-78-7 |
| Allyl butyrate | 2051-78-7 |
| Allyl cinnamate | 1866-31-5 |
| Allyl cyclhexylacetate | 4728-82-9 |
| Allyl cyclohexanepropionate | 2705-87-5 |
| Allyl disulfide | 2179-57-9 |
| Allyl heptylate | 142-19-8 |
| Allyl hexanoate | 123-68-2 |
| Allyl isothiocyanate | 57-06-7 |
| Allyl isovalerate | 2835-39-4 |
| allyl mercaptan | 870-23-5 |
| Allyl nonanoate | 7493-72-3 |
| Allyl octanoate | 4230-97-1 |
| Allyl phenoxyacetate | 7493-74-5 |
| Allyl phenylacetate | 1797-74-6 |
| Allyl propionate | 2408-20-0 |
| Allyl sulfide | 592-88-1 |
| Allyl thiopropionate | 41820-22-8 |
| Allyl tiglate | 7493-71-2 |
| Allyl trimethyl hexanoate | 71500-37-3 |
| Allyl-2,6-diemthoxyphenol, 4- | 6627-88-9 |
| Allylanisole, 4- | 140-67-0 |
| Almond oil, bitter | 8013-76-1 |
| Almond oil, sweet | 8007-69-0 |
| Amberette seed (n) | 8015-62-1 |
| Ambergris tincture | 8038-65-1 |
| Ambrettolide | 7779-50-2 |
| Ambroxide, (−)- | 6790-58-5 |
| Aminoacetophenone, 2- | 551-93-9 |
| Ammonium sulfide | 12135-76-1 |
| Amyl (iso) benzoate | 94-46-2 |
| Amyl (iso) cinnamate | 7779-65-9 |
| Amyl 2-furoate | 1334-82-3 |
| Amyl acetate | 628-63-7 |
| Amyl alcohol | 71-41-0 |
| Amyl cinnamic aldehyde diethyl acetal, "alpha- | 60763-41-9 |
| Amyl cinnamic aldehyde, alpha- | 122-40-7 |
| Amyl cinnamylidene/methyl anthranilate Schiff base, alpha- | 68527-78-6 |
| Amyl formate | 638-49-3 |
| Amyl hexanoate | 540-07-6 |
| Amyl isoeugenol | 10484-36-3 |
| AMYL ISOVALERATE | 25415-62-7 |
| Amyl octanoate | 638-25-5 |
| Amyl vinyl carbinyl acetate | 2442-10-6 |
| Amyl(iso) salicylate | 87-20-7 |
| Amyl-alpha-pyrone, 6- | 27593-23-3 |
| Amylcinnamaldehyde dimethyl acetal, alpha- | 91-87-2 |
| Amylcinnamic aldehyde dimethyl acetal, alpha- | 91-87-2 |
| Amylcinnamyl acetate, alpha | 7493-78-9 |
| Amylcinnamyl alcohol, alpha | 101-85-9 |
| Amylcyclohexanone, 4-t- | 16587-71-6 |
| Amylcyclohexyl acetate (mixed isomers) | 67874-72-0 |
| Amylcyclopentenone | 25564-22-1 |
| Amylvinylcarbinol | 3391-86-4 |
| Anethole | 4180-23-8 |
| *Angelica* oil (root or seed) | 8015-64-3 |
| Angelicalactone, alpha | 591-12-8 |
| Anisaldehyde, o- | 135-02-4 |
| Anisaldehyde, p- | 123-11-5 |
| Anise oil | 84775-42-8 |
| Anisic acid, p- | 100-09-4 |
| Anisole | 100-66-3 |
| Anisyl acetate | 104-21-2 |
| Anisyl alcohol | 105-13-5 |
| Anisyl formate | 122-90-8 |
| Anisyl n-butyrate | 6963-56-0 |
| Anisyl phenylacetate | 102-17-0 |
| Anisyl propionate | 7549-33-9 |

TABLE A.1-continued

Database of 1554 odorant components with CAS Numbers

| Name | CAS |
|---|---|
| Anisylidene acetone | 943-88-4 |
| Arabinogalactan | 9036-66-2 |
| Armoise oil | 8008-93-3 |
| *Artemisia* oil | 8008-93-3 |
| Azodicarbonamide | 123-77-3 |
| Baccartol | 68916-62-1 |
| Balsam, Canadian | 8021-28-1 |
| Balsam, Peru | 8007-00-9 |
| Basil oil, sweet | 8015-73-4 |
| Bay oil | 8006-78-8 |
| Bay oil, sweet | 8007-48-5 |
| Beeswax absolute | 8012-89-3 |
| Benezethiol | 108-98-5 |
| Benzaldehyde | 100-52-7 |
| Benzaldehyde dimethyl acetal | 1125-88-8 |
| Benzaldehyde glyceryl acetal | 1313-88-6 |
| Benzaldehyde propylene glycol acetal | 2568-25-4 |
| Benzenethiol | 108-98-5 |
| Benzhydrol | 91-01-0 |
| Benzoic acid | 65-85-0 |
| Benzoin | 579-44-2 |
| Benzoin (resinoid) | 9000-05-9 |
| Benzonitrile | 100-47-0 |
| Benzophenone | 119-61-9 |
| Benzothiazole | 95-16-9 |
| Benzyl acetate | 140-11-4 |
| Benzyl acetoacetate | 5396-89-4 |
| Benzyl acetone | 2550-26-7 |
| Benzyl alcohol | 100-51-6 |
| Benzyl benzoate | 120-51-4 |
| Benzyl butyrate | 103-37-7 |
| Benzyl cinnamate | 103-41-3 |
| Benzyl disulfide | 105-60-7 |
| Benzyl formate | 104-57-4 |
| Benzyl isoamyl ether | 122-73-6 |
| Benzyl isobutyrate | 103-28-6 |
| Benzyl isoeugenol | 120-11-6 |
| Benzyl isovalerate | 103-38-8 |
| Benzyl laurate | 140-25-0 |
| Benzyl mercaptan | 100-53-8 |
| Benzyl phenylacetate | 102-16-9 |
| Benzyl propionate | 122-63-4 |
| Benzyl salicylate | 118-58-1 |
| Benzyl trans-2-methyl-2-butenoate | 37526-88-8 |
| BENZYL TRANS-2-METHYL-2-BUTENOATE | 37526-88-8 |
| Benzylidene acetone | 122-57-6 |
| Bergamot oil | 8007-75-8 |
| Beta ionone | 14901-07-6 |
| BETA-IONONE | 1490-07-6 |
| BETA-PINENE | 18172-67-3 |
| Biphenyl | 92-52-4 |
| Birch tar oil | 8001-88-5 |
| Bis(methylthio)methane | 1618-26-4 |
| Bisabolene | 495-62-5 |
| Bitter orange oil | 68916-04-1 |
| Bois de rose oil, acetylated | 68952-69-2 |
| Bois de rose oil, Brazilian | 8015-77-8 |
| Boldo leaf oil | 8022-81-9 |
| Borneol acetate, laevo- | 5655-61-8 |
| Borneol, 1- | 464-45-9 |
| Bornyl isovalerate | 76-50-6 |
| Bromstyrol | 103-64-0 |
| Butanedithiol, 1,3- | 24330-52-7 |
| Butanedithiol, 2,3- | 4532-64-3 |
| Butanethiol, 1- | 109-79-5 |
| Butanethiol, 2- | 513-53-1 |
| BUTYL 2-METHYLBUTYRATE | 15706-73-7 |
| Butyl acetate | 123-86-4 |
| Butyl alcohol | 71-36-3 |
| Butyl anthranilate, n- | 7756-96-9 |
| Butyl benzoate | 136-60-7 |
| Butyl butyrolactate | 7492-70-8 |
| Butyl caproate | 626-82-7 |
| Butyl cinnamate aldehyde | 1492-44-6 |
| Butyl cinnamate, n- | 538-65-8 |
| Butyl formate | 596-84-7 |
| BUTYL HEPTANOATE | 5454-28-4 |
| Butyl isobutyrate | 97-87-0 |
| Butyl isovalerate, n- | 109-19-3 |
| Butyl lactate | 138-22-7 |
| Butyl laevulinate | 2052-15-5 |
| Butyl laurate | 106-18-3 |
| Butyl n-butyrate | 109-21-7 |
| Butyl oleate | 142-77-8 |
| Butyl phenylacetate | 122-43-0 |
| Butyl phthalide, 3- | 6066-49-5 |
| Butyl p-hydroxybenzoate | 94-26-8 |
| Butyl propionate, n- | 590-01-2 |
| Butyl salicylate, n- | 2052-14-4 |
| Butyl stearate | 123-95-5 |
| Butyl sulfide | 554-40-1 |
| Butyl undecylenate | 109-42-2 |
| BUTYL VALERATE | 591-68-4 |
| Butyl-2,4-dimethyldihydropyrane, 6- | 24237-00-1 |
| Butyl-4,4,6-trimethyl-1,3-dioxane, 2- | 54546-26-8 |
| Butyl-alpha-methylhydrocinnamic aldehyde | 80-54-6 |
| Butyl-alpha-methylhydrocinnamic aldehyde | 80-54-6 |
| Butylamine | 109-73-9 |
| Butylated hydroxytoluene | 128-37-0 |
| Butylcyclohexanol, 4-tert- | 98-52-2 |
| Butylcyclohexanone, 2-sec- | 14765-30-1 |
| Butylcyclohexanone, p-tert- | 98-53-3 |
| Butylcyclohexyl acetate, 2-t- | 88-41-5 |
| Butylcyclohexyl acetate, 4-tert- | 32210-23-4 |
| Butyldihydrocinnamaldehyde, p-tert- | 18127-01-0 |
| Butylidene phthalide, 3- | 551-08-6 |
| Butyl-l-lactate | 34451-19-9 |
| Butylphenol, p-tert- | 98-54-4 |
| Butylquinoline, sec- | 133-58-0 |
| Butyraldehyde, n- | 123-72-8 |
| Butyric acid, n- | 107-92-6 |
| Butyrophenone | 495-40-9 |
| *Cabreuva* oil | 68188-03-4 |
| Cade oil rectified | 8013-10-3 |
| Cadinene | 29350-73-0 |
| Caffeine | 58-08-2 |
| Cajeput oil | 8008-98-8 |
| *Calamus* oil | 8015-79-0 |
| Camphene | 5794-03-6 |
| Camphor oil | 8008-51-3 |
| Camphor, USP | 464-49-3 |
| *Cananga* oil | 68606-83-7 |
| Caprylic acid | 124-07-2 |
| Caraway oil | 8000-42-8 |
| Cardamom seed oil | 8000-66-6 |
| Carene, delta-3- | 13466-78-9 |
| Carrot oil | 8015-88-1 |
| Carvacrol | 499-75-2 |
| CARVACRYL ETHYL ETHER | 4732-13-2 |
| CARVACRYL METHYL ETHER | 6379-73-3 |
| CARVEOL | 99-48-9 |
| Carveol, laevo- | 2102-59-2 |
| Carvomenthenol. 4- | 562-74-3 |
| Carvone, -l | 99-48-9 |
| Carvone, delta | 2244-16-8 |
| Carvone, laevo | 6485-40-1 |
| CARVYL ACETATE | 97-42-7 |
| Carvyl propionate | 97-45-0 |
| Carvylacetate, laevo- | 1205-42-1 |
| Caryophyllene acetate | 32214-91-8 |
| Caryophyllene alcohol | 4586-22-5 |
| Caryophyllene oxide | 1139-30-6 |
| CARYOPHYLLENE, BETA- | 87-44-5 |
| *Cascarilla* oil | 8007-06-5 |
| *Cassia* bark oil | 8007-80-5 |
| Castor oil | 8001-79-4 |
| Castoreum | 8023-83-4 |
| Cedar leaf oil | 8007-20-3 |
| Cedarwood oil atlas | 8023-85-6 |
| Cedarwood oil, Texas | 68990-83-0 |
| Cedarwood oil, Virginia | 8000-27-9 |
| Cedr-8-ene epoxide | 13567-39-0 |
| Cedrane, alpha | 469-61-4 |
| CEDRENOL | 28231-03-0 |
| Cedrenyl acetate | 1405-92-1 |
| CEDROL | 77-53-2 |

TABLE A.1-continued

Database of 1554 odorant components with CAS Numbers

| Name | CAS |
|---|---|
| CEDROL METHYL ETHER | 19870-74-7 |
| Cedryl acetate | 77-54-3 |
| Cedryl formate | 39900-38-4 |
| Celery seed oil | 8015-90-5 |
| Cetyl acetate | 629-70-9 |
| Cetyl alcohol | 36653-82-4 |
| Chamomile flower, Hugarian, oil | 8002-66-2 |
| Chamomile oil, Roman | 8015-92-7 |
| *Chenopodium* oil | 8006-99-3 |
| CINEOLE, 1,4- | 470-67-7 |
| CINEOLE, 1,8- | 470-82-6 |
| CINNAMALDEHYDE | 104-55-2 |
| CINNAMIC ACID | 621-82-9 |
| Cinnamic alcohol | 104-54-1 |
| Cinnamic aldehyde dimethyl acetal | 4364-06-1 |
| Cinnamon bark oil. "Caylon" | 8007-80-5 |
| CINNAMYL ACETATE | 103-54-8 |
| Cinnamyl anthranilate | 87-29-6 |
| Cinnamyl benzoate | 5320-75-2 |
| CINNAMYL BUTYRATE | 103-61-7 |
| CINNAMYL BUTYRATE, trans | 78761-39-4 |
| CINNAMYL CINNAMATE | 122-69-0 |
| CINNAMYL FORMATE | 104-65-4 |
| CINNAMYL ISOBUTYRATE | 103-59-3 |
| CINNAMYL ISOVALERATE | 104-27-2 |
| CINNAMYL ISOVALERATE, trans | 69121-78-4 |
| CINNAMYL NITRILE | 1885-38-7 |
| CINNAMYL PROPIONATE | 103-56-0 |
| CINNAMYL PROPIONATE, trans | 78761-38-3 |
| Cinnamyl tiglate | 61792-12-9 |
| Cinnimic aldehyde methyl anthranilate | 94386-48-8 |
| Citral | 5392-66-2 |
| CITRAL DIETHYL ACETAL | 7549-66-2 |
| Citral dimethyl acetal | 7549-37-3 |
| Citral ethylene glycol acetal | 66408-78-4 |
| Citral-methlanthranilate (Schiff base) | 67801-47-2 |
| CITRIC ACID | 77-29-9 |
| *Citronella* oil | 8000-29-1 |
| Citronellal | 106-23-0 |
| Citronellic acid | 502-47-6 |
| Citronellol | 106-22-9 |
| Citronellol, (S)-(−)-B- | 7540-51-4 |
| Citronellyl acetate | 150-84-5 |
| CITRONELLYL BUTYRATE | 141-16-2 |
| Citronellyl crotonate | 68039-38-3 |
| CITRONELLYL ETHYL OXALATE SUPRA | 60788-25-2 |
| Citronellyl ethyl ether | 69929-16-4 |
| CITRONELLYL FORMATE | 105-85-1 |
| CITRONELLYL ISOBUTYRATE | 97-89-2 |
| CITRONELLYL NITRILE | 51566-62-2 |
| Citronellyl oxyacetaldehyde | 7492-67-3 |
| Citronellyl phenylacetate | 139-70-8 |
| Citronellyl propanoate | 141-14-0 |
| CITRONELLYL TIGLATE | 24717-85-9 |
| Citronellyl valerate | 7540-53-6 |
| CITRONELLYL VALERATE | 7540-53-6 |
| CITRONELLYLOXY ACETALDEHYDE 50% BA | 7492-67-3 |
| Civet absolute | 68916-26-7 |
| Civetone | 542-46-1 |
| Clary oil | 8016-63-5 |
| Clove bud oil | 8000-34-8 |
| Cognac oil | 8016-21-5 |
| Copaiba oil | 8001-61-4 |
| Coriander oil | 8008-52-4 |
| Cornmint oil | 68917-18-0 |
| *Costus* root oil | 8023-88-9 |
| Coumarin | 91-64-5 |
| Cresol, m- | 108-39-4 |
| Cresol, o- | 95-48-7 |
| CRESOL, p- | 106-44-5 |
| Cresyl benzoate, p- | 614-34-6 |
| CRESYL CAPRYLATE, PARA- | 59558-23-5 |
| Cresyl isobutyrate | 103-93-5 |
| CRESYL METHYL ETHER, P- | 104-93-8 |
| Cresyl salicylate, p- | 607-88-5 |
| Cubeb oil | 8007-87-2 |
| Cumin oil | 8014-13-9 |
| CUMIN ALDEHYDE | 122-03-2 |
| Cuminyl nitrile | 13816-33-6 |
| *Curcuma* oil | 8024-37-1 |
| Cyclamen alcohol | 4759-19-8 |
| Cyclamen aldehyde-methyl anthranilate | 91-50-9 |
| Cyclocitral, beta | 432-25-7 |
| Cyclohexancarboxyclic acid | 98-89-5 |
| Cyclohexaneacetic acid | 5292-21-7 |
| Cyclohexaneethyl acetate | 21722-83-8 |
| Cyclohexanol | 108-93-0 |
| Cyclohexyl acetate | 622-45-7 |
| CYCLOHEXYL BUTYRATE | 1551-44-6 |
| Cyclohexyl cyclohexanone, 2- | 90-42-6 |
| CYCLOHEXYL ISOVALERATE | 7774-44-9 |
| CYCLOHEXYL PROPIONATE | 6222-35-1 |
| Cyclohexylethyl alcohol | 4442-79-9 |
| Cyclopentadecanolide | 106-02-5 |
| Cyclopentadecanone | 502-72-7 |
| Cyclopentanethiol | 1679-07-8 |
| Cyclopentanone | 120-92-3 |
| Cyclopentenyl proionate musk | 84012-64-6 |
| CYMENE, PARA- | 99-87-6 |
| Cypress oil | 8013-26-0 |
| Cyste absolute | 8016-26-0 |
| Cysteine, L- | 52-90-4 |
| *Davana* oil | 8016-03-3 |
| Decadienal, trans, trans-2,4- | 25152-84-5 |
| Decadienal, 2,4- | 2362-88-4 |
| DECADIENAL, trans, trans-2,4- | 25152-84-5 |
| Decahydro-2-naphthol | 825-51-4 |
| Decahydro-beta-naphthyl acetate | 10519-11-6 |
| Decahydro-beta-naphthyl formate | 10519-12-7 |
| Decalactone, | 5579-78-2 |
| DECALACTONE, DELTA- | 705-86-2 |
| DECALACTONE, GAMMA- | 706-14-9 |
| DECANAL | 112-31-2 |
| DECANAL DIMETHYL ACETAL | 7779-41-1 |
| Decanal, trans-2- | 3913-71-1 |
| Decanal, cis-4- | 21662-09-9 |
| DECANOIC ACID | 334-48-5 |
| DECANOL, 1- | 112-30-1 |
| Decanone, 2- | 693-54-9 |
| Decanone, 3- | 928-80-3 |
| DECEN-2-ONE, 3- | 10519-33-2 |
| Decenal, trans-2- | 3913-71-1 |
| Decenoic acid, 9- | 14436-32-9 |
| Decenyl acetate, 9- | 50816-18-7 |
| Decenyl acetate, 9- | 50816-18-7 |
| DECYL ACETATE | 112-17-4 |
| DECYL BUTYRATE | 5454-09-1 |
| Decyl methyl ether | 7289-52-3 |
| DECYL PROPIONATE | 5454-19-3 |
| Decyl vinyl ether | 765-05-9 |
| Decylenic alcohol | 13019-22-2 |
| Dedecenal, 2- | 4826-62-4 |
| Deertongue absolute | 68606-82-6 |
| Deobase | 8020-83-5 |
| DIACETYL | 431-03-8 |
| Dibenzyl | 103-29-7 |
| Dibenzyl ether | 103-50-4 |
| Dibutyl sulfide | 544-40-1 |
| Dicyclohexyl disulfide | 2550-40-5 |
| Diethyl ketone | 96-22-0 |
| Diethyl L-tartrate | 87-91-2 |
| Diethyl malate | 626-11-9 |
| Diethyl malonate | 105-53-3 |
| Diethyl malonate | 141-05-9 |
| Diethyl sebacate | 110-40-7 |
| Diethyl succinate | 123-25-1 |
| Diethyl-5-methylpyrazine | 18138-04-0 |
| Diethylene glycol monoethyl ether | 111-90-0 |
| Diethylene glycol monomethyl ether | 111-77-3 |
| Diethylpyrazine, 2,3 | 15707-24-1 |
| Difuran, 2,2'-(Thiodimethylene) | 1678-67-6 |
| Dihexyl furmarate | 19139-31-2 |
| DIHYDRO CARVYL ACETATE, l- | 20777-49-5 |
| Dihydro-2,4,6-trimethyl-1,3,5(4H)-dithiazine | 94944-51-1 |
| Dihydro-3(2H)thiophenone, 4,5- | 1003-04-9 |
| DIHYDRO-ALPHA-IONON | 31499-72-6 |

TABLE A.1-continued

Database of 1554 odorant components with CAS Numbers

| | |
|---|---|
| Dihydro-alpha-terpineol | 498-81-7 |
| DIHYDROANETHOLE | 140-45-0 |
| Dihydrocarveol | 619-01-2 |
| Dihydrocarveol | 7764-50-3 |
| DIHYDROCARVONE | 5524-05-0 |
| DIHYDROCOUMARIN | 119-84-6 |
| Dihydroeugenol | 2785-87-7 |
| Dihydrogeraniol, 6,7- | 40607-48-5 |
| Dihydroisojasmone | 95-41-0 |
| DIHYDROJASMONE | 1128-08-1 |
| Dihydromethyl-alpha-ionone | 68480-17-1 |
| Dihydromyrcene | 2436-90-0 |
| DIHYDROMYRCENOL | 53219-21-9 |
| DIHYDROMYRCENYL ACETATE | 53767-93-4 |
| DIHYDRONOOTKATONE | 20489-53-6 |
| Dihydrosafrole | 94-58-6 |
| Dihydroterpinyl acetate | 80-25-1 |
| Dihydroxy-3-methylbenzaldehyde | 6248-20-0 |
| Dihydroxybenzaldehyde, 3,4- | 139-85-5 |
| Diisopropropylphenol | 2078-54-8 |
| Dill oil | 8006-75-5 |
| Dill seed oil. Indian | 8016-06-6 |
| Dimethoxyacetophenone, 3,4- | 1131-62-0 |
| Dimethoxybenzene, m- | 151-10-0 |
| Dimethoxyethane 1,1- | 534-15-6 |
| DIMETHOXYPHENOL, 2,6- | 91-10-1 |
| DIMETHYL ANTHRANILATE | 85-91-6 |
| DIMETHYL BENZALDEHYDE, 2,4- | 15764-16-6 |
| DIMETHYL BENZYL CARBINYL BUTYRATE | 10094-34-5 |
| Dimethyl carbonate | 616-38-6 |
| Dimethyl citraconate | 617-54-9 |
| Dimethyl disulfide | 624-92-0 |
| Dimethyl malonate | 108-59-8 |
| DIMETHYL OCTENYL ACETATE | 102-58-9 |
| DIMETHYL PHENYL CARBINOL | 617-94-7 |
| DIMETHYL PHENYL ETHYL CARBINOL | 103-07-1 |
| Dimethyl succinate | 106-65-0 |
| Dimethyl sulfide | 75-18-3 |
| Dimethyl trisulfate | 3658-80-8 |
| DIMETHYL-1,2-CYCLOPENTADIONE, 3,4- | 13494-06-9 |
| DIMETHYL-1-OCTANOL, 3,7- | 106-21-18 |
| Dimethyl-1-octanol, 3,7- | 106-21-8 |
| Dimethyl-1-octanyl butyrate, 3,7- | 67874-80-0 |
| Dimethyl-2,4,6--octatriene, 2,6- | 3016-19-1 |
| Dimethyl-2,6-nonadienenitrile, 3,7- | 61792-11-8 |
| Dimethyl-2-heptanol, 2,6- | 13254-34-7 |
| Dimethyl-3.5.9-undecatrien-2-one, 6,10- | 141-10-6 |
| DIMETHYL-3-HYDROXY-2,5-DIHYDROFURAN-2-ONE, 4,5- | 28664-35-9 |
| Dimethyl-3-octanol, 3,6- | 151-19-9 |
| Dimethyl-3-octanyl acetate | 60763-42-0 |
| Dimethyl-4,6,10-dodecatrien-3-one, 7,11- | 26651-96-7 |
| Dimethyl-4-heptanol, 2,6- | 108-82-7 |
| Dimethyl-4-heptanone, 2,6- | 108-83-7 |
| Dimethyl-4-methoxy-3(2H)-furanone, 2,5- | 4077-47-8 |
| Dimethyl-5-acetylthiazole, 2',4'- | 89-74-7 |
| DIMETHYL-5-HEPTEN-1-AL, 2,6- | 106-72-9 |
| Dimethyl-7-methoxyoctan-2-ol, 3,7- | 41890-92-0 |
| Dimethyl-8-tert-butylcoumarin, 4,6- | 17874-34-9 |
| Dimethyl-9-undecen-2-one, 6,10- | 4433-36-7 |
| Dimethylacetophenone, 2,4 | 89-74-7 |
| Dimethylbenzyl acetate, 2,4- | 632346-96-7 |
| Dimethylbenzylcarbinyl propionate | 67785-77-7 |
| Dimethylfuran, 2,5- | 625-86-5 |
| Dimethylhydroquinone | 150-78-7 |
| Dimethylionone | 68459-99-4 |
| Dimethyloctanyl acetate, 3,7- | 2078-49-8 |
| Dimethyl-p-ethylphenylpropanal, alpha, alpha- | 2661-96-7 |
| Dimethylphenethyl acetate, alpha, alpha- | 151-05-3 |
| Dimethylphenethyl alcohol, alpha, alpha | 100-86-7 |
| Dimethylpyrazine, 2,3- | 5910-89-4 |
| Dimethylpyrazine, 2,6- | 108-50-9 |
| Dimethylpyridine, 2,6- | 108-48-5 |
| Dimethyltetrahydrobenzaldehyde | 68737-61-1 |
| Dimethylthiazole, 4,5- | 3581-91-7 |
| Dimethylthiophenol, 2,6- | 118-72-9 |
| Dimyrcetal | 18479-58-8 |
| Dipentene | 138-86-3 |
| Diphenyl ether | 101-84-8 |
| Diphenyl-2-propanone, 1,3- | 102-04-5 |
| Diphenylamine | 122-39-4 |
| Diphenylmethane | 101-81-5 |
| Dipropylene glycol | 25265-71-8 |
| Disodium succinate | 150-90-3 |
| dl-MENTHYL ACETATE | 16409-45-3 |
| DODECADIENAL, trans,trans-2,4- | 21662-16-8 |
| Dodecalactone, delta- | 713-95-1 |
| Dodecalactone, gamma- | 2305-05-7 |
| DODECENAL, trans-2- | 4826-62-4 |
| Eau de brouts absolute | 8030-28-2 |
| Elemi oil | 8023-89-0 |
| Eposxyguaiene | 68071-23-8 |
| Estragon oil | 8016-88-4 |
| Ethanedithiol, 1,2- | 540-63-6 |
| Ethoxy-3,7-dimethyloctanal, 7- | 3613-33-0 |
| Ethoxybenzaldehyde, p- | 10031-82-0 |
| Ethoxythiazole, 2- | 15679-19-3 |
| ETHYL 10-UNDECENOATE | 692-86-4 |
| Ethyl 2-mercaptopropionate | 19788-49-9 |
| Ethyl 2-methoxybenzyl ether | 64988-06-3 |
| Ethyl 2-methyl-4-pentenoate | 53399-81-8 |
| Ethyl 2-methylbutyrate | 7452-79-1 |
| Ethyl 2-methylpentanoate | 28959-02-6 |
| Ethyl 3-(2-furyl)propanoate | 94278-27-0 |
| Ethyl 3-(methylthio)propionate | 13327-56-5 |
| Ethyl 3-hydrohexanoate | 2305-25-1 |
| ETHYL 3-HYDROXY-BUTYRATE | 5405-41-4 |
| Ethyl 3-hyroxybutyrate | 5405-41-4 |
| ETHYL 3-METHYLTHIO-PROPIONATE | 13327-56-5 |
| Ethyl 3-phenylglycidate | 121-39-1 |
| Ethyl 3-phenylpropionate | 2021-28-5 |
| ETHYL ACETATE | 141-78-6 |
| ETHYL ACETOACETATE | 141-97-9 |
| Ethyl acrylate | 140-88-5 |
| ETHYL AMYL KETONE | 106-68-3 |
| ETHYL ANISATE | 94-30-4 |
| Ethyl anthranilate | 87-25-2 |
| ETHYL BENZOATE | 93-89-0 |
| Ethyl benzoylacetate | 94-02-0 |
| ETHYL BUTYL KETONE | 106-35-4 |
| ETHYL BUTYRATE | 105-54-4 |
| Ethyl caprylate | 106-32-1 |
| ETHYL CINNAMATE | 103-36-6 |
| Ethyl citral | 41448-29-7 |
| ETHYL CROTONATE | 10544-63-5 |
| Ethyl cyclohexanepropionate | 10094-36-7 |
| ETHYL DECANOATE | 110-38-3 |
| ETHYL FORMATE | 109-94-4 |
| ETHYL HEPTOATE | 106-30-9 |
| ETHYL HEXANOATE | 123-66-0 |
| Ethyl hexyl salicylate | 118-60-5 |
| ETHYL ISOBUTYRATE | 97-62-1 |
| ETHYL ISOVALERATE | 108-64-5 |
| ETHYL LACTATE | 97-64-3 |
| ETHYL LAURATE | 106-33-2 |
| ETHYL LEVULINATE | 539-88-8 |
| Ethyl linalool | 10339-55-6 |
| Ethyl linalyl acetate | 61931-80-4 |
| Ethyl maltol | 4940-11-8 |
| Ethyl methylphenylglycidate | 77-83-8 |
| ETHYL MYRISTATE | 124-06-1 |
| Ethyl myristate | 124-06-1 |
| ETHYL OCTANOATE | 106-32-1 |
| Ethyl octine carbonate | 10031-92-2 |
| Ethyl oleate | 111-62-6 |
| ETHYL PALMITATE | 628-97-7 |
| ETHYL PELARGONATE | 123-29-5 |
| Ethyl phenylacetate | 101-97-3 |
| ETHYL PROPIONATE | 105-37-3 |
| Ethyl pyruvate | 617-35-6 |
| ETHYL SALICYLATE | 118-61-6 |
| Ethyl sorbate | 2396-84-1 |
| Ethyl stearate | 111-61-5 |
| Ethyl thioacetate | 625-60-5 |
| ETHYL TIGLATE | 5837-78-5 |
| ETHYL TRANS-2,CIS-4-DECADIENOATE | 3025-30-7 |

TABLE A.1-continued

Database of 1554 odorant components with CAS Numbers

| | |
|---|---|
| Ethyl trans-2-decanoate | 7367-88-6 |
| Ethyl trans-2-octenoate | 2356-90-8 |
| Ethyl trans-3-hexenoate | 2396-83-0 |
| Ethyl undecanoate | 627-90-7 |
| ETHYL UNDECYLENATE | 692-86-4 |
| ETHYL VALERATE | 539-82-2 |
| Ethyl valerate | 539-82-2 |
| ETHYL VANILLIN | 121-32-4 |
| ETHYL VANILLIN PROPYLENE GLYCOL ACETAL | 68527-76-4 |
| Ethyl vinyl ketone | 1629-58-9 |
| Ethyl(p-tolyloxy)acetate | 67028-40-4 |
| Ethyl-2-hydroxy-2-cyclpenten-1-one, 3- | 21835-01-8 |
| ETHYL-2-METHYL-4- PENTENOATE | 53399-81-8 |
| ETHYL-2-METHYLBUTYRATE | 7452-79-1 |
| Ethyl-2-methylpyrazine, 3- | 15707-23-0 |
| Ethyl-2-methylpyridine, 5- | 104-90-5 |
| Ethyl-3,5(or 6)-dimethylpyrazine, 2- | 55031-15-7 |
| Ethyl-3-hydroxy-4-methyl-2(5H)-furanone | 698-10-2 |
| Ethylacetoacetate ethylene glycol ketal | 6413-10-1 |
| Ethylbenzaldehyde, 4- | 4748-78-1 |
| Ethylbenzene | 100-41-4 |
| Ethylbutyl acetate, 2- | 10031-87-5 |
| Ethylbutyraldehyde, 2- | 97-96-1 |
| Ethylbutyric acid, 2- | 88-09-5 |
| Ethylcellulose | 9004-57-3 |
| Ethylene brassylate | 105-95-3 |
| Ethylene dodecanedioate | 54982-83-1 |
| Ethylfenchol, 2- | 18368-91-7 |
| Ethylhexanal | 123-05-7 |
| Ethylhexanol, 2- | 104-76-7 |
| Ethylhexyl acetate | 103-09-3 |
| Ethylphenol, p- | 123-07-9 |
| Ethylpyrazine, 2- | 13925-00-3 |
| Ethylquaiacol, 4- | 2785-89-9 |
| Ethylthiophenol, 2- | 4500-58-7 |
| *Eucalyptus citriodora* oil, acetylated | 68991-29-7 |
| *Eucalyptus citriodora* oil | 8000-48-4 |
| Eugenol | 97-53-0 |
| EUGENYL ACETATE | 93-28-7 |
| Eugenyl formate | 10031-96-6 |
| Eugenyl methyl ether | 93-15-2 |
| Eugenyl phenylacetate | 10402-33-2 |
| Farnesol | 4602-84-0 |
| FENCHYL ACETATE | 13851-11-1 |
| FENCHYL ALCOHOL, ALPHA- | 1632-73-1 |
| Fennel oil | 8006-84-6 |
| Fenugreek absolute | 84625-40-1 |
| Fig leaf absolute | 68916-52-9 |
| Fir Balsam, Oregan | 8021-28-1 |
| Fir needle oil | 8021-28-1 |
| Flouve oil | 68916-09-6 |
| Formaldehyde cyclodecyl ethyl acetal | 58567-11-6 |
| Formaldehyde cyclododecyl methyl acetal | 42604-12-6 |
| Formic acid | 64-18-6 |
| Formyl-1-methyl-4-(4-methyl-pentyl)-3-cyclohexene | 66327-54 |
| Formyl-6,6-dimethylbicyclo(3.1.1)hept-2-ene, 2- | 564-94-3 |
| Formylethyltetramethytetralin | 58243-85-9 |
| Frankincense gum | 8050-07-5 |
| Frenchone | 1195-79-5 |
| Fumaric acid | 110-17-8 |
| Furanmethanethiol formate, 2- | 59020-90-5 |
| FURFURAL | 98-01-1 |
| Furfuryl 3-methylbutanoate | 13678-60-9 |
| Furfuryl acetate | 623-17-6 |
| Furfuryl alcohol | 98-00-0 |
| FURFURYL BUTYRATE | 623-21-2 |
| FURFURYL HEXANOATE | 39252-02-3 |
| Furfuryl isopropyl sulfide | 1883-78-9 |
| Furfuryl mercaptan | 98-02-2 |
| Furfuryl methyl sulfide | 1438-91-1 |
| Furfuryl octanoate | 39252-03-4 |
| Furfuryl pentanoate | 36701-01-6 |
| Furfuryl propionate | 623-19-8 |
| Furfuryl thioacetate | 13678-68-7 |
| Furfuryl thiopropionate | 59020-85-8 |
| Furfurylpyrrole | 1438-94-4 |
| Furyl methyl ketone, 2- | 1192-62-7 |
| Furyl)acrolein, 3-(2- | 623-30-3 |
| *Galbanum* oil | 8023-91-4 |
| *Galbanum* resin | 9000-24-2 |
| Genet absolute | 90131-21-8 |
| Geraniol | 106-24-1 |
| *Geranium* oil | 8000-46-2 |
| GERANYL 2-METHYL BUTANOATE | 68705-63-5 |
| GERANYL ACETATE | 105-87-3 |
| GERANYL ACETOACETATE | 10032-00-5 |
| Geranyl acetone | 3796-70-1 |
| Geranyl benzoate | 94-48-4 |
| GERANYL BUTYRATE | 106-29-5 |
| Geranyl crotonate | 5617-46-4 |
| Geranyl ethyl ether | 40267-72-9 |
| Geranyl formate | 105-86-2 |
| GERANYL ISOBUTYRATE | 2345-26-8 |
| Geranyl isovalerate | 109-20-6 |
| Geranyl linalool | 1113-21-9 |
| Geranyl nitrile | 5146-66-7 |
| Geranyl oxyacetaldehyde | 65405-73-4 |
| Geranyl phenylacetate | 102-22-7 |
| GERANYL PROPIONATE | 105-90-8 |
| Geranyl tiglate | 7785-33-3 |
| Ginger oil | 8007-08-7 |
| Glucose pentaacetate | 604-68-2 |
| Glutamic acid, l- | 56-86-0 |
| Glycerol | 56-81-5 |
| Glycine | 56-40-6 |
| Grapefruit oil | 8016-20-4 |
| Guaiac wood oil | 8016-23-7 |
| GUAIACOL | 90-05-1 |
| Guaicwood acetate | 61789-17-1 |
| Guaiene | 88-84-6 |
| Gurjun oil | 8030-55-5 |
| Hay absolute | 8031-00-3 |
| *Helichrysum* oil | 8023-95-8 |
| Heliotropin | 120-57-0 |
| Heptadienal, 2,4- | 4313-03-5 |
| HEPTADIENAL, trans,trans-2,4- | 4313-03-5 |
| HEPTALACTONE, GAMMA- | 105-21-5 |
| Heptanal | 111-71-7 |
| Heptanoic acid | 111-14-8 |
| Heptanol, 2- | 543-49-7 |
| Heptanol, 3- | 589-82-2 |
| Heptenal, cis-4- | 6728-31-0 |
| Heptenal, trans-2- | 18829-55-5 |
| Heptyl butyrate | 5870-93-9 |
| Heptyl cyclopentanone, 2-n- | 137-03-1 |
| Heptyl formate | 112-23-2 |
| Heptylfuran, 2- | 3777-71-7 |
| Heptyltetrahydrofuran | 2435-16-7 |
| HEXADECANOLIDE | 109-29-5 |
| HEXADIENAL, TRANS,TRANS-2,4- | 142-83-6 |
| HEXADIENAL, trans,trans-2,4- | 142-83-6 |
| Hexadienyl isobutyrate, 2,4- | 16491-24-0 |
| Hexahydro-4,6,6,7,8,8-hexamethylcyclopenta-gamma-2-benzopyran, 1,3,4,6,7,8- | 1222-05-5 |
| Hexalactone, delta- | 823-22-3 |
| HEXALACTONE, GAMMA- | 695-06-7 |
| Hexanedione, 3,4- | 4437-51-8 |
| HEXANEDIONE,3,4- | 4437-51-8 |
| Hexanedithiol, 1,6- | 1191-43-1 |
| HEXANOIC ACID | 142-62-1 |
| Hexanol, 3- | 623-37-0 |
| Hexanone, 3- | 589-38-8 |
| Hexen-1-ol, 4- | 928-92-7 |
| Hexen-1-ol, trans-2- | 928-95-0 |
| Hexen-1-ol, cis- 3- | 928-96-1 |
| Hexen-2-al | 6728-26-3 |
| Hexen-3-one, 4- | 2497-21-4 |
| Hexenal diethyl acetal, trans-2- | 67746-30-9 |
| Hexenal dimethyl acetal, trans-2- | 18318-83-7 |
| HEXENAL, CIS-3- | 6789-806 |
| HEXENAL, trans-3- | 69112-21-6 |
| Hexenoic acid, trans-2- | 13419-69-7 |
| HEXENOL, "TRANS-2- | 928-95-0 |

TABLE A.1-continued

Database of 1554 odorant components with CAS Numbers

| | |
|---|---|
| Hexenyl 2-methylbutanoate, cis-3- | 10094-41-4 |
| Hexenyl 3-methylbutanoate, 3- | 35154-45-1 |
| Hexenyl acetate, 2- | 2497-18-6 |
| Hexenyl acetate, cis-3- | 3681-71-8 |
| Hexenyl anthranilate, cis-3- | 65405-76-7 |
| HEXENYL BENZOATE, CIS-3- | 25152-85-6 |
| Hexenyl butyrate, cis-3- | 16491-36-4 |
| HEXENYL BUTYRATE, CIS-3- | 16491-36-4 |
| Hexenyl formate, cis-3- | 33467-73-1 |
| Hexenyl hexanoate, cis-3- | 31501-11-8 |
| HEXENYL ISOBUTYRATE, CIS-3- | 41519-23-7 |
| Hexenyl oxacetaldehyde, cis-3- | 68133-79-2 |
| HEXENYL PHENYL ACETATE, CIS-3- | 42436-07-7 |
| Hexenyl phenylacetate, cis-3- | 42436-07-7 |
| Hexenyl propionate, trans-2- | 53398-80-4 |
| HEXENYL PROPIONATE, CIS-3- | 33467-74-2 |
| Hexenyl salicylate, cis-3- | 65405-77-8 |
| HEXENYL TIGLATE, CIS-3- | 67883-79-8 |
| HEXENYL VALERATE, CIS-3- | 35852-46-1 |
| Hexenyl) dihydro-5-methyl-2 (3H) furanone, 5-(cis-3 | 70851-61-5 |
| Hexenylcyclopentanone | 34687-46-2 |
| Hexoxyacetaldehyde dimethyl acetal | 17597-95-4 |
| Hexyl 2-formate | 39251-86-0 |
| Hexyl 2-methylbutyrate | 10032-15-2 |
| HEXYL ACETATE | 142-92-7 |
| HEXYL BENZOATE | 6879-88-4 |
| HEXYL BUTYRATE | 2639-63-6 |
| HEXYL CAPROATE | 6378-65-0 |
| HEXYL CAPRYLATE | 1117-55-1 |
| HEXYL CINNAMALDEHYDE, ALPHA- | 101-86-0 |
| Hexyl crotonate | 19089-92-0 |
| Hexyl ethyl acetoacetate, n- | 29214-60-6 |
| Hexyl formate | 629-33-4 |
| HEXYL HEXANOATE | 6378-65-0 |
| HEXYL ISOBUTYRATE | 2349-07-7 |
| HEXYL ISOVALERATE | 10032-13-0 |
| Hexyl neopentanoate | 5434-57-1 |
| Hexyl phenylacetate | 5421-17-0 |
| Hexyl propionate | 2445-76-3 |
| Hexyl salicylate | 6259-76-3 |
| HEXYL TIGLATE | 16930-96-4 |
| Hexyl-2-decenal, 2- | 13893-39-5 |
| Hexylcyclopentanone, 2- | 13074-65-2 |
| Hexylene glycol | 107-41-5 |
| Hibawood oil | 68917-43-1 |
| Ho leaf oil | 8022-91-1 |
| HOMOPRENYL ISOBUTYRATE | 80118-06-5 |
| Honeysuckle absolute | 8023-93-6 |
| Hyacinth absolute | 8023-94-7 |
| Hydratropic acetate | 10402-52-5 |
| Hydratropic alcohol | 1123-85-9 |
| Hydratropic aldehyde dimethyl acetal | 90-87-9 |
| Hydroabietyl alcohol | 13393-93-6 |
| Hydroxy-2,5-dimethyl-3(2H)-furanone, 4- | 3658-77-3 |
| Hydroxy-2-butanone, 1- | 5077-67-8 |
| Hydroxy-4-methylpentyl)-3-cyclohexene-1carboxaldehyde, 3 and 4-(4- | 31906-04-4 |
| Hydroxyacetophenone, 2'- | 118-93-4 |
| Hydroxybutanoic acid lactone, 4- | 96-48-0 |
| Hydroxycitronellal | 107-75-5 |
| Hydroxycitronellal dimethyl acetal | 141-92-4 |
| Hydroxycitronellal methyl anthranilate | 89-43-0 |
| Hydroxycitronellal-Indole | 68527-79-7 |
| Hydroxycitronellol | 107-74-4 |
| Hydroxydihydrotheaspirane, 6- | 65620-50-0 |
| Hydroxyphenyl)-2-butanone, 4-(p- | 5471-51-2 |
| Hyssop oil | 8006-83-5 |
| Immortelle absolute | 8023-95-8 |
| Indole | 120-72-9 |
| IONOL, ALPHA- | 25312-34-9 |
| Ionol, beta | 22029-76-1 |
| Ionone alpha | 127-41-3 |
| Ionone, beta- | 14901-07-6 |
| Ionyl acetate, alpha | 52210-18-1 |
| IRONE, ALPHA- | 79-69-6 |
| Isoamyl 3-(2-furan)propionate | 7779-67-1 |
| Isoamyl acetate | 123-92-2 |
| Isoamyl acetoacetate | 2308-18-1 |
| Isoamyl alcohol | 123-51-3 |
| ISOAMYL BUTYRATE | 106-27-4 |
| Isoamyl caproate | 2198-61-0 |
| Isoamyl caprylate | 2035-99-6 |
| ISOAMYL FORMATE | 110-45-2 |
| Isoamyl geranate | 68133-73-3 |
| ISOAMYL HEXANOATE | 2198-61-0 |
| Isoamyl isobutyrate | 2050-01-3 |
| ISOAMYL ISOVALERATE | 659-70-1 |
| Isoamyl laurate | 6309-51-9 |
| Isoamyl nonanoate | 7779-70-6 |
| Isoamyl phenylacetate | 102-19-2 |
| ISOAMYL PROPIONATE | 105-68-0 |
| Isoamyl pyruvate | 7779-72-8 |
| ISOAMYL TIGLATE | 41519-18-0 |
| Isoascorbic acid, D- | 89-65-6 |
| Isoborneol | 124-76-5 |
| Isobornyl acetate | 125-12-2 |
| Isobornyl formate | 1200-67-5 |
| Isobornyl methyl ether | 5331-32-8 |
| Isobornyl propionate | 2756-56-1 |
| Isobutyl acetate | 110-19-0 |
| Isobutyl benzoate | 120-50-3 |
| ISOBUTYL BUTYRATE | 539-90-2 |
| Isobutyl caproate | 105-79-3 |
| ISOBUTYL CINNAMATE | 122-67-8 |
| ISOBUTYL FORMATE | 545-55-2 |
| Isobutyl formate | 542-55-2 |
| Isobutyl furylpropionate | 105-01-1 |
| Isobutyl heptylate | 7779-80-8 |
| ISOBUTYL HEXANOATE | 105-79-3 |
| ISOBUTYL ISOBUTYRATE | 97-85-8 |
| Isobutyl isobutyrate | 97-85-8 |
| Isobutyl isovalerate | 589-59-3 |
| Isobutyl linlaool | 56105-46-5 |
| ISOBUTYL PHENYLACETATE | 102-13-6 |
| Isobutyl propionate | 540-42-1 |
| Isobutyl salicylate | 87-19-4 |
| ISOBUTYL TIGLATE | 61692-84-0 |
| Isobutyl trans-2-butenoate | 589-66-2 |
| Isobutyl-3-methoxypryazine, 2- | 24683-00-9 |
| Isobutylthiazole, 2- | 18640-74-9 |
| Isobutyraldehyde | 78-84-2 |
| Isobutyric acid | 79-31-2 |
| Isocamphenyl cyclohexanol | 66068-84-6 |
| Isocyclocitral | 3335-66-6 |
| Isoeugenenyl methyl ether | 93-16-3 |
| Isoeugenol | 97-54-1 |
| Isoeugenyl acetate | 93-29-8 |
| Isoeugenyl phenylacetate | 120-24-1 |
| Isohexenyl cyclohexenyl carboxaldehyde | 37677-14-8 |
| Isojasmone | 11050-62-7 |
| Isoleucine, DL- | 443-79-8 |
| Isolongifolanone | 23787-90-8 |
| Isomenthone | 491-07-6 |
| Isopentylamine | 107-85-7 |
| Isophorone | 78-59-1 |
| Isopropenyl-5-methyl-4-hexen-1-ol, 2 | 498-16-8 |
| Isopropyl 2-methylbutyrate | 66576-71-4 |
| Isopropyl acetate | 108-21-4 |
| Isopropyl alcohol | 67-63-0 |
| Isopropyl butyrate | 638-11-9 |
| Isopropyl cinnamate | 4480-06-5 |
| ISOPROPYL ISOBUTYRATE | 617-50-5 |
| Isopropyl isobutyrate | 617-50-5 |
| Isopropyl myristate | 110-27-0 |
| Isopropyl palmitate | 142-90-6 |
| Isopropyl phenylacetaldehyde, p- | 4395-92-0 |
| Isopropyl phenylacetate | 4861-85-2 |
| Isopropyl quinoline. | 135-79-5 |
| Isopropyl tiglate | 6284-46-4 |
| ISOPROPYL TIGLATE | 1733-25-1 |
| Isopropyl-1-methyl-2-propenylbenzene, 4- | 14374-92-6 |
| Isopropyl-2-(1H)-octahydronaphthalenone | 34131-98-1 |
| Isopropyl-2-decahydronaphthalenol | 34131-99-2 |
| Isopropyl-4-methylthiazole, 2- | 15679-13-7 |
| Isopropyl-5-methyl-2-hexene-1-al, 2- | 35158-25-9 |

TABLE A.1-continued

Database of 1554 odorant components with CAS Numbers

| | |
|---|---|
| Isopropyl-5-methyl-2-hexene-1-ol, 2- | 40853-53-0 |
| Isopropyl-5-methyl-2-hexene-1-yl acetate, 2- | 40853-56-3 |
| Isopropylbenzyl alcohol, p- | 536-60-7 |
| Isopropylcyclohexanol, p- | 4621-04-9 |
| Isopropylphenol, 2- | 88-69-7 |
| Isoproylbenzyl acetate, p- | 59230-57-8 |
| Isopulegol | 89-79-2 |
| Isopulegol acetate | 57576-09-7 |
| Isopulegol | 7786-67-6 |
| Isopulegyl acetate | 57576-09-7 |
| Isoquinoline | 119-65-3 |
| Isosafrole | 120-58-1 |
| Isovaleric acid | 503-74-2 |
| ISOVANILLIN | 621-59-0 |
| JASMIN ACETATE | 18871-14-2 |
| Jasmine absolute | 84776-64-7 |
| Jasmone, cis- | 488-10-8 |
| Jonquil absolute | 8023-75-4 |
| Juniper oil | 8012-91-7 |
| Karo karounds absolute | 68916-95-0 |
| Labdanum oil | 8016-26-0 |
| Lactic acid | 598-82-3 |
| Lactoscatone | 21280-29-5 |
| Laevulinic acid | 123-76-2 |
| Lauric acid | 143-07-7 |
| Lauric aldehyde | 112-54-9 |
| Lauryl alcohol | 112-53-8 |
| Lavandin benzol absolute | 91722-69-9 |
| Lavandin oil | 8022-15-9 |
| Lavandulyl acetate | 25905-14-0 |
| Lavender absolute | 97660-01-0 |
| Lavender oil | 8000-28-0 |
| Lemon oil | 8008-56-8 |
| Lemon petitgrain oil | 8008-56-8 |
| Lemongrass oil | 8007-02-1 |
| Leucine, L- | 61-90-5 |
| Lilial-methyl anthranilate | 91-51-0 |
| Lime oil | 8008-26-2 |
| Limonene, l- | 5989-54-8 |
| Limonene, d- | 5989-27-5 |
| LINALLYL PROPIONATE | 144,39-8 |
| Linaloe wood oil | 8006-86-8 |
| Linalool | 78-70-6 |
| Linalool oxide | 1356-19-1 |
| Linalyl acetate | 115-95-7 |
| Linalyl anthranilate | 7149-26-0 |
| Linalyl butyrate | 78-36-4 |
| Linalyl cinnamate | 78-37-5 |
| Linalyl formate | 115-99-1 |
| Linalyl isobutyrate | 78-35-3 |
| Linalyl isovalerate | 1118-27-0 |
| Linalyl methyl ether | 60763-44-2 |
| Linalyl phenylacetate | 7143-69-3 |
| Linalyl propionate | 144-39-8 |
| Linoleic acid | 60-33-3 |
| *Litsea cubeba* oil | 68855-99-2 |
| Longifolene | 475-20-7 |
| Lovage oil | 8016-31-7 |
| Mace oil | 8007-12-3 |
| Maltol | 118-71-8 |
| MALTOL ISOBUTYRATE | 65416-14-0 |
| Maltyl isobutyrate | 65416-14-0 |
| Mandrin oil | 8008-1-9 |
| Marjoram oil, Spanish | 8016-3-9 |
| Marjoram oil, sweet | 8015-01-8 |
| Mastic absolute | 61789-92-2 |
| *Mentha citrata* oil | 68917-15-7 |
| Menthadiene-7-methyl formate | 6868-20-5 |
| Menthalactone | 13341-72-5 |
| Menthen-6-yl)-1-propanone, 1-(para- | 175-17-4 |
| MENTHOL ISOVALERATE | 16409-46-4 |
| Menthol, 1- | 2216-51-5 |
| Menthol, racemic | 89-78-1 |
| Menthone, racemic | 89-82-5 |
| Menthyl acetate | 16409-45- |
| Menthyl acetoacetate | 59557-05-0 |
| Menthyl lactate, 1- | 61897-98-6 |
| Menthyl phenylacetate, 1- | 26171-78-8 |
| Mercapto-3-butanol, 2- | 37887-04-0 |
| Mercaptopinane, 2,3, and 10- | 23832-18-0 |
| Mercaptopropionic acid | 79-42-5 |
| Methionine, dl- | 59-51-8 |
| Methoxy dicyclopentadiene carboxaldehyde | 8680-90-9 |
| Methoxy-3-(1-methylpropyl)pyrazine, 2- | 24168-70-5 |
| Methoxy-3(5 or 6)-isopropylpyrazine, 2- | 93905-0-4 |
| Methoxy-3-methylpyrazine, 2- | 2847-30-5 |
| Methoxy-4-methylphenol, 2- | 93-51-6 |
| Methoxy-4-vinylphenol, 2- | 7786-61-0 |
| Methoxybenzaldehyde, o- | 135-02-4 |
| METHOXYBENZALDEHYDE, PARA- | 123-11-5 |
| METHOXYCINNAMALDEHYDE, ORTHO- | 1054-74-1 |
| Methoxycitronellal | 3613-30-7 |
| Methoxycoumarin, 7- | 531-59-9 |
| Methoxyhydratropaldehyde, p- | 5462-06-6 |
| Methoxyphenyl) butan-2-one, 4-(p- | 104-20-1 |
| Methoxyphenylacetone | 122-84-9 |
| Methoxypyrazine, 2- | 3149-28-8 |
| Methyl 2-furoate | 611-13-2 |
| METHYL 2-METHYL-BUTYRATE | 868-57-5 |
| Methyl 2-methylbutyrate | 868-87-5 |
| Methyl 2-methylpentanoate | 2177-77-7 |
| Methyl 2-thiofuroate | 13679-61-3 |
| Methyl 3-(methylthio)propionate | 13532-18-8 |
| Methyl 3-hydroxyhexanoate | 21188-58-9 |
| METHYL 3-METHYLTHIO-PROPIONATE | 13532-18-8 |
| Methyl 3-nonenoate | 13481-87-3 |
| Methyl 3-phenylpropionate | 103-25-3 |
| Methyl 4-methylvalerate | 2412-80-8 |
| Methyl abietate | 68189-14-1 |
| METHYL ACETATE | 79-20-9 |
| Methyl acetoacetate | 79-20-9 |
| METHYL ACETOPHENONE, P- | 122-00-9 |
| METHYL AMYL KETONE | 110-43-0 |
| Methyl anisate | 121-98-2 |
| METHYL ANTHRANILATE | 134-20-3 |
| METHYL BENZOATE | 93-58-3 |
| Methyl benzyl carbinyl acetate | 2114--2 |
| METHYL BUTYRATE | 623-42-7 |
| METHYL CAPROATE | 106-70-7 |
| Methyl cinnamate | 103-26-4 |
| Methyl crotonate | 623-43-8 |
| Methyl cyclohexanecarboxylate | 4630-82-4 |
| METHYL CYCLOPENTENOLONE | 80-71-7 |
| METHYL DECALACTONE, GAMMA- | 7011-83-8 |
| METHYL DECANOATE | 110-42-9 |
| METHYL DIHYDROJASMONATE | 24851-98-7 |
| Methyl ester of rosin | 8050-15-5 |
| Methyl ethyl ketone | 78-93-3 |
| METHYL FURFURAL, 5- | 620-02-0 |
| Methyl furfuryl disulfide | 57500-00-2 |
| METHYL FUROATE | 611-13-2 |
| Methyl heptanoate | 106-73-0 |
| Methyl heptenone | 110-93-0 |
| Methyl heptine carbonate | 111-12-6 |
| Methyl hydratropaldehyde, p- | 99-72-9 |
| Methyl isobutrate | 547-63-7 |
| METHYL ISOBUTYRATE | 547-63-7 |
| Methyl isopropyl ketone | 563-80-4 |
| METHYL ISOVALERATE | 556-24-1 |
| Methyl isovalerate | 556-24-1 |
| Methyl jasmonate | 1211-29-6 |
| Methyl laurate | 111-82-0 |
| Methyl linolenate | 301-00-8 |
| METHYL MYRISTATE | 124-10-7 |
| Methyl myristate | 124-10-7 |
| METHYL NAPHTHYL KETONE, ALPHA- | 941-98-0 |
| Methyl naphtyl ketone, beta- | 93-08-3 |
| Methyl nicotinate | 93-60-7 |
| Methyl N-methylanthranilate | 85-91-6 |
| Methyl nonanoate | 1731-84-6 |
| Methyl nonyl ketone | 112-12-9 |
| Methyl nonylenate | 111-79-5 |
| METHYL OCTANOATE | 111-11-5 |
| Methyl octine carbonate | 111-80-8 |
| Methyl octyl acetaldehyde | 19009-56-4 |
| Methyl o-methoxybenzoate | 606-45-1 |

TABLE A.1-continued

Database of 1554 odorant components with CAS Numbers

| Name | CAS |
|---|---|
| METHYL PENTANOIC ACID, 3- | 97-61-0 |
| METHYL PHENYL ACETATE | 101-41-7 |
| METHYL PHENYL CARBINYL PROPIONATE | 120-45-6 |
| Methyl p-hydroxybenzoate | 99-76-3 |
| METHYL PROPIONATE | 554-12-1 |
| Methyl propyl disulfide | 2179-60-4 |
| Methyl p-tert-butylphenylacetate | 3549-23-3 |
| Methyl p-tolulate | 99-75-2 |
| METHYL QUINOLINE, 6- | 91-62-2 |
| Methyl salicylate | 119-36-8 |
| Methyl sorbate | 689-89-4 |
| Methyl sulfide | 75-18-3 |
| Methyl thiobutyrate | 2432-51-1 |
| Methyl tiglate | 6622-76-0 |
| Methyl trans-2-octenoate | 7367-81-9 |
| METHYL TRANS-2-OCTENOATE | 7367-81-9 |
| Methyl undecylenate | 5760-50-9 |
| Methyl valerate | 624-24-8 |
| Methyl-1,2-cyclohexanedione, 3- | 3008-43-3 |
| Methyl-1-octen-3-ol, 3- | 24089-00-7 |
| Methyl-1-pentanol, 3- | 589-5-5 |
| Methyl-1-phenyl-2-pentanone, 4- | 5349-62-2 |
| Methyl-2(3)-nonenenitrile, 3- | 53153-66-5 |
| Methyl-2,6-dimethoxyphenol, 4- | 6638-05-7 |
| Methyl-2-butanol, dl-3- | 598-75-4 |
| Methyl-2-butenal, 3- | 107-86-8 |
| Methyl-2-butenal, trans-2- | 497-03-0 |
| Methyl-2-butenyl salicylate, 3- | 68555-58-8 |
| Methyl-2-cyclohexen-1-one, 3- | 1193-18-6 |
| Methyl-2-cyclopenten-1-one, 3- | 2758-18-1 |
| Methyl-2-fury)butanal, 3-(5- | 31704-80-0 |
| Methyl-2-pentanone, 4- | 108-10-1 |
| Methyl-2-pentenal, 2- | 623-36-9 |
| METHYL-2-PENTENAL, trans-2- | 623-36-9 |
| Methyl-2-pentenoic acid, 2- | 16957-70-3 |
| METHYL-2-PENTENOIC ACID, trans-2- | 16957-70-3 |
| Methyl-2-phenyl-2-hexenal, 5- | 21834-92-4 |
| Methyl-2-phenyl-2-pentenal, 4- | 26643-91-4 |
| Methyl-2-thiophenecarboxaldehyde, 5- | 13679-70-4 |
| Methyl-3-(p-isopropylphenyl) propionaldehyde, 2- | 103-95-7 |
| Methyl-3,(5 or 6)-ethoxypyrazine, 2- | 32737-14-7 |
| Methyl-3-butyltetrahydropyran-4-yl acetate, 5- | 96-17-3 |
| Methyl-3-furanthiol, 2- | 28588-74-1 |
| Methyl-3-heptanone oxime, 5- | 22457-23-4 |
| Methyl-3-penten-2-one, 4- | 141-79-7 |
| METHYL-4-PENTENOIC ACID, 2- | 1575-74-2 |
| Methyl-4-phenyl-2butanol, 2- | 103-05-9 |
| METHYL-4-PROPYL-1,3-OXATHIANE, 2- | 67715-80-4 |
| METHYL-5-(METHYLTHIO)-FURAN, 2- | 13678-59-6 |
| METHYL-5-THIAZOLE ETHANOLACETATE, 4- | 656-53-1 |
| Methyl-5-thiazoleethanol acetate, 4- | 656-53-1 |
| Methyl-5-thiazoleethanol, 4- | 137-00-8 |
| METHYL-5-THIAZOLE-ETHANOL, 4- | 137-00-8 |
| Methyl-5-vinylthiazole, 4- | 1759-28-0 |
| METHYL-5-VINYL-THIAZOLE, 4- | 1759-28-0 |
| Methyl-6,7-dihydrocyclopenta(b)-pyrazine, 5H-5- | 23747-48-0 |
| Methylanisalacetone, alpha- | 104-27-8 |
| Methylanisole, 2- | 578-58-5 |
| Methylbenzyl acetate, 4- | 2216-45-7 |
| METHYLBENZYL ACETATE, ALPHA | 93-92-5 |
| Methylbenzyl butyrate, alpha- | 3460-44-4 |
| Methylbiphenyl, 4- | 644-08-6 |
| Methylbuty acetate, 2- | 53496-15-4 |
| Methylbutyl 2-methylbutyrate, 2- | 2445-78-5 |
| Methylbutyl isovalerate, 2- | 2445-77-4 |
| Methylbutyraldehyde, 3- | 590-86-3 |
| Methylbutyric acid | 600-07-7 |
| Methylcinnamic alcohol, alpha | 1504-55-8 |
| METHYLCINNAMIC ALDEHYDE, ALPHA- | 101-39-3 |
| Methylcoumarin, 6- | 92-48-8 |
| Methylcoumarin, 7- | 2445-8-2 |
| Methylcrotonic, 3- | 541-47-9 |
| Methylcyclododecyl methyl ether, 1- | 37514-30-0 |
| Methylcyclooctyl carbonate | 61699-38-5 |
| Methylcyclopentadecanone, 3- | 541-91-3 |
| Methylheptanoic acid, 2- | 1188-02-9 |
| Methylheptenol | 1335-09-7 |
| Methylhexlacetaldehyde | 7786-29-0 |
| Methylionol, alpha- | 70172-00-8 |
| Methylnaphthalene, 1- | 90-12-0 |
| Methylnonanoic acid, 4- | 45019-28-1 |
| Methyloctan-3-ol, 3- | 540-36-3 |
| Methyloctanoic acid, 4- | 54947-74-9 |
| Methylpentanal, 2- | 123-15-9 |
| Methylpentanoic acid, 4- | 646-07-1 |
| METHYLPHENOXY ACETALDEHYDE, p- | 67845-46-9 |
| Methylpropyl)thiazole, 2-(1- | 18277-27-5 |
| Methylpyrazine, (Methylthio)- | 67952-65-2 |
| Methylpyrazine, 2- | 109-08-0 |
| Methylquinoxaline, 5- | 13708-12-8 |
| Methyltetrahydrofuran-3-one, 2- | 3188-00-9 |
| Methyltetrahydrothiophen-3-one, 2- | 13679-85-1 |
| Methylthiazole, 4- | 693-95-8 |
| Methylthio)-1-hexanol, 3-( | 51755-66-9 |
| Methylthio)butanal, 3-( | 16630-52-7 |
| Methylthio)butanol, 4-( | 20582-85-8 |
| METHYLTHIO-1-HEXANOL, 3- | 5155-66-9 |
| Methylthio-2-butanone, 4- | 34047-39-7 |
| Methylthio-4-methyl-2-pentanone, 4- | 23550-40-5 |
| Mimosa absolute | 93685-96-2 |
| Musk amberette | 83-66-9 |
| Musk tibetene | 145-39-1 |
| Musk tonquin tincture | 8001-04-5 |
| Musk xylol | 81-15-2 |
| Mycernol | 543-39-5 |
| MYRCENE | 123-35-3 |
| Myrcenyl acetate | 1118-39-4 |
| Myristic acid | 554-63-8 |
| Myrrh absolute | 8016-37-3 |
| MYRTENOL | 515-00-4 |
| Myrtenyl acetate | 1079-01-2 |
| Myrtle oil | 8008-46-6 |
| Naphthalenethiol, 2- | 9160-1 |
| Naphthyl ethyl ether, beta- | 93-18-5 |
| Naphthyl isobutyl ether | 2173-57-1 |
| Naphthyl methyl ether, beta | 93-04-9 |
| NEOHESPERIDIN DIHYDROCHALCONE (NHDC) | 20702-77-6 |
| Neomenthol, d- | 2216-52-6 |
| NEROL | 106-25-2 |
| Nerol oxide | 1786-08-9 |
| Neroli oil | 8016-38-4 |
| Nerolidol | 7212-44-4 |
| Nerolidyl acetate | 56001-43-5 |
| NERYL ACETATE | 141-12-8 |
| Neryl butyrate | 999-40-6 |
| Neryl formate | 2142-94-1 |
| NERYL ISOBUTYRATE | 2345-24-6 |
| Neryl isovalerate | 3915-83-1 |
| NERYL PROPIONATE | 105-91-9 |
| Nonadienal, 2,6- | 557-48-2 |
| Nonadienal, trans, trans-2,4- | 5910-87-2 |
| NONADIENAL, trans,trans-2,4- | 6750-03-4 |
| Nonadienol, 2,6- | 7786-44-9 |
| NONALACTONE, DELTA- | 3301-94-8 |
| NONALACTONE, GAMMA- | 104-61-0 |
| NONANAL | 124-19-6 |
| NONANEDIOL ACETATE, 1,3- | 1322-17-4 |
| Nonanedithiol, 1,9- | 3489-28-9 |
| Nonanol, 2- | 628-99-9 |
| NONANONE, 2- | 821-55-6 |
| Nonanone, 3- | 925-78-0 |
| Nonatrien-2-one, 3,5,7- | 17609-32-4 |
| Nonen-1-ol, cis- | 41453-56-9 |
| Nonen-1-ol, cis-6- | 35854-86-5 |
| Nonenal, 2- | 2463-53-8 |
| NONENAL, cis-6- | 2277-19-2 |
| NONENAL, trans-2- | 18829-56-6 |
| NONENOL, cis-6- | 35854-86-5 |
| Nonyn-1-al dimethylacetal, 2- | 13257-44-8 |
| NOOTKATONE EX VALENCENE | 46674-50-4 |
| Nopol | 128-50-7 |
| Nopyl acetate | 128-51-8 |
| Nutmeg oil | 8008-45-5 |
| Oakmoss resinoid | 9000-50-4 |
| Ocimene | 13877-91-3 |

TABLE A.1-continued

Database of 1554 odorant components with CAS Numbers

| | |
|---|---|
| OCIMENOL | 5986-38-9 |
| Ocimenol acetate | 72214-23-4 |
| *Ocotea cymbarum* oil | 68917-09-9 |
| Octadienal, 2,4- | 5577-44-6 |
| OCTADIENAL, trans,trans-2,4- | 5577-44-6 |
| Octahydrocoumarin | 4430-31-3 |
| Octahydrocoumarin | 4430-31-3 |
| OCTALACTONE, DELTA- | 698-76-0 |
| OCTALACTONE, GAMMA- | 104-50-7 |
| OCTANAL | 124-13-0 |
| Octanedithiol, 1,8 | 1191-62-4 |
| OCTANOL, 1- | 111-87-5 |
| OCTANOL, 3- | 598-98-0 |
| OCTANONE, 2- | 111-13-7 |
| Octen-1-ol, cis-5- | 64275-73-6 |
| Octen-2-one, 3- | 1669-44-9 |
| Octenal, trans-2- | 2363-89-5 |
| OCTENAL, trans-2- | 2363-89-5 |
| Octyl 2-furoate | 39251-88-2 |
| Octyl acetate, 3- | 4864-61-3 |
| Octyl butyrate | 110-39-4 |
| Octyl formate | 112-32-3 |
| OCTYL ISOBUTYRATE | 109-15-9 |
| OCTYL ISOVALERATE | 7786-58-5 |
| Octyl isovalerate | 7786-58-5 |
| Octyl salicylate | 6969-49-9 |
| Oleic acid | 112-80-1 |
| Olibanum absolute | 8016-36-2 |
| Orange flower absolute | 8030-28-2 |
| Orange oil expressed | 8008-57-9 |
| *Origanum* oil | 8007-11-2 |
| Orris absolute | 8002-73-1 |
| Oxahexadecanolide, 10- | 1725-01-5 |
| Oxahexadecanolide, 11- | 3391-83-1 |
| OXAHEXADECANOLIDE, 12- | 6707-60-4 |
| Oxoisophorone, 4- | 1125-21-9 |
| Oxybutyric acid, 2- | 600-18-0 |
| Palmarosa oil | 8014-19-5 |
| Palmitic acid | 57-10-3 |
| Parsley herb oil | 8000-68-8 |
| Patchouly oil | 8014-09-3 |
| PELARGONIC ACID | 112-05-0 |
| Pennyroyal oil | 801-99-8 |
| Pentamethyl-4,6-dinitroindane | 116-66-5 |
| Pentanol, 2- | 6032-29-7 |
| Pentanone, 2- | 107-87-9 |
| Penten-2-one, 3- | 625-33-2 |
| Penten-3-ol, 1- | 616-25-1 |
| Pentenal, trans-2- | 1576-87-0 |
| Pentenoic acid, 4- | 591-80-0 |
| Pentyl 2-furyl ketone | 14360-50-0 |
| Pentyl cyclpentanone propanone | 40942-73-2 |
| Pentylfuran, 2- | 3777-69-3 |
| Pentylidene cyclohexanone | 256677-40-1 |
| Pentylpyridine, 2- | 2294-76-0 |
| Pepper, black oil | 8006-82-4 |
| *PERILLA* ALCOHOL | 536-59-4 |
| *Perilla* oil | 6812-21-8 |
| PERILLALDEHYDE | 2111-75-3 |
| Peru balsam oil | 8007-00-9 |
| Petigrain bigarade oil | 8014-17-3 |
| PHELLANDRENE, alpha | 99-83-2 |
| Phenethyl 2- furoate | 7149-32-8 |
| Phenethyl hexanoate | 6290-37-5 |
| Phenethyl octanoate | 5457-70-5 |
| Phenethylamine | 64-04-0 |
| Phenol | 108-95-2 |
| PHENOXY ACETALDEHYDE | 2120-70-9 |
| Phenoxyacetic acid | 122-59-8 |
| Phenoxyethyl isobutyrate | 103-60-6 |
| Phenoxyethyl propionate, 2- | 23495-12-7 |
| Phenthyl isobutyrate | 103-48-0 |
| PHENYL ACETALDEHYDE | 122-78-1 |
| Phenyl acetyl nitrile | 140-29-4 |
| Phenyl anisole, o- | 86-26-0 |
| Phenyl disulfide | 882-33-7 |
| PHENYL ETHYL ALCOHOL | 60-12-8 |
| PHENYL ETHYL BENZOATE, 2- | 94-47-3 |
| PHENYL ETHYL BUTYRATE, 2- | 103-52-6 |
| PHENYL ETHYL CINNAMATE, 2- | 103-53-7 |
| PHENYL ETHYL FORMATE, 2- | 104-62-1 |
| PHENYL PROPYL ALDEHYDE | 122-97-4 |
| Phenyl salicylate | 118-55-8 |
| Phenyl-1,2-propanedione, 1- | 579-07-7 |
| Phenyl-1-pentanol, 5- | 10521-91-2 |
| Phenyl-1-propanol, 1- | 93-54-9 |
| Phenyl-2-pentanol, 1- | 705-73-7 |
| Phenylacetaldehyde 2,4-dihydroxy-2-methylpentane acetal | 67633-94-7 |
| PHENYLACETALDEHYDE DIISOBUTYL-ACETAL(PADIBA) | 6834-22-2 |
| Phenylacetaldehyde dimethyl acetal | 101-48-4 |
| Phenylacetaldehyde glyceryl acetal | 29895-73-6 |
| Phenylacetic acid | 103-82-2 |
| Phenylalanine, DL- | 150-0-1 |
| Phenylalanine, L- | 6-91-2 |
| Phenylethyl 2-methylbutyrate | 24817-51-4 |
| Phenylethyl acetate | 103-45-7 |
| Phenylethyl anthranilate | 133-18-6 |
| PHENYLETHYL HEXANOATE | 6290-37-5 |
| Phenylethyl isoamyl ether | 56011-02-0 |
| Phenylethyl isovalerate | 140-26-1 |
| PHENYLETHYL ISOVALERATE | 140-26-1 |
| Phenylethyl methacrylate | 3683-12-3 |
| Phenylethyl methyl ether | 3558-60-9 |
| Phenylethyl methyl ethyl carbinol | 10415-87-9 |
| Phenylethyl methyl ethyl carbinol acetate | 72007-81-9 |
| Phenylethyl phenylacetate | 102-20-5 |
| PHENYLETHYL PIVALATE | 67662-96-8 |
| Phenylethyl propionate | 122-70-3 |
| Phenylethyl salicylate | 87-22-9 |
| Phenylethyl tiglate | 55719-85-2 |
| PHENYLETHYL TIGLATE | 55719-85-2 |
| Phenylpropionaldehyde, 2- | 93-53-8 |
| Phenylpropionaldehyde, 3- | 104-53-0 |
| Phenylpropionic acid, 3- | 501-52-0 |
| Phenylpropyl acetate | 122-72-5 |
| Phenylpropyl butyrate, 2- | 80866-83-7 |
| Phenylpropyl formate | 104-64-3 |
| Phenylpropyl isobutyrate, 2- | 65813-53-8 |
| Phenylpropyl isobutyrate, 2- | 65813-53-8 |
| Phenylpropyl isobutyrate, 3- | 103-58-2 |
| Phenylpropyl isovalerate, 3- | 5452-07-3 |
| Phenylpropyl propionate | 122-74-7 |
| Phenylpropyl)pyridine, 2-(3- | 2110-18-8 |
| Phytol | 150-86-7 |
| *Pimenta* berry oil | 8006-77-7 |
| *Pimenta* leaf oil | 8016-45-3 |
| Pinacol | 76-09-5 |
| Pinacol | 76-09-5 |
| Pinanol, cis-2- | 4948-28-1 |
| Pinene, (1S)-(1)-alpha- | 7785-26-4 |
| Pinene, (1S)-(1)-beta- | 18172-67-3 |
| Pinene, alpha- | 80-56-8 |
| PINENE, BETA- | 127-91-3 |
| *Pinus pumilio* oil | 8000-26-8 |
| *Pinus sylvestris* oil | 8023-99-2 |
| Piperidine | 110-89-4 |
| Piperine | 94-62-2 |
| PIPERITENONE | 89-81-6 |
| Piperonal | 120-57-0 |
| Piperonyl acetate | 326-61-4 |
| Piperonyl acetone | 55418-52-5 |
| Piperonyl isobutyrate | 5461-08-5 |
| PRENOL | 556-82-1 |
| Prenyl acetate | 1191-16-8 |
| PRENYL BENZOATE | 5205-11-8 |
| Propanedithiol, 1,3- | 109-80-8 |
| Propanol, 1- | 71-23-8 |
| Propenoic acid, 3-phenyl-, 3-phenylpropyl ester, 2- | 122-68-9 |
| Propionaldehyde | 123-38-6 |
| Propionic acid | 79-09-4 |
| Propiophenone | 93-55-0 |
| Propyl hexanoate | 626-77-7 |
| Propyl acetal, n- | 105-82-8 |

TABLE A.1-continued
Database of 1554 odorant components with CAS Numbers

| Name | CAS |
|---|---|
| Propyl acetate | 109-60-4 |
| Propyl butyrate | 105-66-8 |
| Propyl disulfide | 629-19-6 |
| Propyl formate | 110-74-7 |
| Propyl heptanoate | 7778-87-2 |
| PROPYL HEXANOATE | 626-77-7 |
| Propyl isobutyrate | 644-49-5 |
| Propyl mercaptan | 107-03-9 |
| Propyl phenylacetate | 4606-15-9 |
| PROPYL PROPIONATE | 106-36-5 |
| Propylbicyclo[2.2.1]hept-5-ene-2-carboxaldehyde | 39067-39-5 |
| Propylene glycol | 57-55-6 |
| PROPYLIDENE PHTHALIDE | 17369-59-4 |
| Propylidenephthalide, 3- | 17369-59-4 |
| Propyphenol, 2- | 644-5-9 |
| Propyphenol, 4- | 645-56-7 |
| Pulegone, (R)-(+)- | 89-82-7 |
| PULEGONE, d- | 89-82-7 |
| Pyrazineethanethiol | 35250-5-4 |
| Pyridine | 110-86-1 |
| Pyrrole | 109-97-7 |
| Pyrrolidine | 123-75-1 |
| Pyruvaldehyde | 78-98-8 |
| Pyruvic acid | 127-17-3 |
| Quinoline | 91-22-5 |
| RASPBERRY KETONE | 5471-51-2 |
| RASPBERRY KETONE METHYL ETHER | 104-20-1 |
| RESEDOLAN Phenylacetaldehyde hexylene | 67633-94-7 |
| Resorcinol | 108-46-3 |
| Rhodinol | 6812-78-8 |
| RHODINYL ACETATE | 141-11-7 |
| Rhodinyl butyrate | 141-15-1 |
| RHODINYL FORMATE | 141-09-3 |
| RHODINYL ISOBUTYRATE | 138-23-8 |
| Rhodinyl phenylacetate | 10486-14- |
| Rhodinyl propionate | 105-89-5 |
| Ribose, D- | 50-69-1 |
| Rose absolute | 8007-01-0 |
| Rose oil | 8007-01-0 |
| ROSE OXIDE (High Cis) | 16409-43-1 |
| Rose oxide, levo | 3033-23-6 |
| Rosemary oil | 8000-25-7 |
| Rue oil | 8014-29-7 |
| Safranal | 116-26-7 |
| Safrole | 94-59-7 |
| Sage Dalmatian oil | 8016-64-6 |
| Sage oil | 8016-65-7 |
| SALICYLALDEHYDE | 90-02-8 |
| Sandlewood oil | 8006-87-9 |
| SANTALOL, ALPHA, BETA- | 115-71-9 |
| Santalyl acetate | 1323-00-8 |
| *Sassafras* oil | 8006-80-2 |
| Savory summer oil | 8016-68-0 |
| *Schinus molle* oil | 68917-52-2 |
| Sclareol | 515-03-7 |
| Skatole | 83-34-1 |
| Snakeroot oil | 8016-69-1 |
| Sodium acetate | 127-09-3 |
| Sodium Benzoate | 532-32-1 |
| Sorbitan monostearate | 1338-41-6 |
| Sorbitol, D- | 50-70-4 |
| Spearmint oil | 8008-79-5 |
| Spike lavender oil | 8016-78-2 |
| Spruce oil | 8008-80-8 |
| Star anise oil | 8007-70- |
| Stearic acid | 57-11-4 |
| Styralyl alcohol | 98-85-1 |
| Styrene | 100-42-5 |
| Sucrose octaacetate | 126-14-7 |
| Sweet birch oil | 68917-50-0 |
| *Tagetes* oil | 8016-84-0 |
| Tangelo oil | 72869-73-9 |
| Tangerine oil | 8008-31-9 |
| Tansy oil | 8016-87-3 |
| Tatatric acid, L-(+)- | 87-69-4 |
| Tea tree oil | 68647-73-4 |
| TERPENYL FORMATE | 2153-26-6 |
| TERPINENE, ALPHA- | 99-86-5 |
| TERPINENE, GAMMA- | 99-85-4 |
| Terpineol | 8000-41-7 |
| Terpineol, alpha- | 10482-56-1 |
| TERPINOLENE | 586-62-9 |
| TERPINYL ACETATE | 8026-2 |
| Terpinyl isobutyrate | 7774-65-4 |
| TERPINYL PROPIONATE | 80-27-3 |
| Terpnyl formate | 2153-26-3 |
| Tetradecalactone | 2721-22-4 |
| Tetrahydro-3,6-dimethyl-benzofuran, 4,5,6,7- | 494-90-6 |
| Tetrahydro-4-methyl-2-(2-methylpropen-1-yl)pyran | 16409-43-1 |
| Tetrahydrofurfuryl acetate | 637-64-9 |
| Tetrahydrofurfuryl alcohol | 97-99-4 |
| Tetrahydrofurfuryl butyrate | 92345-48-7 |
| Tetrahydrogeranial | 5988-91-0 |
| Tetrahydrogeranyl acetate | 20780-48-7 |
| Tetrahydrolinalool | 78-69-3 |
| TETRAHYDROMUGUOL | 41678-36-8 |
| Tetrahydroquinoxaline, 5,6,7,8- | 34413-35-9 |
| Tetramethyl-4-ethoxyvinylcyclohexanone, 3,3,5,5- | 36306-87-3 |
| Tetramethypyrazine, 2,3,5,6- | 1124-11-4 |
| Tetrohydrofurfuryl propionate, dl- | 637-65-0 |
| Theaspirane | 36431-72-8 |
| Thiamine hydrochloride | 67-03-8 |
| Thiazole | 288-47-1 |
| Thienyl disulfide, 2- | 6911-51-9 |
| Thiophenethiol | 7774-74-5 |
| Thyme oil | 8007-46-3 |
| Thymol | 89-83-8 |
| THYMYL ACETATE | 528-79-0 |
| THYMYL METHYL ETHER | 1076-56-8 |
| TIGLIC ACID | 80-59-1 |
| Tobacco leaf absolute | 8037-19-2 |
| Tolu, balsam, gum | 9000-64-0 |
| Tolualdehyde glyceryl acetal | 1333-09-1 |
| Toluenethiol, o- | 137-06-4 |
| TOLUIC ALDEHYDE (MIXED 2, 3, 4) | 1334-78-7 |
| TOLYL ACETALDEHYDE, PARA- | 104-09-6 |
| TOLYL ACETATE, PARA- | 140-39-6 |
| Tolyl alcohol, p- | 589-18-4 |
| Tolyl isobutyrate, o- | 36438-54-7 |
| TOLYL PHENYL ACETATE, PARA- | 101-94-0 |
| Tonka absolute | 8046-22-8 |
| Treemoss concrete | 68648-41-9 |
| TRIACETIN | 102-76-1 |
| Tributyl acetylcitrate | 77-90-7 |
| Tributyrin | 60-01-5 |
| Trichloromethyl phenyl carbinyl acetate | 90-17-5 |
| Tricyclodecen-4-yl 8-acetate | 5413-60-5 |
| Tricyclodecenyl propionate | 17511-60-3 |
| Tricyclodecylidene butanal | 30168-23-1 |
| Tridecanone, 2- | 59-08-8 |
| TRIDECENAL, 2- | 7774-82-5 |
| Triethyl citrate | 77-93-0 |
| Triethyl orthoformate | 122-51-0 |
| Triethyleneglycol | 112-27-6 |
| Trimethy-3,5,9-undecatrien-2-one, 3,6,10- | 1117-41-5 |
| Trimethyl-1-cyclohexene-1-acetaldehyde, 2,6,6- | 472-66-2 |
| Trimethyl-1-hexanol, 3,5,5- | 452-97-9 |
| Trimethyl-2-cyclohexen)-2-methylbutanal, 4-(2,6,6- | 65405-84-7 |
| Trimethyl-2-cyclohexen-1-yl)-3-buten-2-one, 4-(2,4,6- | 67801-38-1 |
| Trimethyl-9-undecenal, 2,6,10- | 141-13-9 |
| Trimethylamine | 75-50-3 |
| Trimethylbenzyl alcohol, p,alpha,alpha | 1197-01-9 |
| Trimethylcyclohexanol acetate, 3,5,5- | 58430-94-7 |
| Trimethylcyclohexanol, 3,5,5- | 116-02-9 |
| Trimethylcyclohexanone, 2,2,6- | 2408-7-9 |
| Trimethylhexanal, 3,5,5- | 545-64- |
| Trimethylpyrazine, 2,3,5- | 14667-55-1 |
| Trimethylthiazole, 2,4,5- | 1623-11-5 |
| Tripropionin | 139-45-7 |

TABLE A.1-continued

Database of 1554 odorant components with CAS Numbers

| Name | CAS |
|---|---|
| Trithioacetone | 828-26-2 |
| Tyrosine, L- | 60-18-4 |
| Undecalactone, delta- | 710-04-3 |
| Undecalactone, gamma- | 104-67-6 |
| Undecanal | 112-44-7 |
| Undecane | 1120-21-4 |
| Undecanoic acid | 112-37-8 |
| Undecatriene, 1,3,5- | 16356-11-9 |
| Undecenal, trans-2- | 53448-07-0 |
| Undecylenic acid | 112-38-9 |
| Undecylenic aldehyde digeranyl acetal | 67785-74-4 |
| Valeraldehyde, n- | 110-62-3 |
| Valeric acid | 109-52-4 |
| Valerolactone, gamma-- | 108-29-2 |
| Valine, dl- | 516-06-3 |
| Valine, dl- | 516-06-3 |
| Vanilla tincture | 8047-24-3 |
| VANILLIC ACID | 121-34-6 |
| Vanillin | 121-33-5 |
| VANILLIN ACETATE | 881-68-5 |
| Vanillin isobutyrate | 20665-85-4 |
| Vanillin propylene glycol acetal | 68527-74-2 |
| VANILLYL ACETONE | 122-48-5 |
| VANILLYL ALCOHOL | 498-00-0 |
| Vanillyl butyl ether | 82654-98-6 |
| Veratraldehyde | 120-14-9 |
| Veratrole | 91-16-7 |
| *Verbena* absolute | 8024-12-2 |
| VERBENONE, (1S)-(−)- | 1196-01-6 |
| Vetiver acetate | 117-98-6 |
| Vetiver oil | 8016-96-4 |
| Vetiverol | 89-88-3 |
| Vinylphenol, 4- | 2628-17-3 |
| Violet leaf absolute | 9047-36-7 |
| Whiskey lactone | 39212-23-2 |
| Xylenol, 2,4- | 105-67-9 |
| Xylenol, 2,5- | 95-87-4 |
| Xylenol, 2,6- | 576-26-1 |
| Xylenol, 3,4- | 95-65-8 |
| Xylose, d- | 58-86-6 |
| Yarmor pine oil | 8002-09-3 |
| Ylang ylang oil | 8006-81-3 |
| Zingerone | 122-48-5 |

TABLE A.2

Database of 138 odorant components CAS and CID Numbers (duplicate entries correspond to different odor intensity)

| CAS | CID | NAME |
|---|---|---|
| 698-10-2 | 61199 | Abhexone |
| 98-86-2 | 7410 | Acetophenone |
| 1122-62-9 | 14286 | ortho-Acetyl pyridine |
| 141-13-9 | 98403 | Adoxal |
| 77-83-8 | 6501 | Aldehyde c-16 (Lower)-glycidate |
| 77-83-8 | 6501 | Aldehyde c-16 (Higher)-glycidate |
| 104-61-0 | 7710 | gamma-nonalactone |
| 123-68-2 | 31266 | Allyl hexanoate |
| 123-82-2 | 31276 | amyl acetate: iso-amyl acetate |
| 540-18-1 | 10890 | amyl butyrate |
| 60763-41-9 | 108505 | amyl cinnamic aldehyde diethyl acetal |
| 102-19-2 | 7600 | iso-pentyl phenyl acetate |
| 2173-56-0 | 62433 | pentyl valerate |
| 29597-36-2 and 13567-39-0 | 122510 | andrane |
| 104-46-1 | 637563 | anethole |
| 100-66-3 | 7519 | anisole |
| 89-43-0 | 98118 | Auralva-Methyl N-(3 |
| 100-52-7 | 240 | Benzaldehyde |
| 119-84-8 | 660 | benzo dihydro pyrone |
| 5655-61-8 | 93009 | bornyl acetate: iso-bornyl acetate |
| 107-92-6 | 264 | butanoic acid |
| 71-38-3 | 263 | butanol: 1-butanol |
| 544-40-1 | 11002 | butyl sulfide |
| 67634-06-4 | 106734 | butyl quinoline: iso-butyl quinoline |
| 78-22-2 | 2537 | camphor dl-camphor |
| 99-49-0 | 439570 | carvone: i- carvone |
| 87-44-5 and 118-65-0 | 5281515 | caryophyllene |
| 33704-61-9 | 92292 | cashmeran |
| 17369-59-4 | 6259976 | celeriax |
| 89-68-9 | 6982 | chlorothymol |
| 104-55-2 | 307 | cinnamic aldehyde |
| 141-27-5 | 638011 | citral |
| 5585-39-7 | 21768 | citralva |
| 91-64-5 | 323 | coumarin |
| 108-39-4 | 342 | cresol:m-cresol |
| 106-44-5 | 2879 | p-Cresol |
| 140-39-6 | 8797 | cresyl acetate: p-cresyl acetate: p-tolyl ester |
| 103-93-5 | 7685 | cresyl butyrate: p-cresyl-iso-butyrate: P-tolyl ester |
| 104-93-8 | 7731 | cresyl methyl ether: 4-methyl anisole |
| 122-03-2 | 326 | cuminic aldehyde |
| 1423-46-7 | 101150 | cyclocitral: iso-cyclocitral |
| 55704-78-4 | 62105 | cyclodithalfarol |
| 765-87-7 | 13006 | cyclohexanedione |
| 108-93-0 | 7966 | cyclohexanol |
| 80-71-7 | 6660 | cyclotene |
| 67634-23-5 | 236687 | cyclotropal |
| 25152-84-5 | 5283349 | decadienal: 2 |
| 91-17-8 | 7044 | decahydro naphthalene |
| 111-92-2 | 8148 | dibutyl amine |
| 352-93-2 | 9609 | diethyl sulfide |
| 10094-34-5 | 24915 | dimethyl benzyl carbinyl butyrate |
| 103-05-9 | 7632 | dimethyl phenyl ethyl carbinol |
| 5910-89-4 | 22201 | Dimethyl Pyrazine: 2 |
| 123-32-0 | 31252 | Dimethyl Pyrazine: 2 |
| 625-84-3 | 12265 | dimethyl pyrrole: 2 |
| 3658-80-8 | 19310 | Dimethyl trisulfide |
| 03-07-47 | 78484 | diola |
| 101-84-8 | 7583 | Diphenyl Oxide |
| 105-54-4 | 7762 | ethyl butyrate |
| 105-37-3 | 7749 | ethyl propionate |
| 13925-00-3 | 26331 | 2-ethyl pyrazine (low concentration) |
| 13925-00-3 | 26331 | 2-ethyl pyrazine (higher concentration) |
| 470-82-6 | 2758 | eucalyptol |
| 97-53-0 | 3314 | eugenol |
| 67634-15-5 | 105513 | floralozone |
| 01-10-13 | 80865 | fructone |
| 98-01-1 | 7362 | furfural |
| 98-02-2 | 7363 | furfuryl mercaptan |
| 88683-93-6 | | grisalva |
| 90-05-1 | 460 | Guaiacol |
| 111-71-7 | 8130 | Heptanal |
| 111-70-6 | 8129 | 1-heptanol |
| 66-25-1 | 6184 | hexanal |
| 142-62-1 | 8892 | hexanoic acid |
| 111-27-3 | 8103 | 1-hexanol |
| 623-37-0 | 12178 | 3-Hexanol |
| 6728-26-3 | 5281168 | trans-1-Hexanal |
| 111-26-2 | 8102 | hexyl amine (lower concen) |
| 111-26-2 | 8102 | hexyl amine (higher concen) |
| 101-86-0 | 1550884 | hexyl cinnamic aldehyde |
| 90-87-2 | 62336 | Hydratropic Aldehyde Dimethyl Acetate |
| 107-75-5 | 7888 | hydroxy Citronellal |
| 120-72-9 | 798 | Indole |
| 67801-36-9 | 106826 | indolene |
| 75-47-8 | 6374 | iodoform |
| 14901-07-6 | 638014 | ionone: beta-ionone (lower con) |
| 14901-07-6 | 638014 | ionone: beta-ionone (higher con) |
| 79-69-6 | 5371002 | irone: alpha-Irone |
| 126-91-0 | 443158 | linalool |
| 138-86-3 | 22311 | limonene: d-Limonene |
| 31906-04-4 | 91604 | lyral |
| 672558-87-1 | | maritima |
| 106-72-9 | 61016 | melonal |
| 2216-51-5 | 16666 | menthol: 1-Menthol |
| | | methoxy-naphthalene: 2-Methoxy |

TABLE A.2-continued

Database of 138 odorant components CAS and CID Numbers (duplicate entries correspond to different odor intensity)

| CAS | CID | NAME |
|---|---|---|
| 93-04-9 | 7119 | Naphthalene |
| 134-20-3 | 8635 | methyl anthranilate |
| 4744-10-9 | 20859 | methyl acetaldehyde dimethyl acetal |
| 1334-76-5 | 14918 | methyl furoate |
| 2371-42-8 | 16913 | methyl- iso-borneol: 2-methyl- iso-borneol |
| 91-62-3 | 7059 | methyl quinoline: para-methyl quinoline |
| 08-09-59 | 227085 | Methyl iso-nicotinate |
| 119-36-8 | 4133 | methyl salicylate |
| 2432-51-1 | 62444 | Methyl Thiobutyrate |
| 1222-05-5 | 91497 | musk galaxolide |
| 1506-02-1 | 89440 | musk tonalid |
| 37677-14-8 | 93199 | myracaldehyde |
| 143-13-5 | 8918 | nonyl acetate |
| 4674-50-4 | 20797 | nootkatone |
| 111-87-5 | 957 | 1-octanol |
| 3391-86-4 | 18827 | octenol: 1- octen 3- of |
| 109-52-4 | 7991 | pentanoic acid |
| 591-80-0 | 61138 | 4-Pentenoic acid |
| 103-82-2 | 999 | Phenyl acetic acid |
| 536-74-3 | 10821 | phenyl acetylene |
| 60-12-8 | 6054 | phenyl Ethanol (lower con) |
| 60-12-8 | 6054 | phenyl Ethanol (higher con) |
| 78-59-1 | 6544 | phorone: iso-Phorone |
| 80-56-8 | 6654 | pinene: alpha-Pinene |
| 105-66-8 | 7770 | propyl butyrate |
| 135-79-5 | 67285 | propyl quinoline: iso-propyl quinoline |
| 111-47-7 | 8118 | Propyl sulfide |
| 110-86-1 | 1049 | pyridine |
| 94-59-7 | 5144 | safrole |
| 69460-08-8 | | sandiff |
| 115-71-9 | 5281531 | santalol |
| 83-34-1 | 6736 | skatole |
| 10482-56-1 | 17100 | Terpineol |
| 110-01-1 | 1127 | tetrahydro thiophene |
| 91-61-2 | 66678 | tetraquinone |
| 36267-71-7 | 61951 | thienopyrimidine |
| 123-93-3 | 31277 | thioglycolic acid |
| 110-02-1 | 8030 | thiophene |
| 89-83-8 | 6989 | Thymol |
| 529-20-4 | 10722 | tolualdehyde: ortho-Tolualdehyde |
| 108-88-3 | 1140 | toluene (lower con) |
| 108-88-3 | 1140 | toluene (higher con) |
| 75-50-3 | 1146 | trimethyl amine |
| 104-67-6 | 7714 | undecalactone: gamma-Undecalactone |
| 112-38-9 | 5634 | undecylenic acid |
| 590-86-3 | 11552 | valeraldehyde: iso-valeraldehyde |
| 503-74-2 | 10430 | valeric acid: iso-valeric acid |
| 108-29-2 | 7921 | valerolactone: gamma-valerolactone |
| 121-33-5 | 1183 | Vanillin |
| 122-48-5 | 31211 | Zingerone |

REFERENCES

1. Wandell, B. A. *Foundations of vision* (Sinauer Associates, 1995).
2. Bregman, A. S. *Auditory scene analysis: The perceptual organization of sound* (The MIT Press, 1994).
3. Stevenson, R. J. & Wilson, D. A. Odour perception: an object-recognition approach. *PERCEPTION-LONDON-* 36, 1821 (2007).
4. Gottfried, J. A. Central mechanisms of odour object perception. *Nature Reviews Neuroscience* (2010).
5. Barnes, D. C., Hofacer, R. D., Zaman, A. R., Rennaker, R. L. & Wilson, D. A. Olfactory perceptual stability and discrimination. *Nature neuroscience* 11, 1378-1380 (2008).
6. Wilson, D. A. Pattern Separation and Completion in Olfaction. *Annals of the New York Academy of Sciences* 1170, 306-312 (2009).
7. Kay, L. M., Crk, T. & Thorngate, J. A Redefinition of Odor Mixture Quality. *Behavioral neuroscience* 119, 726 (2005).
8. Koulakov, A. A., Enikolopov, A. G. & Rinberg, D. The structure of human olfactory space. *Arxiv preprint arXiv:0907.3964* (2009).
9. Khan, R. M., et al. Predicting odor pleasantness from odorant structure: pleasantness as a reflection of the physical world. *The Journal of Neuroscience* 27, 10015 (2007).
10. Haddad, R., et al. A metric for odorant comparison. *Nature Methods* 5, 425-429 (2008).
11. Madany Mamlouk, A., Chee-Ruiter, C., Hofmann, U. G. & Bower, J. M. Quantifying olfactory perception: mapping olfactory perception space by using multidimensional scaling and self-organizing maps. *Neurocomputing* 52, 591-597 (2003).
12. Aznar, M., LÛpez, R., Cacho, J. F. & Ferreira, V. Identification and quantification of impact odorants of aged red wines from Rioja. GC-olfactometry, quantitative GC-MS, and odor evaluation of HPLC fractions. *Journal of agricultural and food chemistry* 49, 2924-2929 (2001).
13. Grosch, W. Flavour of coffee. A review. *Food/Nahrung* 42, 344-350 (1998).
14. Dravnieks, A. Odor quality: semantically generated multi-dimensional profiles are stable. *Science* 218, 799-801 (1982).
15. Dravnieks, A. *Atlas of odor character profiles* (ASTM Press, PA, 1985).
16. Chen, S. S., Donoho, D. L. & Saunders, M. A. Atomic decomposition by basis pursuit. *SIAM journal on scientific computing* 20, 33-61 (1999).
17. Zarzo, M. & Stanton, D. T. Identification of latent variables in a semantic odor profile database using principal component analysis. *Chemical senses* 31, 713 (2006).
18. Zarzo, M. Psychologic dimensions in the perception of everyday odors: pleasantness and edibility. *Journal of Sensory Studies* 23, 354-376 (2008).
19. Mann, C. & Smith, T. An examination of Bulgarian rose oil by chromatographic and spectroscopic techniques. 458-460 (1977).
20. Ayc, F., Ayd nl, M., Bozdemir, A. & Tuta, M. Gas chromatographic investigation of rose concrete, absolute and solid residue. *Flavour and fragrance journal* 20, 481-486 (2005).
21. Laing, D. G. & Francis, G. W. The capacity of humans to identify odors in mixtures. *Physiology & behavior* 46, 809-814 (1989).
22. Laing, D. G. & Glemarec, A. Selective attention and the perceptual analysis of odor mixtures. *Physiology & behavior* 52, 1047-1053 (1992).
23. Jinks, A. & Laing, D. G. A limit in the processing of components in odour mixtures. *PERCEPTION-LONDON-* 28, 395-404 (1999).
24. Jinks, A. & Laing, D. G. The analysis of odor mixtures by humans: evidence for a configurational process. *Physiology & behavior* 72, 51-63 (2001).
25. Livermore, A. & Laing, D. G. The influence of odor type on the discrimination and identification of odorants in multicomponent odor mixtures. *Physiology & behavior* 65, 311-320 (1998).
26. Livermore, A. & Laing, D. G. Influence of training and experience on the perception of multicomponent odor mixtures. *Journal of Experimental Psychology: Human Perception and Performance* 22, 267 (1996).

27. Boyle, J. A., Djordjevic, J., Olsson, M. J., Lundst^m, J. N. & Jones-Gotman, M. The human brain distinguishes between single odorants and binary mixtures. *Cerebral Cortex* 19, 66 (2009).
28. Kadohisa, M. & Wilson, D. A. Separate encoding of identity and similarity of complex familiar odors in piriform cortex. *Proceedings of the National Academy of Sciences* 103, 15206 (2006).
29. Wilson, D. A. Odor specificity of habituation in the rat anterior piriform cortex. *Journal of Neurophysiology* 83, 139 (2000).
30. Loftus, G. R. & Masson, M. E. J. Using confidence intervals in within-subject designs. *Psychonomic Bulletin & Review* 1, 476-490 (1994).
1. Dravnieks, A. Odor quality: semantically generated multidimensional profiles are stable. *Science* 218, 799-801 (1982).
2. Dravnieks, A. *Atlas of odor character profiles* (ASTM Press, PA, 1985).
3. Khan, R. M., et al. Predicting odor pleasantness from odorant structure: pleasantness as a reflection of the physical world. *The Journal of Neuroscience* 27, 10015 (2007).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An odorant mixture, comprising N odorant components wherein N equals at least 20, each odorant component being characterized by a multidimensional vector of attributes, such that the mixture is characterized by N respective multidimensional vectors, wherein a z score of an average of characteristic distances between vectors corresponding to odorant components in the mixture and vectors corresponding to odorant components in a group of M odorant components but not in the mixture is less than 2, and wherein said M equals at least 100.

2. The odorant mixture according to claim 1, wherein at least a portion of said N odorant components is selected from said group of M odorant components.

3. The odorant mixture according to claim 1, wherein M is at least equal to N.

4. The odorant mixture according to claim 1, wherein said N odorant components have similar odor intensity.

5. The odorant mixture according to claim 1, wherein each characteristic distance is defined as a minimum distance between a vector corresponding to odorant components in the mixture and a vector corresponding to an odorant component in said group of M odorant components but not in the mixture.

6. The odorant mixture according to claim 1, wherein each of said multidimensional vectors has at least 50 dimensions.

7. The odorant mixture according to claim 1, wherein N equals at least 30.

8. The odorant mixture according to claim 1, wherein said group of M odorant components is selected from the odorant components listed in Table A.1 or Table A.2 of Annex 1.

9. The odorant mixture according to claim 1, wherein said group of M odorant components is the group listed in Table A.1 of Annex 1.

10. The odorant mixture according to claim 1, wherein said group of M odorant components is the group listed in Table A.2 of Annex 1.

11. The odorant mixture according to claim 1, wherein each of said N odorant component is in a gaseous state.

12. The odorant mixture according to claim 1, wherein said z-score is with respect to a synthetic database which comprises a plurality of entries, each corresponding to a database odorant mixture defined as being producible from a plurality of odorant components selected from said group of M odorant components.

13. A method of at least partially masking a target odor in an environment, comprising spreading an odorant mixture according to claim 1 in the environment, thereby providing a combined mixture having said odorant mixture and odorant components of the target odor.

14. The method according to claim 13, wherein a z score of an average of characteristic distances between vectors corresponding to odorant components in said combined mixture and vectors corresponding to odorant components in said group of M odorant components but not in said combined mixture is less than 1.

* * * * *